US009566341B1

(12) United States Patent
Stinchcomb et al.

(10) Patent No.: US 9,566,341 B1
(45) Date of Patent: *Feb. 14, 2017

(54) COMPOUNDS INCLUDING COX INHIBITOR MOIETY AND ENHANCED DELIVERY OF ACTIVE DRUGS USING SAME

(75) Inventors: Audra Stinchcomb, Baltimore, MD (US); Kyung Bo Kim, Lexington, KY (US); Ragotham Reddy Pinninti, Lexington, KY (US); Priyanka Ghosh, Baltimore, MD (US); Kalpana S. Paudel, Knoxville, TN (US)

(73) Assignee: University of Kentucky Research Foundation, Lexington, KY (US)

( * ) Notice: Subject to any disclaimer, the term of this patent is extended or adjusted under 35 U.S.C. 154(b) by 711 days.

This patent is subject to a terminal disclaimer.

(21) Appl. No.: 13/458,366

(22) Filed: Apr. 27, 2012

Related U.S. Application Data

(60) Provisional application No. 61/517,874, filed on Apr. 27, 2011.

(51) Int. Cl.
*A61K 47/48* (2006.01)
*A61K 9/70* (2006.01)
*A61K 9/00* (2006.01)

(52) U.S. Cl.
CPC .......... *A61K 47/481* (2013.01); *A61K 9/0021* (2013.01); *A61K 9/7023* (2013.01)

(58) Field of Classification Search
None
See application file for complete search history.

(56) References Cited

U.S. PATENT DOCUMENTS

| 6,569,449 | B1 | 5/2003 | Stinchcomb et al. |
| 7,229,556 | B1 | 6/2007 | Hinds, III et al. |
| 7,232,460 | B2 | 6/2007 | Van Erlach et al. |
| 7,511,054 | B2 | 3/2009 | Stinchcomb et al. |
| 7,759,358 | B2 | 7/2010 | Crooks et al. |
| 2002/0094515 | A1 | 7/2002 | Erlach et al. |
| 2002/0098472 | A1 | 7/2002 | Erlach et al. |
| 2002/0111377 | A1 | 8/2002 | Stinchcomb |
| 2002/0111551 | A1 | 8/2002 | Erlach et al. |
| 2003/0032892 | A1 | 2/2003 | Erlach et al. |
| 2004/0180036 | A1* | 9/2004 | Ashton ............... A61K 31/196 424/85.1 |
| 2005/0154002 | A1 | 7/2005 | Crooks et al. |
| 2005/0266061 | A1 | 12/2005 | Stinchcomb et al. |
| 2008/0008745 | A1 | 1/2008 | Stinchcomb et al. |
| 2008/0076789 | A1 | 3/2008 | Stinchcomb et al. |
| 2009/0017102 | A1 | 1/2009 | Stinchcomb et al. |
| 2009/0036523 | A1 | 2/2009 | Stinchcomb et al. |
| 2009/0143762 | A1 | 6/2009 | Stinchcomb et al. |
| 2009/0156814 | A1 | 6/2009 | Stinchcomb et al. |
| 2009/0246265 | A1 | 10/2009 | Stinchcomb et al. |
| 2009/0247619 | A1 | 10/2009 | Stinchcomb et al. |
| 2009/0291128 | A1 | 11/2009 | Stinchcomb et al. |
| 2010/0273895 | A1 | 10/2010 | Stinchcomb et al. |
| 2011/0052694 | A1 | 3/2011 | Stinchcomb et al. |
| 2011/0245288 | A1 | 10/2011 | Stinchcomb et al. |
| 2011/0245783 | A1 | 10/2011 | Stinchcomb et al. |
| 2012/0034293 | A1 | 2/2012 | Stinchcomb et al. |

OTHER PUBLICATIONS

Definition of "compound" and "composition" from the Grant & Hackh's Chemical Dictionary (1987) p. 148, McGraw-Hill, Inc.*
Miranda, H.F., Prieto, J.C., Pinardi, G. (2005) Spinal synergy between nonselective cyclooxygenase inhibitors and morphine antinociception in mice. Brain Research, vol. 1049, p. 165-170.*
Dhooper, Harpreet Kaur, "Opioid-Cannabinoid Codrugs With Enhanced Analgesic and Pharmacokinetic Profile" (2010). University of Kentucky Doctoral Dissertations. Paper 98. <http://uknowledge.uky.edu/gradschool_diss/98>.*
Hermanson, G.T. (1996) "Zero-Length Cross-linkers" in Bioconjugate Techniques, p. 617-618, Academic Press, Elsevier.*
Zalipsky, S. (1995) Functionalized Poly(ethylene glycol) for Preparation of Biologically Relevant Conjugates. Bioconjugate Chemistry, vol. 6, p. 150-165.*
Ghosh, P. et al "Optimization of natrexone diclofenac codrugs . . . " Pharm. Res. (2014) vol. 31, pp. 148-159.*
King, A. et al "Effects of naltrexone on smoking cessation . . . " J. Clin. Pharmacol. (2012) vol. 32, pp. 630-636.*
Reece AS (2011) Hypothalamic opioid-melanocortin appetitive balance and addictive craving. Med Hypotheses 76 (1):132-137.
Rehm J, Mathers C, Popova S, Thavorncharoensap M, Teerawattananon Y and Patra J (2009) Global burden of disease and injury and economic cost attributable to alcohol use and alcoholuse disorders. Lancet 373 (9682):2223-2233.
Roberts WJ and Sloan KB (1999) Correlation of aqueous and lipid solubilities with flux for prodrugs of 5-fluorouracil, theophylline, and 6-mercaptopurine: A Potts-Guy approach. J Pharm Sci 88(5):515-522.
Roche DJ, Childs E, Epstein AM and King AC (2010) Acute HPA axis response to naltrexone differs in female vs. male smokers. Psychoneuroendocrinology 35(4):596-606.
Rukstalis MR, Stromberg MF, O'Brien CP and Volpicelli JR (2000) 6-beta-naltrexol reduces alcohol consumption in rats. Alcohol Clin Exp Res 24(10):1593-1596.
Schuckit M (2009) Alcohol-use disorders. Lancet 373:492-501.
Shaw D and al'Absi M (2010) Blunted opiate modulation of prolactin response in smoking men and women. Pharmacol Biochem Behav 95(1):1-5.
Sinha R (2007) The role of stress in addiction relapse. Curr Psychiatry Rep 9(5):388-395.
Soyka M and Rosner S (2010) Emerging drugs to treat alcoholism. Expert Opin Emerg Drugs 15(4):695-711.
Stinchcomb AL, Dua R, Paliwal A, Woodard RW and Flynn GL (1995) A solubility and related physicochemical property comparison of buprenorphine and its 3-alkyl esters. Pharm Res 12(10):1526-1529.

(Continued)

*Primary Examiner* — Leigh C Maier
(74) *Attorney, Agent, or Firm* — Stites & Harbison PLLC; Mandy Wilson Decker

(57) ABSTRACT

The presently-disclosed subject matter includes compounds including a cyclooxygenase enzyme inhibitor moiety and a moiety derived from a drug of interest. In some embodiments, the drug of interest is an opioid. In some embodiments, the compound includes a diclofenac moiety and a naltrexone or naltrexol moiety. The compounds allow for enhanced delivery rates across skin.

10 Claims, 21 Drawing Sheets

(56) References Cited

OTHER PUBLICATIONS

Stinchcomb AL, Swaan PW, Ekabo O, Harris KK, Browe J, Hammell DC, Cooperman TA and Pearsall M (2002) Straight-chain naltrexone ester prodrugs: diffusion and concurrent esterase biotransformation in human skin. J Pharm Sci 91(12):2571-2578.
Strasinger CL, Scheff NN and Stinchcomb AL (2008) Prodrugs and codrugs as strategies for improving percutaneuos absorption. Expert Review of Dermatology 3(2):221-233.
Vaddi HK, Banks SL, Chen J, Hammell DC, Crooks PA and Stinchcomb AL (2009) Human skin permeation of 3-O-alkyl carbamate prodrugs of naltrexone. J Pharm Sci 98(8)2611-2625.
Vaddi HK, Hamad MO, Chen J, Banks SL, Crooks PA and Stinchcomb AL (2005) Human skin permeation of branched-chain 3-0-alkyl ester and carbonate prodrugs of naltrexone. Pharm Res 22(5):758-765.
Valiveti S, Hammell DC, Paudel KS, Hamad MO, Crooks PA and Stinchcomb AL (2005a) In vivo evaluation of 3-O-alkyl ester transdermal prodrugs of naltrexone in hairless guinea pigs. J Control Release 102(2):509-520.
Valiveti S, Paudel KS, Hammell DC, Hamad MO, Chen J, Crooks PA and Stinchcomb AL (2005b) In vitro/in vivo correlation of transdermal naltrexone prodrugs in hairless guinea pigs. Pharm Res 22(6):981-989.
Verebey K, Volavka J, Mule SJ and Resnick RB (1976) Naltrexone: disposition, metabolism, and effects after acute and chronic dosing. Clin Pharmacol Ther 20(3)315-328.
Volpicelli JR, Alterman AI, Hayashida M and O'Brien CP (1992) Naltrexone in the treatment of alcohol dependence. Arch Gen Psychiatry 49(11):876-880.
Volpicelli JR, Rhines KC, Rhines JS, Volpicelli LA, Alterman AI and O'Brien CP (1997) Naltrexone and alcohol dependence. Role of subject compliance. Arch Gen Psychiatry 54(8):737-742.
Wall ME, Brine DR and Perez-Reyes M (1981) Metabolism and disposition of naltrexone in man after oral and intravenous administration. Drug Metab Dispos 9(4):369-375.
Wermeling DP, Banks SL, Hudson DA, Gill HS, Gupta J, Prausnitz MR and Stinchcomb AL (2008) Microneedles permit transdermal delivery of a skin-impermeant medication to humans. Proc Natl Acad Sci U S A 105(6):2058-2063.
WHO (2004) Global status report on alcohol 2004., in World Health Organization, Geneva.
Yu CD, Fox JL, Ho NFH and Higuchi WI (1979) Physical Model Evaluation of Topical Prodrug Delivery—Simultaneous Transport and Bioconversion of Vidarabine-5'-Valerate .1. Physical Model Development. Journal of Pharmaceutical Sciences 68(11):1341-1346.
Zarkin GA, Bray JW, Aldridge A, Mills M, Cisler RA, Couper D, McKay JR and O'Malley S (2010) The effect of alcohol treatment on social costs of alcohol dependence: results from the COMBINE study. Med Care 48(5)396-401.
B.S. Somashekar, G. A. N. G., A.R. Ramesha and C.L. Khetrapal (2005). "Protonation of trimipramine salts of maleate, mesylate and hydrochloride observed by 1H, 13C and 15N NMR spectroscopy." Magnetic Resonance Chemistry 43: 166-170.
Baba, A. and T. Yoshioka (2006). "Synthesis of 1-beta-O-acyl glucuronides of diclofenac, mefenamic acid and (S)-naproxen by the chemo-selective enzymatic removal of protecting groups from the corresponding methyl acetyl derivatives." Organic & Biomolecular Chemistry 4(17): 3303-3310.
Ballard, T. E., J. J. Richards, et al. (2008). "Synthesis and Antibiofilm Activity of a Second-Generation Reverse-Amide Oroidin Library: A Structure-Activity Relationship Study." Chemistry-a European Journal 14(34): 10745-10761.
Bellouard, F., F. Chuburu, et al. (1999). "A convenient synthetic route to polyether-tagged cyclam ligands and their nickel derivatives." European Journal of Organic Chemistry(12): 3257-3261.
Bonina, F. P., C. Puglia, et al. (2001). "In vitro and in vivo evaluation of polyoxyethylene esters as dermal prodrugs of ketoprofen, naproxen and diclofenac." European Journal of Pharmaceutical Sciences 14(2): 123-134.

Decosta, B. R., M. J. Iadarola, et al. 1992). "Probes for narcotic receptor mediated phenomena. 18. epimeric 6-alpha-iodo-3,14-dihydroxy-17-(cyclopropylmethyl)-4,5-alpha-epoxymorphi nans and 6-beta-iodo-3,14-dihydroxy-17-(cyclopropylmethyl)-4,5-alpha-epoxymorphin ans as potential ligands for opioid receptor single photon-emission computed-tomography—synthesis, evaluation, and radiochemistry of i-125 6-beta-iodo-3,14-dihydroxy-17-(cyclopropylmethyl)-4,5-alpha-epoxymorphin an." Journal of Medicinal Chemistry (35): 2826-2835.
Du, W. T., L. Hong, et al. (2007). "Synthesis and evaluation of water-soluble docetaxel prodrugs-docetaxel esters of malic acid." Bioorganic & Medicinal Chemistry 15(18): 6323-6330.
G. Venkateswar Reddy, R. S. C. K., K. Suresh Babu, J. Madhusudana Rao (2009). "Stereoselective syntheses of 11-a-methoxycurvularin and 11-b-methoxycurvularin." Tetrahedron Letters 50: 4117-4120.
Hamad, M. O., P. K. Kiptoo, et al. (2006). "Synthesis and hydrolytic behavior of two novel tripartate codrugs of naltrexone and 6 beta-naltrexol with hydroxybupropion as potential alcohol abuse and smoking cessation agents." Bioorganic & Medicinal Chemistry 14(20): 7051-7061.
Jiang, Z. X. and Y. B. Yu (2008). "The design and synthesis of highly branched and spherically symmetric fluorinated macrocyclic chelators." Synthesis-Stuttgart(2): 215-220.
Krivickas, S. J., E. Tamanini, et al. (2007). "Effective Methods for the Biotinylation of Azamacrocycles." The Journal of Organic Chemistry 72(22): 8280-8289.
Mantarosie, L., S. Coman, et al. (2008). "Comparative behavior of various lipases in benign water and ionic liquids solvents." Journal of Molecular Catalysis a-Chemical 279(2): 223-229.
Mizrahi, B. and A. J. Domb (2009). "Anhydride Prodrug of Ibuprofen and Acrylic Polymers." Aaps Pharmscitech 10(2): 453-458.
Nelson, T. D., R. D. Davis, et al. (1994). "Synthesis and opioid receptor affinity of a series of aralkyl ethers of 6-alpha-naltrexol and 6-beta-naltrexol." Journal of Medicinal Chemistry 37(25): 4270-4277.
Paun, C., C. C Stere, al. et al (2008). "Acylation of sulfonamines using silica grafted 1-butyl-3-(3-triethoxysilylpropyl)-4,5-dihydroimidazolium ionic liquids as catalysts." Catalysis Today 131(1-4): 98-103.
Pelotte, A. L., R. M. Smith, et al. (2009). "Design, synthesis, and characterization of 6[beta]-naltrexol analogs, and their selectivity for in vitro opioid receptor subtypes." Bioorganic & Medicinal Chemistry Letters 19(10): 2811-2814.
Rouquayrol, M., B. Gaucher, et al. (2001). "Synthesis and anti-HIV activity of glucose-containing prodrugs derived from saquinavir, indinavir and nelfinavir." Carbohydrate Research 336(3): 161-180.
Simas, A. B. C., K. C. Pais, et al. (2003). "A More Convenient and General Procedure for O-Monobenzylation of Diols via Stannylenes: A Critical Reevaluation of the Bu2SnO Method." The Journal of Organic Chemistry 68(13): 5426-5428.
Sunazuka, T., K. Tsuzuki, et al. (1992). "Synthesis of 1233a analogs and their inhibitory activity against hydroxymethylglutaryl coenzyme a synthase." Journal of Antibiotics 45(7): 1139-1147.
Prausnitz MR, Mitragotri S, Langer R 2004. Current status and future potential of transdermal drug delivery. Nat Rev Drug Discov 3(2):115-124.
Prausnitz MR, Langer R 2008. Transdermal drug delivery. Nat Biotech 26(11):1261-1268.
Prausnitz MR 2004. Microneedles for transdermal drug delivery. Advanced Drug Delivery Reviews 56(5):581-587.
Gill HS, Denson DD, Burris BA, Prausnitz MR 2008. Effect of Microneedle Design on Pain in Human Volunteers. The Clinical Journal of Pain 24(7):585-594 510.1097/AJP. 1090b1013e31816778f31816779.
Lee Y-k, Park S-w, Kim Y-k, Kim D-j, Jeong J, Myrick H, Kim Y-h 2005. Effects of naltrexone on the ethanol-induced changes in the rat central dopaminergic system Alcohol and Alcoholism 40(4):297-301.
Swift R 2010. Medications Acting on the Dopaminergic System in the Treatment of Alcoholic Patients. Current Pharmaceutical Design 16(19):2136-2140.

(56) References Cited

OTHER PUBLICATIONS

Hulse GK, Basso MR 2000. The association between naltrexone compliance and daily supervision. Drug and Alcohol Review 19(1):41-48.
Hammell DC, Hamad M, Vaddi HK, Crooks PA, Stinchcomb AL 2004. A duplex "Gemini" prodrug of naltrexone for transdermal delivery. Journal of Controlled Release 97(2):283-290.
Banks S, Pinninti R, Gill H, Crooks P, Prausnitz M, Stinchcomb A 2008. Flux Across Microneedle-treated Skin is Increased by Increasing Charge of Naltrexone and Naltrexol In Vitro. Pharmaceutical Research 25(8):1964-1964.
Verebey K, Volavka J, Mule SJ, Resnick RB 1976. Naltrexone: disposition, metabolism, and effects after acute and chronic dosing. Clin Pharmacol Ther 20(3):315-328.
Kalluri H, Banga A 2011. Formation and Closure of Microchannels in Skin Following Microporation. Pharmaceutical Research 28(1):82-94.
Feingold K 2002. In This Issue: Regulation of Permeability Barrier Homeostasis. 119(5):986-986.
Feingold KR, Schmuth M, Elias PM 0000. The Regulation of Permeability Barrier Homeostasis. J Invest Dermatol 127 (7):1574-1576.
Menon GK, Feingold KR, Elias PM 1992. Lamellar Body Secretory Response to Barrier Disruption. J Investig Dermatol 98(3):279-289.
Grubauer G, Elias PM, Feingold KR 1989. Transepidermal water loss: the signal for recovery of barrier structure and function. Journal of Lipid Research 30(3):323-333.
Fecker LF, Stockfleth E, Nindl I, Ulrich C, Forschner T, Eberle J 2007. The role of apoptosis in therapy and prophylaxis of epithelial tumours by nonsteroidal anti-inflammatory drugs (NSAIDs). British Journal of Dermatology 156:25-33.
Davidson JM, Breyer MD 2003. Inflammatory Modulation and Wound Repair. J Investig Dermatol 120(5):xi-xii.
Muller-Decker K, Hirschner W, Marks F, Furstenberger G 2002. The Effects of Cyclooxygenase Isozyme Inhibition onIncisional Wound Healing in Mouse Skin. 119(5):1189-1195.
Futagami A, Ishizaki M, Fukuda Y, Kawana S, Yamanaka N 0000. Wound Healing Involves Induction of Cyclooxygenase-2 Expression in Rat Skin. Lab Invest 82(11):1503-1513.
Schmid-Wendtner MH, Korting HC 2006. The pH of the Skin Surface and Its Impact on the Barrier Function. Skin Pharmacology and Physiology 19(6):296-302.
Vaddi HK, Banks SL, Chen J, Hammell DC, Crooks PA, Stinchcomb AL 2009. Human skin permeation of 3-O-alkyl carbamate prodrugs of naltrexone. Journal of Pharmaceutical Sciences 98(8):2611-2625.
Prusakiewicz J, Ackermann C, Voorman R 2006. Comparison of Skin Esterase Activities from Different Species. Pharmaceutical Research 23(7):1517-1524.
Oesch F, Fabian E, Oesch-Bartlomowicz B, Werner C, Landsiedel R 2007. Drug-Metabolizing Enzymes in the Skin of Man, Rat, and Pig. Drug Metabolism Reviews 39(4):659-698.
Banks SL, Hamad M, Pinninti R, Gill HS, Crooks PA, Prausnitz MR and Stinchcomb AL (2010) Transdermal delivery of naltrexol and skin permeability lifetime after microneedle treatment in hairless guinea pigs Journal of Pharmaceutical Sciences 99(7):3072-3080.
Banks SL, Paudel KS, Brogden NK, Loftin CD and Stinchcomb AL (2011) Diclofenac Enables Prolonged Delivery of Naltrexone Through Microneedle-Treated Skin. Pharm Res 28(5):1211-1219.
Banks SL, Pinninti RR, Gill HS, Crooks PA, Prausnitz MR and Stinchcomb AL (2008) Flux across [corrected] microneedle-treated skin is increased by increasing charge of naltrexone and naltrexol in vitro. Pharm Res 25 (7):1677-1685.
Casswell S and Thamarangsi T (2009) Reducing harm from alcohol: call to action. Lancet 373:2247-2257.
Cone EJ, Gorodetzky CW and Yeh SY (1974) The urinary excretion profile of naltrexone and metabolites in man. Drug Metab Dispos 2(6):506-512.
Cynkowski T, Cynkowska G and Walters KA (2008) Codrugs: potential therapies for dermatological diseases. Dermatologic, Cosmeceutic, and Cosmetic Development:255-266.
Ferrari A, Bertolotti M, Dell'Utri A, Avico U and Sternieri E (1998) Serum time course of naltrexone and 6 beta-naltrexol levels during long-term treatment in drug addicts. Drug Alcohol Depend 52(3):211-220.
Fortin JP, Ci L, Schroeder J, Goldstein C, Montefusco MC, Peter I, Reis SE, Huggins GS, Beinborn M and Kopin AS (2010) The mu-opioid receptor variant N190K is unresponsive to peptide agonists yet can be rescued by small-molecule drugs. Mol Pharmacol 78(5):837-845.
Garbutt JC (2010) Efficacy and tolerability of naltrexone in the management of alcohol dependence. Curr Pharm Des 16(19):2091-2097.
Garbutt JC, Kranzler HR, O'Malley SS, Gastfriend DR, Pettinati HM, Silverman BL, Loewy JW and Ehrich EW (2005) Efficacy and tolerability of long-acting injectable naltrexone for alcohol dependence: a randomized controlled trial. Jama 293(13):1617-1625.
Grant JE, Odlaug BL and Kim SW (2010) a double-blind, placebo-controlled study of N-acetyl cysteine plus naltrexone for methamphetamine dependence. Eur Neuropsychopharmacol 20(11):823-828.
Greenway FL, Dunayevich E, Tollefson G, Erickson J, Guttadauria M, Fujioka K and Cowley MA (2009) Comparison of combined bupropion and naltrexone therapy for obesity with monotherapy and placebo. J Clin Endocrinol Metab 94 (12):4898-4906.
Greenway FL, Fujioka K, E, Plodkowski RA, Mudaliar S, Guttadauria M, Erickson J, Kim DD and Dunayevich E (2010) Effect of naltrexone plus bupropion on weight loss in overweight and obese adults (COR-I): a multicentre, randomised, double-blind, placebo-controlled, phase 3 trial. Lancet 376(9741):595-605.
Gueorguieva R, Wu R, Donovan D, Rounsaville BJ, Couper D, Krystal JH and O'Malley SS (2010) Naltrexone and combined behavioral intervention effects on trajectories of drinking in the COMBINE study. Drug Alcohol Depend 107 (2-3):221-229.
Haggkvist J, Lindholm S and Franck J (2009a) The effect of naltrexone on amphetamine-induced conditioned place preference and locomotor behaviour in the rat. Addict Biol 14(3):260-269.
Haggkvist J, Lindholm S and Franck J (2009b) The opioid receptor antagonist naltrexone attenuates reinstatement of amphetamine drug-seeking in the rat. Behav Brain Res 197(1):219-224.
Ioannides-Demos LL, Piccenna L and McNeil JJ (2011) Pharmacotherapies for obesity: past, current, and future therapies. J Obes 2011:179674.
Kalluri H and Banga A (2009) Microneedles and transdermal drug delivery. Journal of Drug Delivery Science and Technology 19(5):303-310.
Karila L, Weinstein A, Aubin HJ, Benyamina A, Reynaud M and Batki SL (2010) Pharmacological approaches to methamphetamine dependence: a focused review. Br J Clin Pharmacol 69(6):578-592.
Kaushik S, Hord AH, Denson DD, McAllister DV, Smitra S, Allen MG and Prausnitz MR (2001) Lack of pain associated with microfabricated microneedles. Anesth Analg 92(2):502-504.
Kiptoo PK, Hamad MO, Crooks PA and Stinchcomb AL (2006) Enhancement of transdermal delivery of 6-beta-naltrexol via a codrug linked to hydroxybupropion. J Control Release 113(2):137-145.
Kiptoo PK, Paudel KS, Hammell DC, Hamad MO, Crooks PA and Stinchcomb AL (2008) In vivo evaluation of a transdermal codrug of 6-beta-naltrexol linked to hydroxybupropion in hairless guinea pigs. Eur J Pharm Sci 33 (4-5):371-379.
Kranzler HR and Edenberg HJ (2010) Pharmacogenetics of alcohol and alcohol dependence treatment. Curr Pharm Des 16(19):2141-2148.
Kranzler HR, Modesto-Lowe V and Van Kirk J (2000) Naltrexone vs. nefazodone for treatment of alcohol dependence. A placebo-controlled trial. Neuropsychopharmacology 22(5):493-503.
Martinotti G, Di Nicola M, Tedeschi D, Andreoli S, Reina D, Pomponi M, Mazza M, Romanelli R, Moroni N, De Filippis R, Di Giannantonio M, Pozzi G, Bria P and Janiri L (2010) Pregabalin versus naltrexone in alcohol dependence: a randomised, double-blind, comparison trial. J Psychopharmacol 24(9):1367-1374.

(56) References Cited

OTHER PUBLICATIONS

McAllister DV, Wang PM, Davis SP, Park JH, Canatella PJ, Allen MG and Prausnitz MR (2003) Microfabricated needles for transdermal delivery of macromolecules and nanoparticles: fabrication methods and transport studies. Proc Natl Acad Sci U S A 100(24):13755-13760.

McCaul ME, Wand GS, Eissenberg T, Rohde CA and Cheskin LJ (2000a) Naltrexone alters subjective and psychomotor responses to alcohol in heavy drinking subjects. Neuropsychopharmacology 22(5):480-492.

McCaul ME, Wand GS, Rohde C and Lee SM (2000b) Serum 6-beta-naltrexol levels are related to alcohol responses in heavy drinkers. Alcohol Clin Exp Res 24(9):1385-1391.

Meyer MC, Straughn AB, Lo MW, Schary WL and Whitney CC (1984) Bioequivalence, doseproportionality, and pharmacokinetics of naltrexone after oral administration. J Clin Psychiatry 45(9 Pt 2):15-19.

Milewski M, Brogden NK and Stinchcomb AL (2010a) Current aspects of formulation efforts and pore lifetime related to microneedle treatment of skin. Expert Opin Drug Deliv 7(5):617-629.

Milewski M and Stinchcomb AL (2010) Vehicle composition influence on the microneedle-enhanced transdermal flux of naltrexone hydrochloride. Pharm Res Epub ahead of print.

Milewski M and Stinchcomb AL (2011) Vehicle composition influence on the microneedle-enhanced transdermal flux of naltrexone hydrochloride. Pharm Res 28(1):124-134.

Milewski M, Yerramreddy TR, Ghosh P, Crooks PA and Stinchcomb AL (2010b) In vitro permeation of a pegylated naltrexone prodrug across microneedle-treated skin. Journal of Controlled Release 146(1):37-44.

Morley KC, Teesson M, Sannibale C, Baillie A and Haber PS (2010) Clinical predictors of outcome from an Australian pharmacological relapse prevention trial. Alcohol Alcohol 45(6):520-526.

O'Malley SS (1996) Opioid antagonists in the treatment of alcohol dependence: clinical efficacy and prevention of relapse. Alcohol Alcohol 31 Suppl 1:77-81.

O'Malley SS, Jaffe AJ, Chang G, Schottenfeld RS, Meyer RE and Rounsaville B (1992) Naltrexone and coping skills therapy for alcohol dependence. A controlled study. Arch Gen Psychiatry 49(11):881-887.

Paudel KS, Nalluri BN, Hammell DC, Valiveti S, Kiptoo P, Hamad MO, Crooks PA and Stinchcomb AL (2005) Transdermal delivery of naltrexone and its active metabolite 6-beta-naltrexol in human skin in vitro and guinea pigs in vivo. J Pharm Sci 94(9):1965-1975.

Pettinati HM, Oslin DW, Kampman KM, Dundon WD, Xie H, Gallis TL, Dackis CA and O'Brien CP (2010) A Double-Blind, Placebo-Controlled Trial Combining Sertraline and Naltrexone for Treating Co-Occurring Depression and Alcohol Dependence. Am J Psychiatry.

Pillai O, Hamad MO, Crooks PA and Stinchcomb AL (2004) Physicochemical evaluation, in vitro human skin diffusion, and concurrent biotransformation of 3-O-alkyl carbonate prodrugs of naltrexone. Pharm Res 21(7):1146-1152.

Potts RO, Bommannan D, Wong O, Tamada JA, Riviere JE and Monteiro-Riviere NA (1997) Transdermal peptide delivery using electroporation. Pharm Biotechnol 10:213-238.

Potts RO and Guy RH (1992) Predicting skin permeability. Pharm Res 9(5):663-669.

Prausnitz MR and Langer R (2008) Transdermal drug delivery. Nat Biotechnol 26(11):1261-1268.

Ray LA, Hutchison KE, Ashenhurst JR and Morrow AL (2010b) Naltrexone selectively elevates GABAergic neuroactive steroid levels in heavy drinkers with the ASP40 allele of the OPRM1 gene: a pilot investigation. Alcohol Clin Exp Res 34(8):1479-1487.

Haranath KV, Mohamed OH, Jianhong C, Stan LB, Peter AC, Audra LS 2005. Human skin permeation of branched-chain 3-0-alkyl ester and carbonate prodrugs of naltrexone. Pharm Res 22(5):758-765.

Barr CS, Chen SA, Schwandt ML, Lindell SG, Sun H, Suomi SJ and Heilig M (2010) Suppression of alcohol preference by naltrexone in the rhesus macaque: a critical role of genetic variation at the micro-opioid receptor gene locus. Biol Psychiatry 67(1):78-80.

Breese GR, Chu K, Dayas CV, Funk D, Knapp DJ, Koob GF, Le DA, O'Dell LE, Overstreet DH, Roberts AJ, Sinha R, Valdez GR and Weiss F (2005) Stress enhancement of craving during sobriety: a risk for relapse. Alcohol Clin Exp Res 29(2):185-195.

Epperson CN, Toll B, Wu R, Amin Z, Czarkowski KA, Jatlow P, Mazure CM and O'Malley SS (2010) Exploring the impact of gender and reproductive status on outcomes in a randomized clinical trial of naltrexone augmentation of nicotine patch. Drug Alcohol Depend 112(1-2):1-8.

Koob GF and Le Moal M (2005) Plasticity of reward neurocircuitry and the 'dark side' of drug addiction. Nat Neurosci 8 (11):1442-1444.

Mark TL, Kassed, C.A., Vandivort-Warren, R. Levit, K.R., & Kranzler, H.R. (2009) Alcohol and opioid dependence medications: Prescription trends, overall and by physician specialty . . . Drug and Alcohol Dependence 99:345-349.

Mokdad AH, Marks JS, Stroup DF and Gerberding JL (2004) Actual causes of death in the United States, 2000. JAMA 291(10)1 238-1245.

* cited by examiner

COMPOUNDS INCLUDING COX INHIBITOR MOIETY AND ENHANCED DELIVERY OF ACTIVE DRUGS USING SAME

RELATED APPLICATIONS

This application claims priority from U.S. Provisional Application Ser. No. 61/517,874 filed Apr. 27, 2011, the entire disclosure of which is incorporated herein by this reference.

GOVERNMENT INTEREST

This invention was made with government support under NIH R01DA13425 awarded by the National Institutes of Health. The government has certain rights in the invention.

TECHNICAL FIELD

The presently-disclosed subject matter relates to compounds including a cyclooxygenase enzyme inhibitor moiety. In some embodiments, the compound includes a Cox inhibitor moiety and an opioid. The compounds allow for improved microneedle-enhanced delivery rates across skin, as well as an increase in the pore lifetime or duration of delivery.

INTRODUCTION

According to the National Survey of Drug Use and Health (NSDUH) of 2008, 7.2 million Americans are in need of treatment for Substance-Related Disorders (SRDs), and a large proportion of those need treatment for opiate pain reliever and heroin addiction. Additionally, over 8.5% of the U.S. population and 75 million people worldwide meet the diagnostic criteria for alcohol use disorders (AUDs), with alcohol abuse being among the top three preventable public health problems in the U.S. and the world.

Opioid and alcohol abuse are major worldwide problems connected with tremendous social and personal strife. The CDC reported in February 2011 that the abuse of and deaths from prescription opioid narcotics has reached epidemic levels. In May 2009 the Columbia University National Center on Addiction and Substance Abuse reported that $468 billion dollars were spent by the Government in 2005 on expenses related to smoking, alcohol abuse, and illegal drugs. Prevention, treatment and addiction research spending comprised only about 2% of that $468 billion. Taxpayers would benefit if more of that budget were spent on treatment options, rather than law enforcement expenses and the healthcare cost burden that comes from patients who develop cirrhosis, lung and cardiovascular disease, and a variety of cancers, not to mention the expense of emergency room visits for overdoses.

The latest NHSDA (National Household Survey on Drug Abuse) report conducted by the Substance Abuse and Mental Health Services Administration reported in July 2007 that nearly one in 12 full time workers in the US have serious enough drug/alcohol problems to require medical treatment. The 2008 National Survey of Drug Use and Health (NSDUH) estimated that approximately 7.2 million Americans were in need of treatment for illicit drug use. Unfortunately, most of these individuals do not seek treatment. However, for those who do seek treatment, the third and fourth most common substance abuse types are opiate pain reliever and heroin, respectively. Providing recovery help for addicts with pharmacological interventions has proven helpful. In 2003, the number of prescriptions for two buprenorphine formulations for the treatment of opioid dependence increased from 48,000 ($5 million) to 1.9 million ($327 million) in 2007 (Mark, 2009). Unfortunately, the buprenorphine sublingual tablets have a very bitter taste and potential for "peak" plasma drug level related side effects (dizziness, sedation, orthostatic hypotension), and the poor acceptance of the drug has limited the use.

Alcohol use disorders (AUDs) are a major public health problem (Breese et al., 2005; Koob and Le Moal, 2005; Sinha, 2007), and alcohol abuse is one of the leading causes of death in the United States, contributing to over 80,000 deaths annually (Mokdad et al., 2004). Alcohol consumption accounts for 9% of the disease burden in developed countries and is linked to more than 60 diseases including cancers, cardiovascular diseases, liver cirrhosis, neuropsychiatric disorders, injuries and fetal alcohol syndrome (Casswell and Thamarangsi, 2009; Schuckit, 2009; WHO, 2004). Prescriptions for alcoholism increased from 393,000 ($30 million) in 2003 to 720,000 ($78 million) in 2007. Disulfiram, naltrexone, and acamprosate prescriptions dominate the market (Mark, 2009).

The leading cause of preventable deaths in the United States is cigarette smoking, with over 440,000 premature deaths occurring each year. Cigarette smoking is known to reduce appetite and increase the rate of cellular metabolism, leading to body mass stabilization or reduction. One of the main reasons for recidivism in persons trying to quit smoking is the potential for weight gain, especially in women. Regardless of the varied findings of the many studies on smoking cessation and weight gain, the primary recommendation has been to incorporate weight loss treatment with smoking cessation. Naltrexone (NTX) may be a potential weight loss drug candidate, especially in combination with bupropion (Greenway et al., 2009; Greenway et al., 2010; Ioannides-Demos et al., 2011); and the biochemical relationship between appetite and addictive craving is receiving increasing attention (Reece, 2011). Interesting positive clinical results have been seen when women smokers are treated with a combination of NTX and nicotine patches (Epperson et al., 2010; Roche et al., 2010; Shaw and al'Absi, 2010).

Good clinical trial results and preclinical data have shown a reduction in amphetamine and methamphetamine use with NTX treatment (Grant et al., 2010; Haggkvist et al., 2009a; Haggkvist et al., 2009b; Karila et al., 2010). Studies with many other drugs have shown a lack of success for methamphetamine dependence treatment, therefore NTX may be a very good option (Karila et al., 2010).

Naltrexone (NTX), an opioid antagonist, is currently prescribed as an oral tablet or 30-day depot injection form to help maintain opioid addicts in a drug-free state. Unfortunately, postmarketing reports of serious injection site reactions (cellulitis, abscess, and necrosis) have recently required patient warning updates for the depot injection, and the oral dosage form is associated with many gastrointestinal side effects. NTX is also FDA-approved for the treatment of alcohol dependence. Substantial clinical evidence exists for the benefits of NTX treatment in smoking cessation, especially in women. Very intriguing clinical trial data has also been observed in amphetamine-dependent individuals, which is especially important as methamphetamine dependence has no FDA-approved treatment options. Preclinical data also exists that suggests that NTX may benefit anabolic androgenic steroid dependency. Treatment with NTX in the 90's produced variable success rates in addicts; however, current clinical NTX therapy is being optimized based on human pharmacogenetic data.

Transdermal delivery of NTX is desirable for addicts in order to help reduce side effects associated with oral (hepatotoxicity at high doses in hepatocompromised addicts) and injectable therapies, and improve compliance. Permeation through the skin allows the drug to directly enter the systemic circulation and avoid the first pass effect. NTX itself does not have the essential physicochemical properties that would allow a therapeutic dose of the drug to cross the human skin barrier.

Microneedle (MN)-enhanced transdermal delivery is an efficient and painless method for increasing the skin permeation of many drugs, including NTX. The major limitation of MN-enhanced delivery is that the micropore lifetime only allows delivery of drug for two to three days. Therapeutic viability of NTX treatment would be improved by a product that allows for less-frequent treatment.

Accordingly, there remains a need in the art for novel compounds and methods that allow for a therapeutically successful drug delivery system that allows for less-frequent administration.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

Cyclooxygenase (COX) enzyme inhibitors, such as diclofenac, can prolong the lifetime of micropores of microneedle (MN)-enhanced transdermal delivery systems, allowing delivery of a drug to extend beyond a few days, allowing for less-frequent patch dosing (e.g., once a week). Many of the COX inhibitors are weak acids, and opioid antagonists, such as naltrexone and naltrexol, and many other desirable transdermal drugs are weak bases. It is difficult to formulate high concentrations of a weak base and a weak acid in the same system, due to chemical stability and solubility issues.

The presently-disclosed subject matter includes compounds including a first moiety derived from an drug of interest; and a second moiety derived from a cyclooxygenase (COX) enzyme inhibitor, wherein the first moiety is linked to the second moiety to form a single chemical entity. The compounds of the presently-disclosed subject matter improved microneedle-enhanced delivery rates across skin, as well as an increase in the pore lifetime or duration of delivery. Without wishing to be bound by theory or mechanism, the cox inhibitor component of the compound allows for pores to remain open for a longer time period, allowing for improved delivery of the first moiety/drug of interest. In some embodiments, the first moiety is derived from a drug with a phenolic hydroxyl or hydroxyl group. In some embodiment, the first moiety is derived from an opioid. In some embodiments, the first moiety is derived from an opioid antagonist.

Compounds of the presently-disclosed subject matter are useful for use in a therapeutically-successful delivery system that allows for less-frequent dosing. In some embodiments, the compounds can be used in an MN transdermal delivery system to provide a therapeutic transdermal delivery rate of an opioid antagonist (e.g., naltrexone or naltrexol). Contemplated delivery rates across the skin are improved because of optimized physicochemical properties for faster diffusion.

In some embodiments, the opioid from which the first moiety is derived is selected from: naltrexone, buprenorphine, butorphanol, codeine, cyclazocine, cyclorphan, oxilorphan, dihydrocodeine; dihydromorphine, ethymorphine, hydromorphone, levallorphan, levorphanol, nalbuphine, nalmefene, nalorphine, naloxone, naltrexol, phenazocine, and pholcodine. In some embodiments, the opioid antagonist is naltrexsone or naltrexol.

In some embodiments, the COX enzyme inhibitor from which the second moiety is derived is selected from: diclofenac, SC560, valeryl salicylate, mofezolac, FR122047, celecoxib, ibuprofen, and ketoprofen. In some embodiments, the COX enzyme inhibitor is diclofenac.

In some embodiments, the opioid from which the first moiety is derived is selected from: naltrexone, buprenorphine, butorphanol, codeine, cyclazocine, cyclorphan, oxilorphan, dihydrocodeine, dihydromorphine, ethymorphine, hydromorphone, levallorphan, levorphanol, nalbuphine, nalmefene, nalorphine, naloxone, naltrexol, phenazocine, and pholcodine; and the COX enzyme inhibitor from which the second moiety is derived is selected from: diclofenac, SC560, valeryl salicylate, mofezolac, FR122047, celecoxib, ibuprofen, and ketoprofen.

In some embodiments, the opioid antagonist is naltrexone or naltrexol and the COX enzyme inhibitor is diclofenac.

In some embodiments, the compound includes a linker moiety. In some embodiments, the opioid antagonist and the COX enzyme inhibitor are linked by a linker moiety. In some embodiments, the linker moiety is cleavable. In some embodiments, the linker moiety is cleavable by hydrolysis and/or enzymatic digestion. In some embodiments, the linker moiety inparts improved aqueous solubility to the compound.

In some embodiments, the compound comprises a structure selected from a structure as set forth in FIG. 2.

The presently-disclosed subject matter further includes a method for treating a subject, including identifying a subject in need of treatment for a condition selected from the group consisting of pain, depression, narcotic dependence, alcohol dependence, amphetamine dependence, smoking dependence, and anabolic-androgenic steroid dependence; and delivering to the subject a therapeutically effective amount of a compound of the presently-disclosed subject matter.

In some embodiments, a method for treating a subject includes identifying a subject in need of treatment for a condition selected from the group consisting of pain, depression, narcotic dependence, alcohol dependence, amphetamine dependence, smoking dependence, and anabolic-androgenic steroid dependence; and delivering to the subject a therapeutically effective amount of a compound of the presently-disclosed subject matter, wherein following delivery to the subject, the compound is transformed into at least two active drug molecules. In some embodiments, the transformation is by hydrolysis and/or enzymatic digestion. The compound can be delivered in a variety of manners. In some embodiments, the compound is delivered transdermally.

In some embodiments, the compound can be transdermally delivered by microneedle, wherein the compound achieves improved duration of microporation-assisted delivery of the drug of interest (from which the first moiety of the compound is derived), as compared to the parent drug of interest (as administered independent from the compound including first and second moieties as described herein). In some embodiments, the improvement of duration of microporation-assisted delivery of the drug of interest (e.g., from a single patch) is an improvement of greater than 1, 2, 3, 4, 5, 6, or 7 days.

DESCRIPTION OF EXEMPLARY EMBODIMENTS

Figure 1:
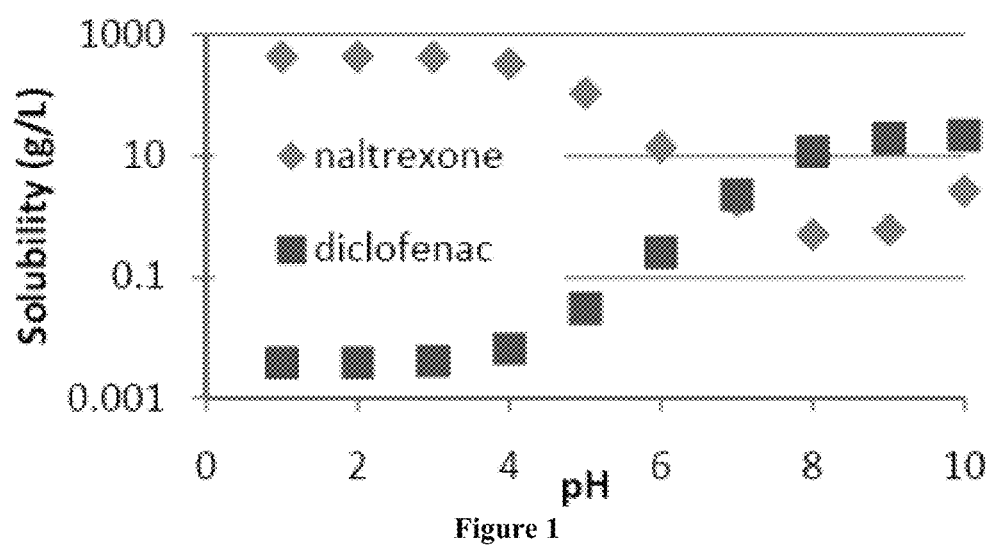
FIG. 1 is a graph showing solubility of naltrexone and diclofenac as a function of pH; pH 5 is the ideal value for topical formulation.

The presently-disclosed subject matter includes compounds including a first moiety derived from a drug of interest; and a second moiety derived from a cyclooxygenase (COX) enzyme inhibitor, wherein the first moiety is linked to the second moiety to form a single chemical entity.

Compounds of the presently-disclosed subject matter are sometimes referred to herein as codrugs. A codrug comprises two different drugs within a single chemical entity. The two drugs may be connected either directly or by means of a cleavable, biolabile covalent linker. Many diseases are treated by a combination of therapeutic agents that are co-administered in separate dosage forms. However; there are potential advantages in delivering the co-administered agents as a single chemical entity. One advantage is that often, when the two drugs are chemically linked together in the codrug structure, the resulting physicochemical and pharmacokinetic properties of the codrug are superior to those of the individual parent drugs.

The term "derived from" indicates that the first and second moieties of the compounds have a structure of a parent drug of interest and COX inhibitor that have been modified as is necessary to be connected to the remainder of the compound, while maintaining some or all of the activity associated with the parent compound, or while obtaining enhanced activity relative to the parent compound. For example, a moiety derived from a drug of interest and COX inhibitor can have the structure of the drug of interest and COX inhibitor, less a leaving group (e.g., less a hydrogen, less a hydroxyl, less a covalent bond, or less another leaving group) or including a connecting group, as will be apparent to one of ordinary skill in the art.

The compounds of the presently-disclosed subject matter provide for improved microneedle-enhanced delivery rates across skin, as well as an increase in the pore lifetime or duration of delivery. Without wishing to be bound by theory or mechanism, the cox inhibitor component of the compound allows for pores to remain open for a longer time period, allowing for improved delivery of the first moiety/drug of interest. In some embodiments, the first moiety is derived from a drug with a phenolic hydroxyl or hydroxyl group. In some embodiment, the first moiety is derived from an opioid. In some embodiments, the first moiety is derived from an opioid antagonist.

Exemplary first moieties of the compounds of the presently-disclosed subject matter can be derived from opioids including, but not limited to naltrexone, buprenorphine, butorphanol, codeine, cyclazocine, cyclorphan, oxilorphan, dihydrocodeine, dihydromorphine, ethymorphine, hydromorphone, levallorphan, levorphanol, nalbuphine, nalmefene, nalorphine, naloxone, naltrexol (including 6-beta naltrexol and 6-alpha naltrexol), phenazocine, and pholcodine, and other opioids known to those skilled in the art.

Exemplary second moieties of the compounds of the presently-disclosed subject matter can be derived from COX enzyme inhibitors including, but not limited to diclofenac, SC560, valeryl salicylate, mofezolac, FR122047, celecoxib, ibuprofen, ketoprofen, and other COX inhibitors known to those skilled in the art, including non-steroidal anti-inflammatory drugs (NSAIDs), COX-1 inhibitors and COX-1-specific inhibitors, and COX-2 inhibitors and COX-2-specific inhibitors.

In some embodiments of the compound, the opioid antagonist is naltrexone or naltrexol, and the COX enzyme inhibitor is selected from diclofenac, SC560, valeryl salicylate, mofezolac, FR122047, celecoxib, ibuprofen, and ketoprofen. In some embodiments of the compound, the opioid antagonist is naltrexone or naltrexol, and the COX enzyme inhibitor is diclofenac. In some embodiments of the compound, the opioid antagonist is naltrexol and the COX enzyme inhibitor is diclofenac.

In some embodiments, the compound has more than one first moiety derived from an opioid antagonist and/or more than one second moiety derived from a COX inhibitor, wherein each of the first moieties and each of the second moieties are independently selected (e.g., each of the more than one first moieties need not be derived from the same opioid antagonist and/or each of the more than one second moieties need not be derived from the same COX inhibitor.

In some embodiments, the opioid antagonist and the COX enzyme inhibitor are joined by a linker moiety or more than one linker moiety. The linker moiety(ies) can be a cleavable linker moiety(ies) such as ester, thioester, carbonate, carbamate, thiocarbamate, amide, thioamide, ureide, or any other suitable chemical moieties, providing that the chemistry is feasible. It will be recognized by the skilled artisan that desirable linker moieties can be bioconvertible or biolabile. In some embodiments the linker moiety(ies) is cleavable via hydrolysis or enzymatic digestion.

Figure 2A:
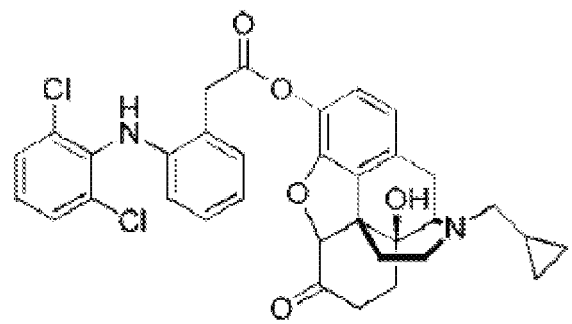
FIGS. 2A-2W are structures of exemplary embodiments of compounds of the presently-disclosed subject matter, where n is 1, 2, 3, or 4 in FIGS. 2C-2J, 2M, and 2N, and n is 4, 5, or 6 in FIGS. 2K and 2L.
Figure 2B:
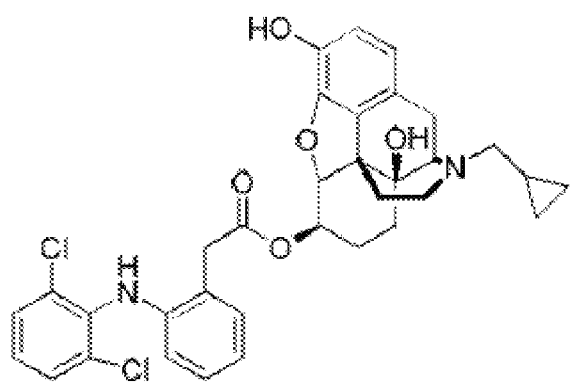
Figure 2C:
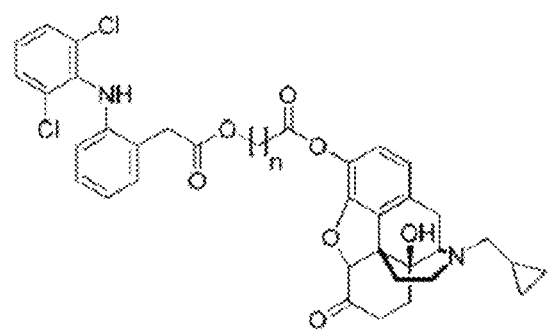
Figure 2D:
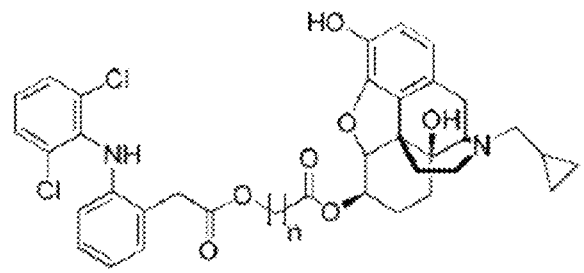
Figure 2E:
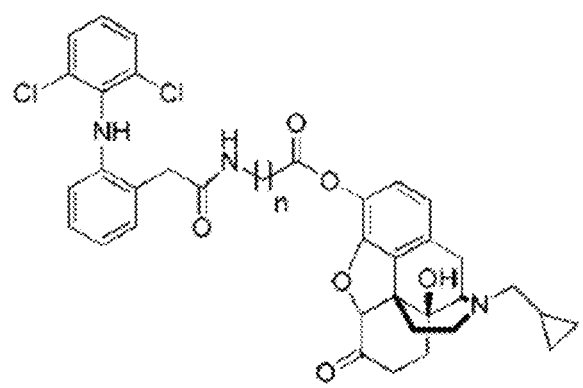
Figure 2F:
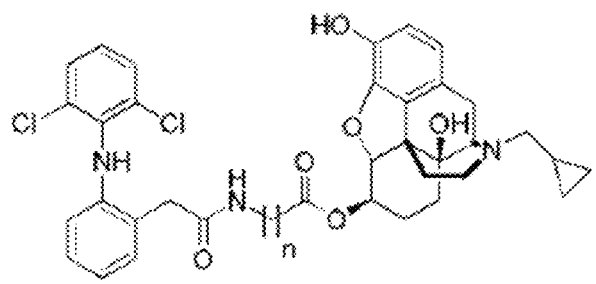
Figure 2G:
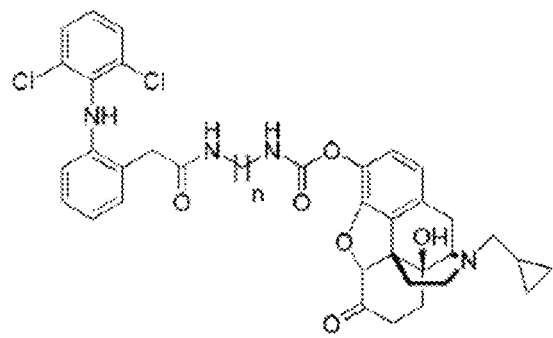
Figure 2H:
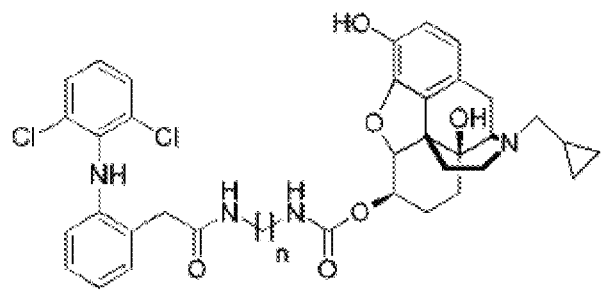
Figure 2I:
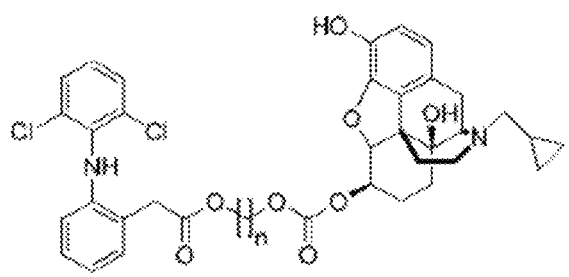
Figure 2J:
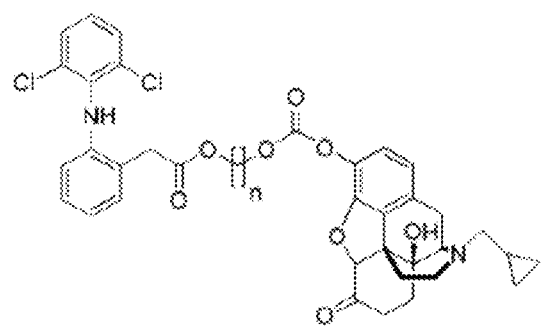
Figure 2K:
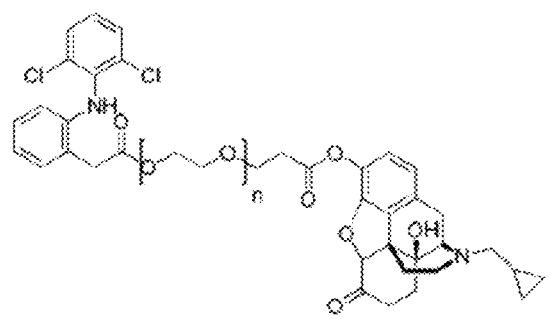
Figure 2L:
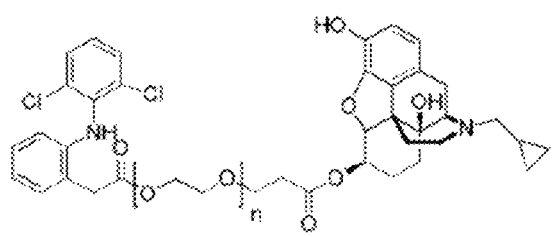
Figure 2M:
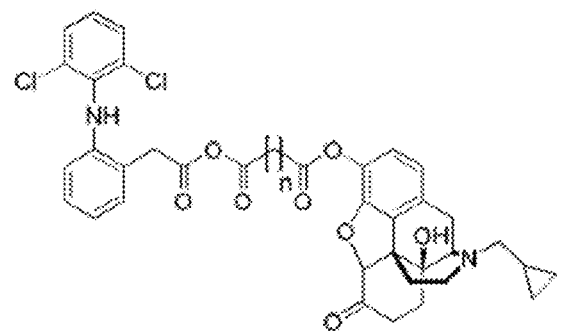
Figure 2N:
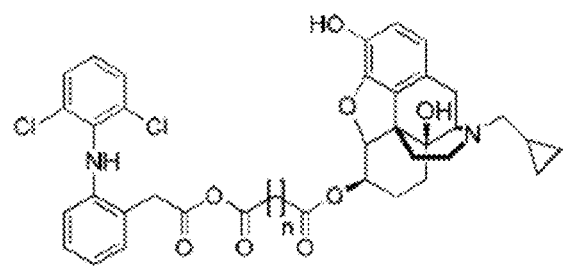
Figure 2O:
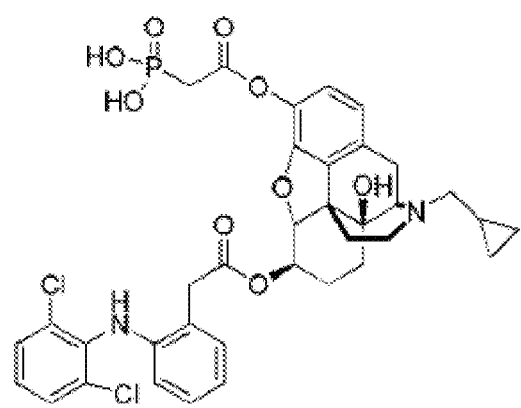
Figure 2P:
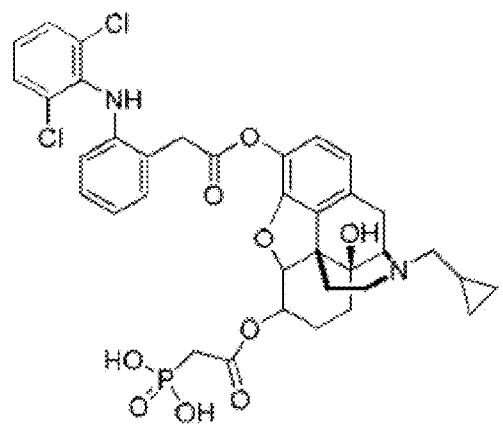
Figure 2Q:
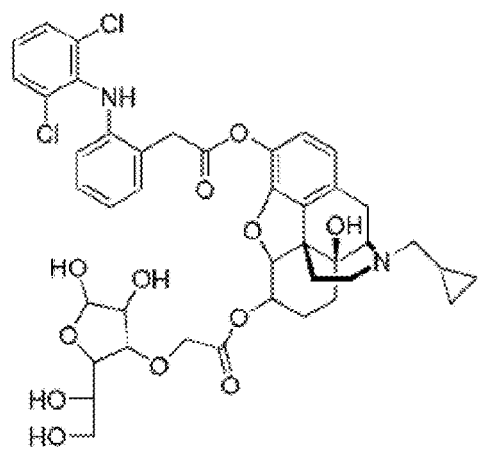
Figure 2R:
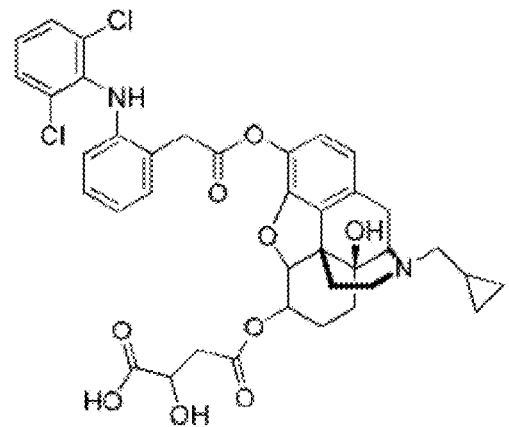
Figure 2S:
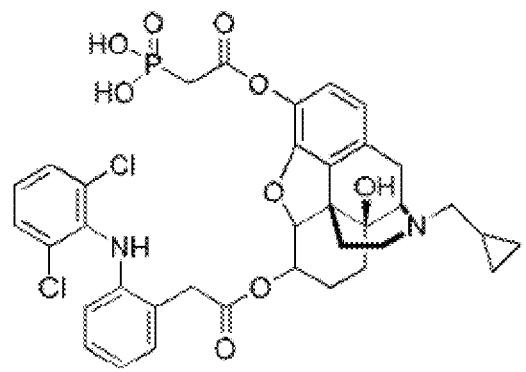
Figure 2T:
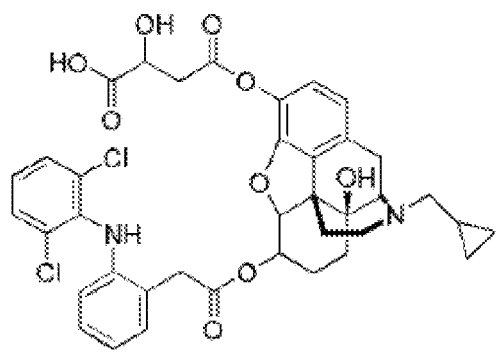
Figure 2U:
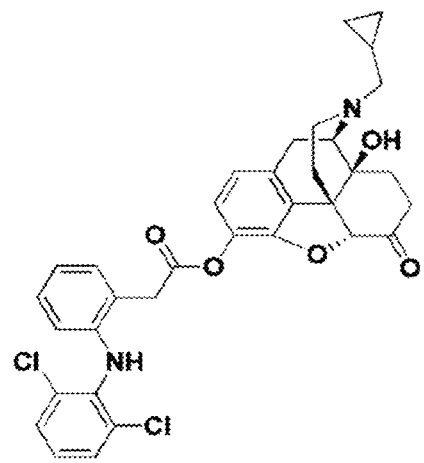
Figure 2V:
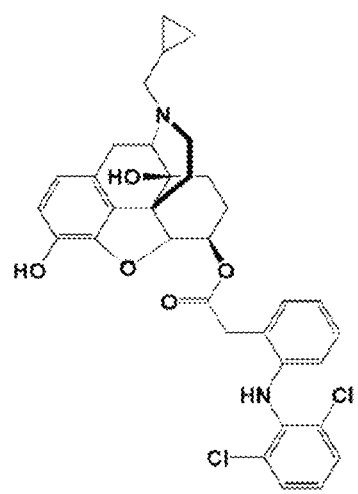
Figure 2W:
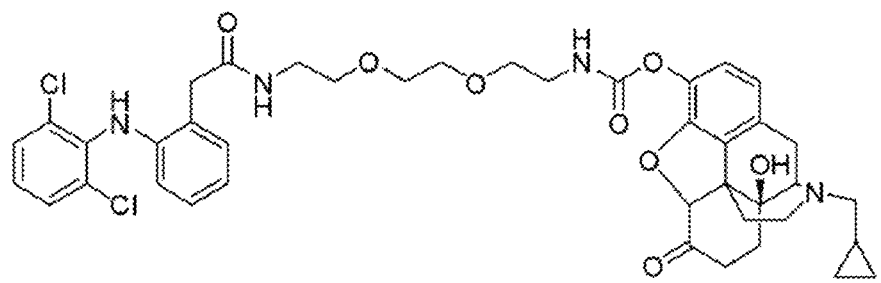
Figure 3:
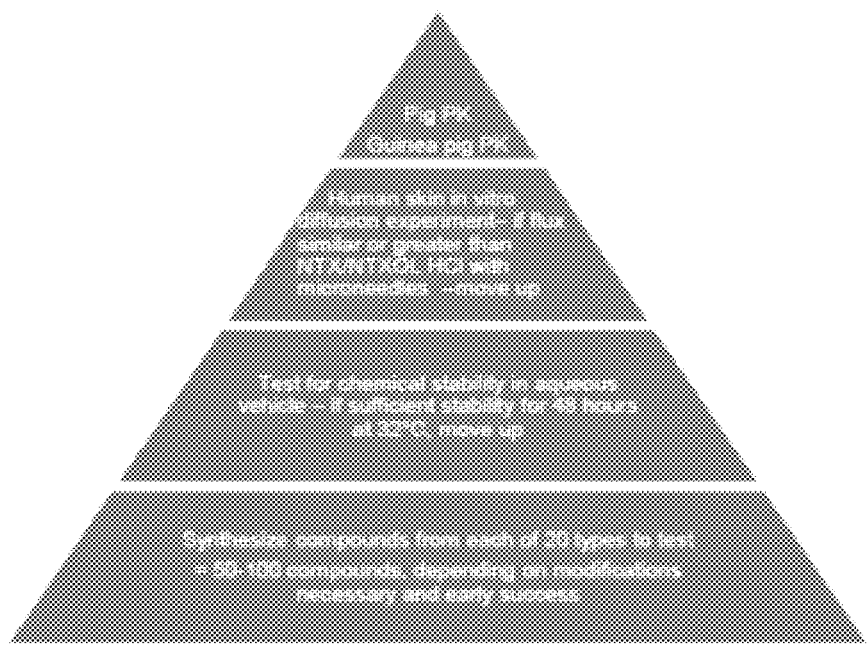
FIG. 3 describes the specific decision making for compounds of the presently-disclosed subject matter, as described in the present Examples.

Exemplary compounds of the presently-disclosed subject matter are set forth in FIGS. 2A-2W.

The presently disclosed subject matter also includes methods of treating a subject for conditions including pain, depression, and substance dependence, including narcotic dependence, alcohol dependence, amphetamine dependence, smoking dependence, and anabolic-androgenic steroid dependence. As used herein, dependence is inclusive of addiction and is inclusive of any disorder associated with dependence and/or addiction; as such, alcohol dependence, for example, is inclusive of alcohol abuse and alcoholism.

In some embodiments, a method of the presently-disclosed subject matter includes identifying a subject in need of treatment for a condition selected from the group consisting of pain, depression, narcotic dependence, alcohol dependence, amphetamine dependence, smoking dependence, and anabolic-androgenic steroid dependence; and delivering to the subject a therapeutically effective amount of a compound of the presently-disclosed subject matter. Without wishing to be bound by mechanism, following delivery to the subject, the compound is transformed into at least two active drug molecules.

Subjects who can benefit from the methods of the present invention include, for example, mammals, such as humans, particularly humans who are suffering from pain, depression, and/or substance dependence.

"Treatment" or "treating," as used herein, refers to complete elimination as well as to any clinically or quantitatively measurable reduction in condition for which the subject is being treated. The methods of the presently-disclosed subject matter include delivering a therapeutically effective amount of the compound. A "therapeutically effective amount," as used herein, refers to an amount, determined by one skilled in the art, sufficient for treating the condition for which the subject is being treated.

The compound can be delivered to a subject transdermally, intravenously, orally, buccally, sublingually, by topical creams, subdermally, as a sustained release depot, ophthalmically, intranasally, aurally, by inhalation, rectally or vaginally.

In some embodiments, transdermal delivery is used. In an exemplary method for transdermal delivery of the compound, the steps comprise contacting a section of skin with the compound and biotransforming the compound into two drugs by skin enzymes or by hydrolysis of the compound in the skin. A transdermal patch comprising a suitable substrate and a layer of the compound can be employed to deliver the compound to the skin.

The compound can be administered as a pharmaceutical composition comprising pharmaceutically acceptable carriers, diluents, and/or excipients, which are vehicles commonly used to formulate pharmaceutical compositions for animal or human administration. The carriers, diluents and/or excipients are not intended to have biological activity themselves, and are selected so as not to affect the biological activity of the compound and any other active agent(s). A pharmaceutically acceptable carrier, diluent, and/or excipient as used herein includes both one and more than one such carrier, diluent, and/or excipient. Examples include but are not limited to distilled water, saline, physiological phosphate-buffered saline, Ringer's solutions, dextrose solution, and Hank's solution. Depending upon the manner of introduction, the compound can be formulated as, for example, a sterile injectable formulation comprising aqueous solutions and/or suspensions containing the active materials in admixture with suitable carriers, diluents, and/or excipients.

The concentration of compound, the formulation (i.e., a formulation that is therapeutically effective to the subject to which it is administered) and the dose administered can be readily determined by a person of ordinary skill in the art. Typically, dosages used in vitro and in animal models, such as in the experiments provided in the present application, can provide useful guidance in the amounts useful for in vivo administration.

The compound can be applied to the skin as a topical cream, salve, ointment, gel, or other topical formulation; and/or by using delivery devices such as bandages, occlusive bodies, patches, and/or the like. The area of skin to which the compound is applied can optionally be pre-treated with microneedles or other microporation devices, as are known to those of ordinary skill in the art.

Illustratively, a composition of the compound that is applied to the skin can be formulated as a topical cream, salve, gel, or ointment. The topical formulations can include inert diluents and carriers as well as other conventional excipients, such as wetting agents, preservatives, and suspending and dispersing agents. In addition to the above, generally non-active components, topical formulations containing compound can further include other active materials, particularly, active materials which have been identified as useful in the treatment of the condition for which the subject is being treated, for example substance addiction, and which can usefully be delivered transdermally to the subject. For instance, such other active materials can include acamprosate, disulfiram, topiramate, sertraline, rivastigmine, citalopram, and doxepin. The topical formulation can be applied directly to the skin and then optionally covered (e.g., with a bandage of gauze) to minimize the likelihood of its being disturbed. Alternatively, the topical formulation can be coated on the surface of a bandage, gauze, etc., and the bandage, gauze, etc. can then be applied to the skin of the subject such that the topical formulation is in direct contact with the subject's skin.

Alternatively, the compound can be delivered transdermally to the subject by formulating compound into a bandage, pad, or other type of patch which can be applied to the subject's skin.

Illustratively, matrix-type transdermal patches, in which the compound is disposed in an adhesive matrix, can be employed. The matrix-type transdermal patch can further include other active materials for transdermal delivery to the subject with the compound. Suitable adhesives for use in such matrix-type transdermal patches include polyisobutylenes, acrylates, silicone, hydrogels, and combinations thereof. Still other patches suitable for use in the practice of the present invention are known to those of ordinary skill in the art.

In another illustrative embodiment, the bandage, pad, or other type of patch can be one which is capable of controlling the release of the compound such that transdermal delivery of the compound to the subject is substantially uniform and sustained over a period of at least 12 hours, such as at least 24 hours, at least 48 hours, at least 3 days, at least 4 days, at least 5 days, at least 6 days, and/or at least 7 days. Such a bandage, pad, or other type of patch which can be used in the practice of the method of the present invention can take the form of an occlusive body. In practice, the occlusive body which includes the compound is positioned on the subject's skin under conditions effective to transdermally deliver the compound to the subject's skin.

In some embodiments, the methods of the presently-disclosed subject matter can make use of transdermal delivery using microneedles. The microneedle strategy suitable for use in the presently-disclosed subject matter is not particularly limited, but includes any microneedle strategy that can be employed to facilitate the transdermal delivery of compounds described herein.

As used herein, the term "microneedles" refers to a plurality of elongated structures that are sufficiently long to penetrate through the stratum corneum skin layer and into the epidermal/dermal layer, yet are also sufficiently short to not activate nerve endings and cause pain.

Various microneedles that can be employed to facilitate transdermal delivery of compounds of the presently-disclosed subject matter are described in printed publications and are known to those of ordinary skill in the art. Suitable microneedles have been fabricated from many materials, including silicon, metals, and polymers.

The microneedles can be solid or hollow. If solid microneedles are used, channels can be made by poking the skin with a microneedle array, followed by removal of the needles and then application of the drug. Alternatively, the solid microneedles can be inserted and left in the skin, allowing diffusion through the gaps between the microneedles and the surrounding tissue. Solid microneedles can also be coated with the compound prior to insertion into the skin. Alternatively, microneedles containing a hollow bore can be used to transport drugs through the interior of the needles by diffusion or pressure-driven flow. Hollow microneedles can act as mini hypodermic injection needles.

In some embodiments, the microneedles can be used to create a microneedle-treated site prior to applying the compound to the microneedle-treated site. As noted above, the microneedles can be inserted and left in the skin. In some embodiments, a microneedle array comprised of solid microneedles can be used to increase skin permeability by inserting the microneedles into the skin and then removing the microneedles to create a microneedle-treated site prior to applying the compound to the microneedle-treated site. Optionally, the microneedles can be repeatedly inserted and removed, at the same site. Typical microneedle arrays comprise 15-200 microneedles, but can include any number of microneedles that is desired.

The microneedles can be inserted and removed to create a microneedle-treated site on the subject's skin under conditions effective to transdermally deliver the compound upon application of the compound. Such conditions can include, for example, positioning the microneedle-treated site on a portion of the subject's skin which is not covered with hair, and/or shaving the hair from the selected portion of the subject's skin.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include prophetic descriptions, and/or compilations of data and information that are representative of data and information gathered at various times during the course of development and experimentation related to the present invention.

EXAMPLES

Example 1

An objective of the exemplary studies described herein include improvement of drug therapy for opioid, smoking, methamphetamine, alcohol and other relevant addiction recovery by creating transdermal dosage form with longer intervals between dosing, e.g., at least 7-day (once-a-week dosing).

Alcoholism and drug addiction lead to major health-related problems and societal costs for people in the United States and the rest of the world as well. Therefore, research and development for improved pharmacologic treatments for drug and alcohol abuse are very important. Naltrexone (NTX), an opioid antagonist, is currently prescribed in oral tablet and injectable form to help maintain opioid addicts in a drug free state. Most recently, naltrexone has been indicated as an adjunct in the treatment of alcohol dependence, as well as reported to reduce alcohol craving in certain alcoholic populations. Unfortunately, postmarketing reports of serious injection site reactions (cellulitis, abscess, and necrosis) have recently required patient warning updates for the 30-day NTX depot injection. Additionally, high oral doses that may be needed for therapeutic effect in addicts can cause hepatotoxicity. Substantial clinical evidence exists for the benefits of NTX treatment in smoking cessation, especially in women (Epperson et al., 2010; Roche et al., 2010; Shaw and al'Absi, 2010; Toll et al., 2010). Very intriguing clinical trial data has also been observed in amphetamine dependent individuals, which is especially important as methamphetamine dependence has no FDA-approved treatment options (Grant et al., 2010; Haggkvist et al., 2009a; Haggkvist et al., 2009b; Karila et al., 2010).

Preclinical data also exists that suggests that NTX may benefit anabolic-androgenic steroid dependent people (Kanayama et al., 2010a; Kanayama et al., 2010b). Treatment with NTX in the 90's and early 2000's produced variable success rates in addicts; however, current clinical NTX therapy is being optimized based on human pharmacogenetic data (Barr et al., 2010; Fortin et al., 2010; Ray et al., 2010a; Ray et al., 2010b). Transdermal delivery of naltrexone is desirable for addicts and alcoholics in order to help reduce side effects associated with oral (bypass first-pass effect) and injectable therapy and improve compliance. Naltrexone itself does not have the essential physicochemical properties that would allow a therapeutic dose of the drug to cross the human skin barrier. Microneedle-enhanced transdermal delivery is an efficient and painless method for increasing the skin permeation of many drugs, including naltrexone (Prausnitz, 2004; Wermeling et al., 2008). The major limitation of microneedle-enhanced delivery is that the micropore lifetime only allows delivery of drug for two to three days (Banks et al., 2010; Milewski et al., 2010; Wermeling et al., 2008).

Diclofenac and other relevant cyclooxygenase (COX) enzyme inhibitors can prolong the lifetime of the micropores to seven days, allowing for once a week patch dosing, the transdermal delivery ideal goal (Banks et al., 2011). Many of the COX inhibitors are weak acids, and naltrexone and many other desirable transdermal drugs are weak bases. It is difficult to formulate high concentrations of a weak base and a weak acid in the same system, due to chemical stability and solubility issues. The present inventors disclose herein compositions (sometimes referred to herein as codrugs), which are covalently linked yet biolabile combinations of an opioid antagonist (e.g., naltrexone) and a COX inhibitor (e.g., diclofenac), in order to make a therapeutically successful once a week drug delivery system. It is contemplated that codrugs of naltrexone in combination with microneedle treatment will provide a 7-day therapeutic transdermal delivery rate of naltrexone, and that these codrugs will make excellent research tools for investigating quantitative structure permeability relationships (QSPR) for transdermal flux and optimization of flux and micropore lifetime in combination with microneedle enhancement. These codrugs/microneedles should improve naltrexone delivery rates across the skin because of optimized physicochemical properties for faster diffusion.

A series compounds (FIG. 2) were designed to elucidate fundamental QSPRs for microneedle-enhanced transdermal flux optimization and subsequent bioconversion rates. Characterization of the physicochemical properties of the codrugs, including molecular volume, lipophilicity, hydrogen-bonding potentials, melting points, heats of fusion, hydrolysis kinetics, and solubilities in select solvents is contemplated. The present inventors also contemplate measuring the drugs' penetration, concurrent bioconversion, and COX inhibitor deposition in skin in vitro with microneedle use. Also contemplated is characterization of the pharmacokinetics of the compounds in animals (e.g., guinea pigs and Yucatan miniature pigs in vivo, and humans) with microneedle use. Correlation of the in vitro data with the in vivo model will aid in the creation of a reliable QSPR database that is useful to determine relative efficacy of compounds for clinical use. The studies will incorporate a parallel pharmacodynamic (micropore closure) and drug delivery/pharmacokinetic approach to identify novel codrug treatments for significant clinical problems, such as opiate, smoking, methamphetamine and alcohol addiction.

As noted herein naltrexone (NTX) is an opioid antagonist that is currently used to help maintain opioid addicts in a drug-free state. Most recently, naltrexone has been indicated for use in treatment of other substance dependencies, e.g., alcohol dependence, including use to reduce alcohol craving in certain alcoholic populations (Garbutt, 2010; Gueorguieva et al., 2010; Martinotti et al., 2010; Morley et al., 2010; O'Malley, 1996; O'Malley et al., 1992; Soyka and Rosner, 2010; Volpicelli et al., 1992; Zarkin et al., 2010). Pharmacogenetic analysis has been shown to improve NTX treatment outcomes in clinical trials for alcoholism (Barr et al., 2010; Fortin et al., 2010; Kranzler and Edenberg, 2010; Kranzler et al., 2000; Ray et al., 2010a; Ray et al., 2010b). NTX Hydrochloride is currently commercially available in the United States as a 50-mg oral tablet (ReVia®), as well as in generic form. Naltrexone undergoes extensive first-pass metabolism and has oral bioavailability estimates ranging from five to forty percent (PDR). Naltrexone is also a hepatotoxin that has the capacity to cause dose-related hepatocellular injury. This hepatotoxicity limits dosage increases in those addicts who may benefit from more than a 50-100 mg per day oral dose. Transdermal delivery would circumvent these liver-related problems by allowing lower doses to be used, because first-pass metabolism is bypassed. Certainly, the ability to decrease the drug dosage would benefit the already hepato-compromised alcoholic or narcotic addict. Many of the adverse effects seen with ReVia® oral therapy (abdominal pain, constipation, nausea, and vomiting) could also be reduced by transdermal therapy. Compliance, the major problem with addict recovery pharmacological intervention, is likely improved when side effects are reduced and drug doses are adequate to reduce craving (O'Malley, 1996; O'Malley et al., 1992). One goal of this research is to enhance the therapeutic value of naltrexone by reducing side effects and improving addict compliance with transdermal delivery that allows for dosing of at least about 7 days. Several once-a-week transdermal patches are on the market and are very popular.

The major problems with addict naltrexone use are motivation and compliance, which have prompted the development of 30-day depot dosage forms (Garbutt et al., 2005; Kranzler et al., 2000). The depot dosage form (Vivitrol, approved by the FDA in the summer of 2006) has been shown to be effective in clinical trials with opiate addicts and alcoholics, which bodes well for the patch, as the plasma drug concentration profiles would be similar after depot injection or patch treatment. In contrast to depot dosage forms, transdermal systems offer a patient freedom from injections (a 380 mg NTX as 1.1 g microsphere intramuscular injection), surgical implantations, and the healthcare costs associated with implant dosing. Injection site reactions are one of the most common Vivitrol adverse events.

Another advantage of transdermal dosing is the ability to terminate the drug dose input at any time by simply removing the patch. The process of terminating drug input from the depot injection requires surgical removal of microspheres from the muscle, which might be necessary if a patient requires opiate treatment for pain in an emergency situation that occurs within the 30-day window where plasma levels of naltrexone are released. A transdermal patch provides sustained-release of a drug for a maximum of about one week. Once-a-week dosing is certainly more desirable than the three to seven times a week dosing of the currently available ReVia®. The transdermal patch delivery system suits the addict population well, being similar to the patch-wearing population of nicotine addicts. A transdermal system that delivered a therapeutic dose of naltrexone into the body for one week would certainly be consistent with a weekly visit to an addict recovery clinic or probation officer. As compliance is the major concern in nonmotivated criminal addicts, use of an adhesive that sticks to the skin only once could be a helpful clue for a probation officer looking for the noncompliant addict. This could deter an addict from removing his/her patch during the week, knowing that punishment for showing up with a non-stick patch would be likely.

A very promising use of a transdermal NTX system is as an adjunct in the treatment of alcohol dependence. Transdermal delivery of the potential hepatotoxin naltrexone will bypass first-pass liver metabolism and also decrease gastrointestinal side effects. A relatively motivated alcoholic would certainly want the ease of use and reduction of side effects possible with transdermal delivery. In fact, compliance has been a critical issue in the response of alcoholics to naltrexone therapy in recent clinical trials (Volpicelli et al., 1997). Alcohol use has been shown to decrease by about one-half in adult alcoholics taking naltrexone (Pettinati et al., 2010; Volpicelli et al., 1997). Additionally, there is one case report of an adolescent male that describes 30-day abstinence during naltrexone alcohol-dependence treatment. The prevalence rate of adolescent alcohol dependence appears to be about four to ten percent, according to some self-reported epidemiological studies. Thus, transdermal delivery of naltrexone may also prove useful in the adolescent alcohol-dependent population, as well as in adults.

Naltrexone itself does not have the essential physicochemical properties that would allow a therapeutic dose of the drug to cross the human skin barrier. Prodrugs contain covalently bound chemical moieties added to a drug to make it more permeable, but these prodrugs are rapidly bioconverted back to the active parent compound after dosing or absorption. A codrug contains two active drug molecules covalently linked together to improve the delivery or other properties of one or both drugs (Kiptoo et al., 2006; Kiptoo et al., 2008; Strasinger et al., 2008). In this case, the acid functionality is being removed (temporarily masked) from one of the drugs by forming a codrug so that the weak acid COX inhibitor and the weak base NTX can be combined at high concentrations in one dosage form without stability or solubility incompatibility issues (FIG. 1). The naltrexone delivery rate will be enhanced with codrugs designed to optimize microneedle-assisted delivery for NTX flux as well as micropore lifetime.

Verification of codrug NTX delivery enhancement with an applicable in vitro/in vivo transdermal delivery correlation will help identify the most promising codrug for eventual human use. This validation of in vitro/in vivo correlation will be especially important in microneedle-assisted delivery, where optimal and efficient testing methods are just being developed for this new and rapidly growing area of drug delivery. Increased understanding of the quantitative structure-permeability relationships (QSPRs) for transdermal codrug flux and concurrent bioconversion in vivo will be attained by statistically comparing calculated codrug physicochemical parameters, experimentally-derived physicochemical parameters, and diffusion study data. This way the data gathered here can be applied to the design of other transdermal codrugs for use with microneedle-assisted delivery.

Skin Permeation: The skin consists of two major layers, the outer epidermis and the inner dermis. The stratum corneum, the outermost 10-15 μm of the epidermis, is responsible for the skin's excellent diffusional resistance to the transdermal delivery of drugs. Most of the skin's enzymatic activity lies in the basal cell layer of the viable epidermis. Many researchers (Potts et al., 1997; Potts and Guy, 1992; Roberts and Sloan, 1999) have developed skin permeability relationships based on the physicochemical parameters (molecular weight, molecular volume, lipophilicity, hydrogen-bonding potentials, polarity, etc.) of skin penetrants. In the proposed project, these useful permeability models will be correlated with transdermal codrug diffusion, while taking into account complications of concurrent bioconversion of the codrug.

Transdermal Prodrugs and Codrugs (Mutual Prodrugs): Studies performed by R. J. Scheuplein et al. in the 1960's spurred pharmaceutical scientists to make use of new information concerning passive permeability and metabolism properties of the skin. Since transport is a highly restricting factor to successful topical use of drugs and since it is the physical properties of a drug that largely determine the upper limit to transport, attention was soon focused on manipulating the physical properties of drugs to improve delivery. Models for evaluating transdermal prodrug delivery began to appear in the pharmaceutical literature in the late 1970's (Yu et al., 1979). Over the last thirty years some other scientists have described possible transdermal prodrug delivery for drugs such as fluorouracil, naproxen, acyclovir, indomethacin, morphine, estradiol, and theophylline. A few people have written comprehensive reviews about transdermal prodrug delivery, but this usually appears as a minor subject in broadly based articles on prodrugs.

One transdermal delivery review incorporated codrugs and prodrugs (Strasinger et al., 2008). Prodrugs specifically to be used with microneedle-enhanced transdermal delivery are also not readily available in the literature yet (Milewski et al., 2010a; Milewski et al., 2010b). After three decades of transdermal prodrug/codrug delivery study, the field still seems relatively young with relatively small amounts of literature published in the area, and no products on the market. Synthesizing specific codrugs with varying physicochemical properties and systematically studying how the transport and bioconversion of these codrugs are affected by these physicochemical properties will give us a greater database of transdermal codrug knowledge. Publication of the results of these carefully controlled in vitro and in vivo diffusion experiments with corresponding statistical relationships to physicochemical codrug properties (QSPR) will greatly add to the prodrug/codrug literature. The ability to choose the design of a successful prodrug/codrug based on simple calculated and experimentally measured parameters could save the pharmaceutical chemist valuable time and effort.

With skillful formulation and addition of skin penetration enhancers, some borderline delivery candidates can be made into transdermally useful therapeutic agents. Penetration enhancers are chemicals that alter the structure of the stratum corneum temporarily in order to open up a pathway for faster diffusion of drugs through skin. A major disadvantage to penetration enhancer use in transdermal delivery systems is the potential for skin irritation and allergic reaction. Skin irritation is a very common reason why many topical and transdermal dosage forms do not make it to the market. A major advantage of using transdermal prodrugs/codrugs with prompt bio-activation is that their skin irritation and allergenic potential should only mirror the profile of the parent drug(s), without the possible added toxicities of penetration enhancers.

Successful delivery of NTX has been shown in humans using microneedle enhancement for two to three days (Wermeling et al., 2008). Use of microneedles with optimized codrugs will enable naltrexone delivery rates to increase multiple-fold over passive delivery patches, without irritating enhancers, and with the added advantage of improving the delivery duration from one patch to 7 days, the optimal transdermal dosing goal.

Therapeutic Goal: From the standpoint of making NTX transdermally useful, the present inventors contemplated a need for a temporary form of NTX with optimized properties to substantially increase its flux (from 3 nmol/cm$^2$/hr to about 12-90 nmol/cm$^2$/hr). The most recent depot injection clinical trial for alcohol dependence indicates that the required flux would be 34-68 nmol/cm$^2$/hr from a 20 cm$^2$ patch (Garbutt et al., 2005). If the patch size is doubled, the required flux rate would be reduced by one half. With microneedle treatment alone, the present inventors found that NTX could be delivered at the lower end of the therapeutic range for opiate receptor blockade in humans, 2 ng/mL (Verebey et al., 1976).

The main therapeutic goal is to achieve a substantial increase in the flux of the codrug across the skin to reach effective levels in the body. This codrug would also supply an equimolar dose exposure to diclofenac (or other future COX inhibitors of choice). The minimum daily effective systemic therapeutic dose of diclofenac is 75 mg×0.55 oral bioavailability (Micromedex 1.0), or 41 mg per day. This translates to a required systemic delivery rate of 270 nmol/cm$^2$/hr from a 20 cm$^2$ patch, which is several-fold higher than the required systemic NTX flux.

Therefore, since the required NTX flux is the target for systemic therapy, the diclofenac absorbed would be subtherapeutic because its use in the codrug is only to deposit into the skin and maintain the pore lifetime through a localized effect. As diclofenac is a potent COX inhibitor, many other COX inhibitors could be used that would have a local effect and very little systemic effect.

6-β-Naltrexol (NTXOL) is the major metabolite formed by rapid reduction of NTX in humans (Cone et al., 1974) and in several other animal species, including guinea pigs (Valiveti et al. 2004). NTXOL may contribute to the therapeutic action of NTX in drug and alcohol dependence due to its significant plasma concentrations (Ferrari et al., 1998; Meyer et al., 1984; Wall et al., 1981) and longer terminal half life (McCaul et al., 2000a; McCaul et al., 2000b; Rukstalis et al., 2000; Wall et al., 1981) in humans compared to NTX. The NTXOL half-life ranged from 7.5 to 13 hours compared to 2-10 hours for NTX in these human subjects.

Additionally, NTXOL exerted a 4-9 times longer duration of action than NTX in different animal model experiments involving rats and mice. NTXOL is also an opioid antagonist with a similar affinity for the opioid receptors but with a lower potency than NTX in in vivo studies. However, the lower potency can be expected to be compensated by the presence of a much higher plasma concentration, suggesting that NTXOL might contribute a major role in the efficacy of NTX.

Recent studies have provided evidence that NTXOL may be of future relevance with respect to treatment of alcoholics as well. A preclinical study by Stromberg et al. showed that when given alone, NTXOL reduced alcohol consumption in rats in a dose-dependent manner. This was also confirmed in a second study (McCaul et al., 2000a; McCaul et al., 2000b). In addition, serum concentrations of NTXOL have been shown to be associated with reductions in number of drinks per month (O'Malley et al., 1992) and with potentially important negative subjective effects of alcohol in humans (McCaul et al., 2000a; McCaul et al., 2000b). In a randomized, double-blind clinical trial of NTX, subjects with a NTXOL level of more than 40 ng/ml did not experience an alcohol relapse (O'Malley et al. 1992), indicating that the relapse rate might be lower in patients treated with NTXOL. In addition, since NTXOL is mainly excreted through the renal route, it would be a safer alternative than NTX in hepato-compromised patients. All this indicates that NTXOL would be a useful therapy in drug addiction and alcoholism. Thus, the present inventors contemplate analogues of NTXOL for transdermal delivery, and consideration of the present inventors' codrug designs with NTXOL, to see if significant flux enhancement for this promising drug can be achieved (Paudel et al., 2005).

Microneedle Enhancement: Microneedle delivery is in its infancy stages of development for transdermal drug delivery, but the microelectromechanical systems (MEMS) class that microneedles stemmed from is a multibillion dollar market (McAllister et al., 2003). While microneedle insertion for transdermal drug delivery is new, it has shown promising results that show increased drug permeation; it is also a relatively painless drug delivery procedure (Kaushik et al., 2001). There are currently many other devices on the market, such as the ImplaJect™, Luer-Jet™, Iject® and Mini-Ject™, to deliver therapeutics systemically by needle-free injection. The overriding problems associated with these models are that they are costly to produce, require medical supervision for application, and importantly are not pain-free (Furness).

The microneedle would, on the other hand, cost much less to produce and purchase, require no office visit for application, and would be pain-free. Initial studies with microneedles have shown significant increases in the permeation of large molecules such as insulin (McAllister et al., 2003). The design of the microneedle is based on the composition of skin, because it must pass through the stratum corneum (10-15 μm) and into viable epidermis or dermal layers. In theory, the microneedle must only be long enough to pass through the first 15 μm of skin, but most microneedles are significantly longer. It is pertinent that a microneedle works to produce a significant aqueous channel through the epidermis so that continual drug delivery through this channel can occur before reversal (channel closing) is observed.

Examples of microneedle systems include BioValve's Micro-Trans™ microneedle array patch and 3M's Micro-structured Transdermal Systems (MTS). Several microneedle systems are in late-stage clinical trials. No codrugs have been proposed for use in connection with microneedle systems heretofore. In order to obtain the fastest drug delivery rates possible, optimization of codrug solubility, hydrogen bonding, and bioconversion rates will need to be completed.

In order to increase understanding of the QSPRs for transdermal codrug flux and concurrent bioconversion, one should start with the basics. The original 3-alkyl-ester, carbonate, and carbamate prodrug series for passive transdermal permeation served as the first building block in the design of better prodrugs (Pillai et al., 2004; Stinchcomb et al., 2002; Vaddi et al., 2009; Vaddi et al., 2005). This newly proposed microneedle-enhancement project provides a validated methodology of studying the effects of a simple and relatively stable skin esterase enzyme system on di-conjugation of the NTX molecule, to determine if significant enhancement is achieved over and above the enhancement seen with the mono-conjugated codrugs of NTX. The precise balance among lipophilicity, hydrophilicity, and metabolic bioconversion needs to be found for these codrugs, in order to maximize NTX flux rates across the skin and optimize COX inhibitor deposition into the skin simultaneously. Different polar and/or hydrophilic codrugs with varying properties will be especially suitable for the microneedle flux optimization (Banks et al., 2010; Banks et al., 2008), as diverse prodrug forms are known to significantly change absorption rates of injectable drugs, if one considers microneedle delivery to be a micro-injection.

There are currently no transdermal prodrug, codrug (mutual prodrug), or microneedle products on the market. The present inventors contemplate the following innovative features in connection with embodiments of the presently-disclosed subject matter.

Microneedles—carefully controlled models for transdermal delivery candidate selection, formulation, and micropore lifetime optimization will be evaluated using the "poke and patch" technique for systemic drug delivery. Most prior research in microneedle-assisted transdermal delivery has been for vaccines, biodegradable microneedles or coatings for very potent drugs, or in optimization of needle engineering. Currently, the present inventors' human microneedle NTX pharmacokinetic study is the only published report in this area using the "poke and patch" technique (Prausnitz and Langer, 2008; Wermeling et al., 2008). There is also an ongoing clinical trial for microneedle-assisted delivery of parathyroid hormone and a human proof of concept study for insulin delivery using hollow microneedles (Prausnitz and Langer, 2008).

Transdermal codrugs—carefully controlled design, synthesis and optimization of codrug structures based on chemical stability, enzymatic stability, and solubility. Few examples exist in the literature concerning optimization and utility of transdermal codrugs (Cynkowski et al., 2008; Kiptoo et al., 2006; Kiptoo et al., 2008; Strasinger et al., 2008).

Micropore lifetime—carefully optimized pharmacokinetic evaluation of micropore lifetime in order to further evaluate the effect of diclofenac and potentially other COX inhibitors. Previous studies on micropore lifetime have used many other visualization evaluation techniques (Kalluri and Banga, 2009), but only a few have examined pharmacokinetic analysis (Banks et al., 2010; Banks et al., 2011). Pharmacokinetic evaluation of micropore lifetime is the most useful and realistic applied method of evaluation. Drugs that are targets for microneedle-assisted delivery could impede or enhance the micropore closure rate, depending on their mechanisms of action. Additionally, very few reports occur in the literature describing ways to delay the micropore closure, so this in itself is an extremely unique aspect of this project (Banks et al., 2011; Milewski et al., 2010a).

Transdermal codrugs specifically for microneedle-assisted delivery—the overall goal of the project is something that has never been done before. The present inventors' research has shown some of the important aspects of what type of prodrug/drug is best for microneedle-assisted transdermal delivery (Banks et al., 2010; Banks et al., 2008; Milewski et al., 2010a; Milewski and Stinchcomb, 2010; Milewski and Stinchcomb, 2011; Milewski et al., 2010b), but the addition of the codrug that can have optimized delivery rates as well as duration is very new in drug delivery research.

Development of an improved 7-day transdermal system for NTX—this would improve patient compliance and the side-effect profile, as the depot injection and tablet have many drawbacks. The translational goal of the research is to develop an improved dosage form for naltrexone delivery for addicts and alcoholics. After the proof-of-concept research is complete, preclinical toxicology tests could be completed, an IND filed, and a Phase I clinical trial could begin at the end of three years. By this time, other microneedle systems should be on the market, so the primary regulatory hurdle would be the safety and efficacy of the codrug itself. Seven day transdermal patches on the market are very popular products.

Exemplary Compounds.

Synthesis and testing of the compounds of FIGS. 2A and 2B is now described, and contemplated with regard to other compounds in FIG. 2. The detailed synthetic methods are in the Synthetic Schemes provided hereinbelow. These two compounds have an ester linking naltrexone or naltrexol to diclofenac. The chemical stability half-life of Compound 2A in buffer (skin pH 5.0 and skin surface temperature 32° C.) was around 4.3 days and the enzymatic stability half-life in the hairless guinea pig plasma was around 6 minutes, indicating that any intact codrug that reached systemic circulation would regenerate the parent drugs as soon as it enters the body.

In both stability studies, regeneration of the parent compounds was observed with the degradation of the codrug. Compound 2A bioconverted completely in the skin to form only the parent compounds in the receiver and plasma in the in vitro diffusion and in vivo studies, respectively. Compound 2A made a very good proof-of-concept drug to test in vitro and in vivo in order to see if sufficient diclofenac could be deposited into the skin for therapeutic micropore closure delay, and also to see if it cleaved in the skin to the parent compounds. Compound 2B was synthesized next, as the ester linkage to NTXOL at the 6-O position has been found to be more chemically stable than linkage at the 3-O position of the phenolic ring. This is another reason to use NTXOL, because the 6-O position in NTX is a ketone and not a hydroxyl that can be easily made into a prodrug. However, other structures have been proposed to help improve the chemical stability of the 3-O phenolic hydroxyl prodrug linkage, e.g. Compound 2C with the addition of carbons in between to help slow the hydrolysis, and Compound 2G and Compound 2J with carbamate and carbonate linkages.

Experimental Design The detailed synthetic are set forth hereinbelow. All the reactions utilize established reagents and protecting chemistries. Hydrogen bonding capacity will be especially important in the design of the codrugs to be used with the aqueous pores formed by the microneedles. Molecular size can be somewhat increased in the case of the microneedle enhancement, as compounds as large as insulin have been delivered through micropores (McAllister et al., 2003). However, the present inventors have learned that an increase in viscosity, roughly correlated with the molecular weight of a compound, can decrease the diffusion rate through the microneedle pores (Milewski et al., 2010a; Milewski and Stinchcomb, 2010; Milewski and Stinchcomb, 2011; Milewski et al., 2010b), therefore polyethylene glycol (PEG, 11, 12) units will not be increased to over six. Codrug design can be limited to smaller molecular weights, if the solubility increase does not overshadow the molecular weight dependency with microneedle delivery.

The addition of the synthesis of the di-conjugated codrugs and their comparison with the successful mono-conjugated codrug moieties is novel. Ester, carbamate, and carbonate ester linked prodrugs are successful prodrugs, so these linkages have been maintained. All of the codrug structures will be optimized to solubilize and permeate through the aqueous channels created by microneedle delivery. These microneedle-assisted codrugs will therefore be very hydrophilic, but it is certain that a relatively fast bioconversion rate will still be an important property of these codrugs so that the diclofenac can be deposited into the skin. A more hydrophilic NTX codrug should more readily enter the microneedle-created pore, and then diffuse to the capillaries for systemic circulation uptake. More hydrophilic compounds should be taken up by the circulation more readily than lipophilic compounds, as can be seen in the sustained-release injectables body of literature, where changes in absorption rate correlate with lipophilicity and bioconversion. For example, furanose sugar (17), L-malic acid (18, 20), and phosphate acetic acid ester (15, 16, 19) promoieties will be studied to determine the flux enhancement with microneedles.

If the phosphate acetic acid ester is too chemically unstable, a regular phosphate ester group can be substituted, and sodium salts of these could also be made. Salts of all of the compounds are contemplated, as the present inventors have found that this is the best form to afford an increase in polarity and aqueous solubility (Banks et al., 2008). The preferred initial salt form is hydrochloride (Scheme 1), but lactate and glycolate salts would also be good candidates, for example. Lactate and glyco late salts are common in topical preparations at high concentrations. Acetate salts would not be practical because of potential odor. The acetate, lactate, and glyco late salts have higher solubilities in the pH range of interest for topical application, pH 4-6. Higher flux has been seen from NTX glycolate than NTX HCl through microneedle-treated skin in vitro, because one can achieve a higher solubility with glyco late. There is a maximum effect of solubility on flux when the viscosity outweighs the solubility effect (Milewski and Stinchcomb, 2011).

The goal is to categorize how the physicochemical properties of these codrug moieties when conjugated at the C-3 phenolic hydroxyl group or at the C-6 (naltrexol) influence stability and flux measurements, and then to evaluate any trends that may become evident from physicochemical properties and flux enhancement. Otherwise, physicochemical properties are altered only by the codrug link in between the two drugs via pegylation (11, 12), or by changing the chemical and enzymatic stability with ester, carbonate, carbamate (1-10), and anhydride (13, 14) groups. The addition of one to four carbon atoms (3-10, 13,14) in between the ester, carbonate, carbamate, and anhydride linkages is proposed to help improve chemical stability if necessary. Other design permutations, besides the 20+ proposed basic structures, are possible once data is gathered and optimization of flux and stability begins.

Figure 4:
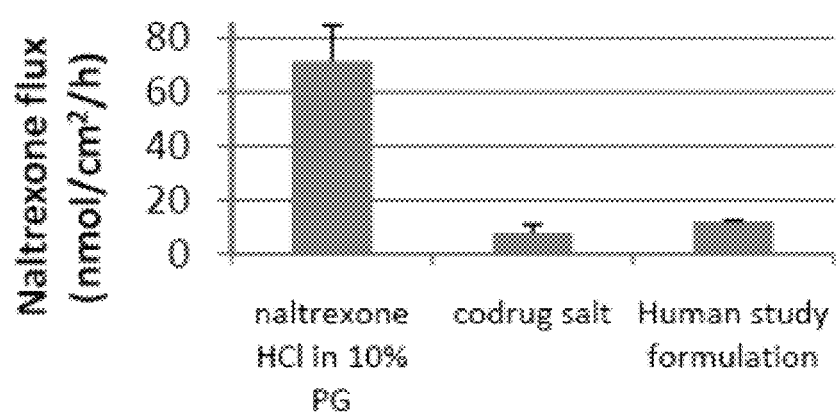
FIG. 4 is a graph showing NTX flux comparison from a human study with MN and NTX patches (Wermeling et al., 2008), the compound of FIG. 2A (codrug) salt, and an optimized NTX HCl formulation with 10% propylene glycol (PG). The human study used 60% PG, which causes a decrease in flux due to the viscosity increase (Milewski and Stinchcomb, 2011). The optimized NTX HCl flux is a target for embodiments of the compound.

A goal is to optimize solubility characteristics, chemical stability, and bioconversion rates, the most critical prodrug parameters identified. With these physicochemical attributes maximized, a therapeutic transdermal drug delivery rate may be achieved (FIG. 4). The maximum metabolic transformation rate may be limited at a Michaelis-Menten maximum rate, or Vmax, providing the enzymatically labile codrug is chemically stable enough to cross the micropores intact. Altering the linkages in the codrugs for polarity and bioconversion should significantly enhance the transdermal drug delivery rate. The general codrug design and synthesis methodology will allow for this flexibility. Many codrugs are proposed, but data collection will drive the decisions for which groups of compounds that will/will not be synthesized and tested, similar to what we have done with the currently funded proposal. In four years a maximum of 100 compounds could be synthesized. This number of compounds is well within the capabilities of our synthetic chemistry expertise, as we have already demonstrated in our currently funded studies.

Calculated codrug physicochemical parameters will include: molecular weight and volume (Bondi), octanol/water partition coefficients (Daylight® 4.51 Software), hydrogen-bonding potentials, relative thermodynamic activity and solubility parameters (Stinchcomb et al., 1995). A wide range of partition coefficients will provide a sufficient group of data for QSPR analysis. With every carbon addition to the alkyl chain, the clogP value usually increases by about 0.5. Generally, the greater a drug's innate tendencies to dissolve, the more likely it is that the drug can be delivered at an adequate rate across any membrane, including the skin. Therefore, experimentally determined prodrug physicochemical parameters will include: octanol/water partition coefficients, melting points and heats of fusion (important physicochemical determinants of solubility), and solubilities in select solvents at 32° C. (buffer and other vehicles used in the permeation experiments). Skin surface temperature is approximately 32° C. Difficulties sometimes arise in determining the octanol/water partition coefficients of readily hydrolyzed esters or extremely hydrophobic drugs. Experimentally determined octanol/water partition coefficients for some of the codrugs may not be practical, therefore relative HPLC retention times could substitute for partitioning estimation.

Solubility studies are carried out by equilibrating large excesses of each drug with the solvent studied. The experiments will be done at skin surface temperature (32° C.). To hasten the attainment of equilibrium, each slurry will be continuously shaken or stirred. Samples will be taken, filtered with an appropriate filter for the solvent, measured with respect to volume, and either assayed directly by HPLC or evaporated to dryness and reconstituted for assay. Binding of the compounds to the filter will be checked to eliminate the possibility of drug adsorption on the filter and/or filter casing. All toxic solvents and other chemicals will be handled with caution, and fume hoods will be used when appropriate.

The chemical stability of the prodrugs to hydrolysis and solvolysis at the appropriate temperatures will be determined by measuring concentrations over time in the buffers and solvents used in the solubility and diffusion studies. Chemical degradation rate constants will be important in distinguishing enzymatic degradation from non-enzymatic degradation. Codrug enzymatic metabolism rate constants can also be determined in skin homogenates, to ascertain if the values are useful in the QSPR multiple regression analysis. The kinetics of codrug enzymatic degradation in skin homogenates will be done using abdominal plastic surgery samples. Enzymatic reaction rates will be determined at several different codrug concentrations. The skin is homogenized (Polytron tissue homogenizer and ground glass homogenizer fitted with a glass pestle) in HEPES-buffered Hanks' balanced salt solution and the supernatant is obtained. The enzymatic hydrolysis rates are determined in the homogenate at 37° C. The codrug and its metabolites will be obtained by solid-phase extraction, or another appropriate extraction method. Naltrexone and any other metabolite formed will be assayed by HPLC and expressed as moles of metabolite per minute per milligram of protein. Protein concentrations in the supernatant will be measured by the Bradford method. Controls containing only codrug and HEPES-buffered Hanks' balanced salt solution at 37° C. will also be monitored to determine non-enzymatic hydrolysis.

The kinetics of codrug enzymatic degradation in skin homogenates will also be carried out using freshly dermatomed guinea pig skin samples. Immediately after the animals are euthanized, at the completion of their pharmacokinetic studies, untreated dorsal skin will be harvested for homogenate metabolism and in vitro diffusion studies. These metabolism studies will help to quantify any significant differences in the codrug enzymatic reaction rates between the guinea pig skin and human skin. Additionally, codrugs may metabolize to other compounds, besides just the parent drugs. The same procedure can also be done for pig skin.

Cox inhibitors other than diclofenac are contemplated. In some cases, a COX1-specific inhibitor may be better, in which case SC560, valeryl salicylate, mofezolac, FR122047 or another COX1-specific inhibitor can be used. In some cases, a COX2-specific inhibitor may be better, in which case, celecoxib, for example, can be used. In some cases, a less potent nonspecific COX inhibitor could be used, in which case ibuprofen, ketoprofen, or others are available. Such COX inhibitors have carboxylic acid moieties, and chemistry for synthesis does not change substantially. Celecoxib is an exception with an amine functional group, so different chemistry would be needed (Schemes), as would be recognized by one of ordinary skill in the art.

Drug penetration, concurrent bioconversion, and COX inhibitor deposition in skin in vitro with microneedle use.

Figure 6:
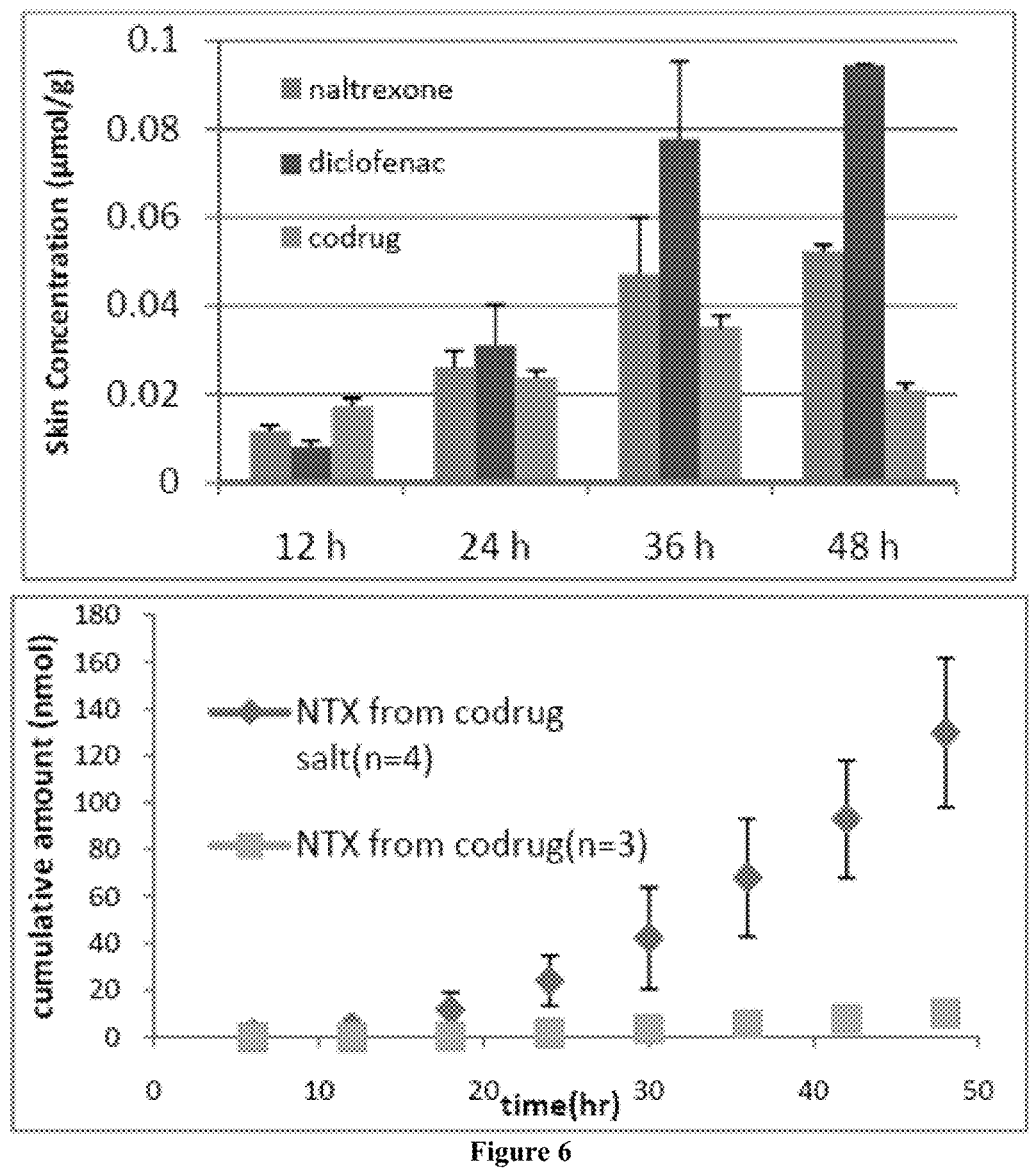
FIG. 6 includes graphs showing skin concentrations in Yucatan miniature pig skin in vitro after MN treatment and application of the compound of FIG. 2A (codrug). Experiments were terminated and skin disposition measured at 12, 24, 36, and 48 h. Flux values correlated with the skin disposition data, as the flux of NTX from the codrug was twice as high as the diclofenac flux, further proving the higher retention of diclofenac in the skin. The flux of NTX was also measured over 48 h from the compound of FIG. 2A and its HCl salt.

Compound 2A was tested in the in vitro diffusion study using Yucatan miniature pig skin with microneedle treatment. A study was conducted with Compound 2A, and a study was conducted with its HCl salt. FIG. 6 shows the skin concentrations obtained at different time points. NTX and diclofenac build to steady-state concentrations as the codrug hydrolyzes. More diclofenac is retained in the skin because it is more hydrophobic than NTX, and therefore diclofenac skin levels are higher than NTX as NTX diffuses into the receiver compartment.

Figure 5:
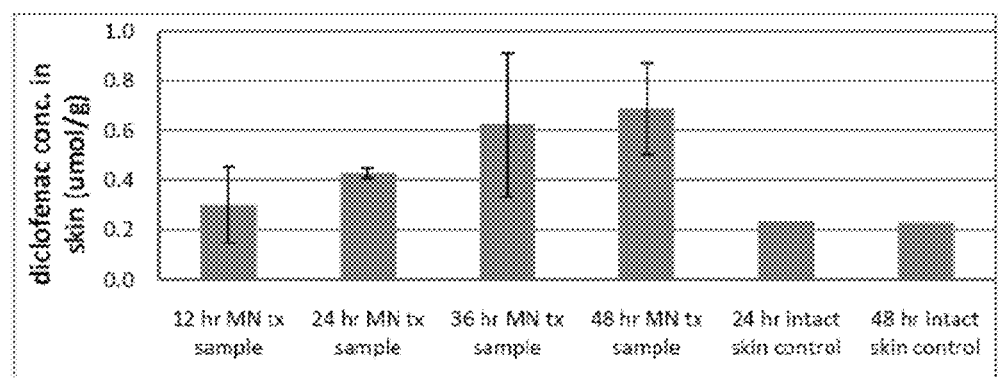
FIG. 5 is a graph showing skin concentrations of diclofenac after treatment with Solaraze gel in Yucatan miniature pig skin in vitro with MN treatment and non-MN treated controls. Daily application of Solaraze was applied to the skin to mimic the in vivo hairless guinea pig study where microneedle treated pores stayed open for 7 days (FIG. 7).
Figure 7:
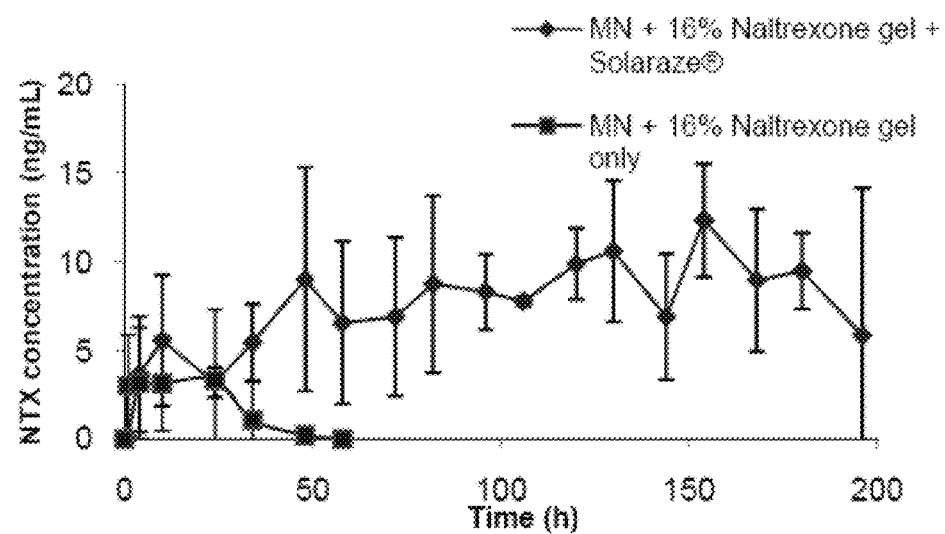
FIG. 7 is a graph showing NTX plasma levels in hairless guinea pigs after application of NTX gel alone or NTX gel and Solaraze (diclofenac gel). A control containing the hyaluronic acid in Solaraze was also tested, and an extension in micropore lifetime was not observed. No significant depletion from the NTX control gel was identified, as only a few percent of the total drug was delivered (Banks et al., 2011).
Figure 8:
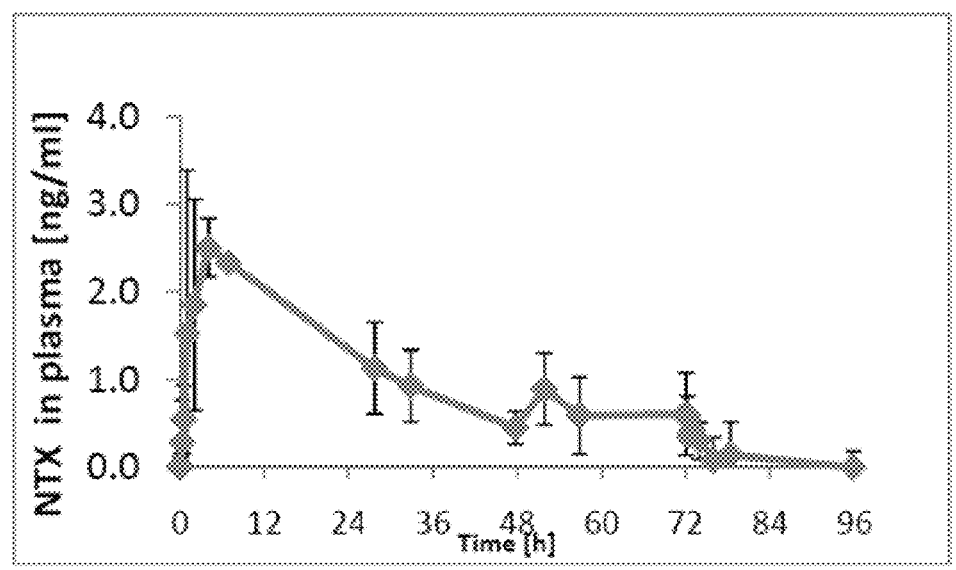
FIG. 8 is a graph showing NTX plasma concentrations in Yucatan miniature pig (n=3 trials) after topical dosing for 72 h with an NTX hydrogel and a single MN application. Time points from 72 to 96 hours are after patch removal. No NTX was detected when the same formulation (& patch area) applied to the pig without MN treatment. Similar to human results, showing the need for micropore closure inhibition. Intravenous NTX was evaluated in the pigs in order to determine the clearance of NTX and NTXOL.

FIG. 5 shows a diclofenac effective skin concentration goal, and Compound 2A did not provide that level, however, the codrug was successful in the hairless guinea pig pharmacokinetic study at keeping open the pores for 7 days, so it was most likely that more Solaraze (diclofenac) was being applied than necessary in the initial guinea pig study (FIG. 7). Therefore, a diclofenac skin concentration goal of 0.1 µmol/g of tissue may be all that is needed for effect. At any rate, the codrug is working as designed, to allow flux of NTX and retain diclofenac to have an effect on the micropore closure rate. The present inventors are testing the effect of Solaraze (diclofenac) on the micropore closure rate in human volunteers, and have seen similar results.

FIG. 6 also shows the substantial NTX flux improvement obtained from the compound salt as compared to the compound free base, consistent with previous data (Banks et al., 2008). Therefore, the focus will be on codrug salt forms, but non-salt forms are contemplated as well. This codrug completely hydrolyzed in the skin and only NTX and diclofenac were detected in the receiver compartment of the in vitro diffusion study.

Full thickness Yucatan miniature pig skin in vitro studies to measure diffusion and bioconversion will provide the most accurate absorption data with microneedle (MN) treatment. It is not necessary to use human skin when using microneedles, since the pig skin is the same thickness and the primary route of diffusion is through the MN pores and not the stratum corneum lipid bilayers. Human skin can be used in final experiments in order to make sure bioconversion is similar, however, the present inventors are primarily taking advantage of esterase activity and have not seen a difference in skin metabolism for this enzyme system in humans vs. pigs. Pig skin is purchased from Sinclair, or dermatome from sacrificed pigs used in the pharmacokinetic studies once the skin has returned to normal. The human skin in these experiments will be healthy full-thickness (subcutaneous fat removed) abdominal plastic surgery samples obtained from the Cooperative Human Tissue Network (CHTN). Universal Precautions (OSHA standards) will be used when handling the human skin samples, in order to protect the researcher from any potential harm. IRB approval is not required by NIH to use non-identified surgical waste tissue. Microneedle arrays purchased from 10× Technology or another manufacturer will be used for all studies, see letter of support attached.

Guinea pig skin samples will also be used in some in vitro diffusion and metabolism studies. We want to compare the transdermal flux rates seen in the animal in vivo data with animal in vitro data. It will also be important to see the differences between in vitro guinea pig skin and in vitro human/pig skin diffusion data. Since we are attempting to validate our in vitro human skin diffusion data with an in vivo animal model, we need to know the basic magnitude of difference in the skin permeabilities among the 3 species, if any. Micropore closing will not take place in vitro, so these experiments are used for flux optimization only. Detailed procedures for diffusion studies are in the publications in the Appendix and in our other publications. Simple analysis of variance (ANOVA) will determine significant differences among the codrugs' flux values.

In some studies it is contemplated to increase the microneedle array area (and needle number), which can increase flux, as there is a direct increase in flux with number of micropores. In some cases a 1 cm$^2$ (50 needles) array is used, but in other cases a 10 cm$^2$ array, and potentially an even larger array could be designed. Since the therapeutic delivery rate in humans with NTX HCl and 400 micropores has been achieved, it is believed that achievement of a 7-day codrug therapeutic flux is highly likely as long as a solubility similar to NTX HCl is achieved (FIG. 4). Some chemical stability issues can be resolved by limiting the water in the final patch formulation that would be used in a microneedle product.

Characterization of the Pharmacokinetics of the Drugs in Guinea Pigs and Yucatan Miniature Pigs In Vivo with Microneedle Use.

A study was done in hairless guinea pigs using diclofenac (Solaraze) gel applied daily to the micropores with a reservoir of NTX gel on top. NTX plasma profiles after one-time application of MN's in hairless guinea pigs with one-time application of 0.5 g of 16% NTX.HCl (control) compared to daily application of 0.5 g of 16% NTX.HCl and approximately 100 µl of Solaraze® topical gel (3% Diclofenac sodium), 6.7 cm$^2$ area (n=4) are shown in FIG. 7. Micropore lifetime was extended up to 7 days in the presence of diclofenac, but NTX without diclofenac had complete micropore closure in a similar timeframe to the human study, 2-3 days ((Banks et al., 2011) Appendix).

Figure 9:
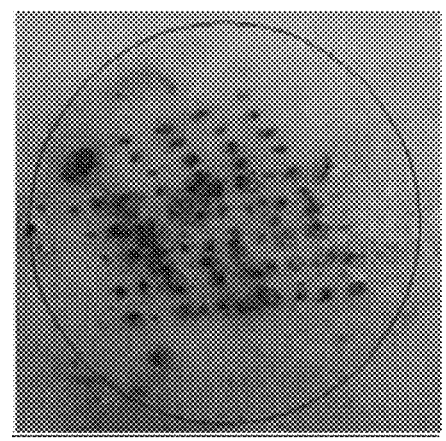
FIG. 9 is a picture of hairless guinea pig micropores visualized with India ink at the end of the 7 day experiment with the compound of FIG. 2A (codrug). Skin treated with microneedles that had pores that closed up did not show this type of staining, so the effect means the pores are viable. This technique has been used by others to visualize micropores in other studies. Pores heal quickly after the patches are removed (Banks et al., 2010).

Compound 2A in its HCl salt form was used to treat 4 hairless guinea pigs. Since flux from this codrug was low, four patches were placed on the guinea pigs with 7% saturated codrug gel after a single pretreatment with microneedles on Day 1. Microneedle treatment at each patch site contained 100 micropores created by a 1 cm$^2$ 50 needle stainless steel array rotated 90° and inserted twice. A new gel patch was applied at 3.5 days, as the chemical stability of Compound 2A is not ideal. Plasma samples were obtained from a jugular catheter over seven days and analyzed for drug concentration by LC/MS (Methods). In three out of the four guinea pigs significant NTX plasma levels were seen for 7 days, and the pores in one guinea pig closed at 6 days. Micropores were visualized on the skin of the animals at 7 days by staining the skin with India ink, and the 100 pores can be seen clearly, including the pattern from the 90° rotation and re-insertion FIG. 9. Intact codrug was not detected in the plasma samples. Significant micropore staining was also seen at days 1, 4, 5, 6, and 7.

A goal is to quantitatively characterize the transdermal delivery of selected naltrexone codrugs in vivo using pharmacokinetic determinants. This will be accomplished by comparing the kinetic profiles and parameters of intravenous bolus and topical applications of codrugs using the chronically annulated hairless guinea pig model. Hairless guinea pigs are a typical animal model used for transdermal delivery experiments. More importantly, guinea pigs have been shown to have a metabolic profile more similar to humans than rats or rabbits. Fifteen of the most promising codrug candidates screened in the in vitro experiments will be fully characterized in the guinea pig model. Plasma samples will be analyzed by LC/MS. Detailed procedures for hairless guinea pig pharmacokinetic studies and data analysis are in the Appendix publications and many previous publications from our group (Valiveti et al., 2005a; Valiveti et al., 2005b). Five to six animals (guinea pigs and pigs) per treatment group will be used, and dosing can be done in a crossover fashion, 2 routes of administration, intravenous vs. percutaneous. A codrug will be considered successful if it can deliver a similar or greater flux than that achieved in the human study with NTX HCl (Wermeling et al., 2008). Four of the most promising codrug candidates screened in the hairless guinea pigs will be examined in the Yucatan miniature pig, as the thickness of the skin is more similar to humans, important for microneedle application. This dose-finding proof-of-concept study in the pigs will provide data that can be included in an IND (Investigational New Drug) application, and optimizing the dosing of the best codrugs will help to prepare for pig toxicology studies required for the IND. ANOVA statistical analysis will be used in order to determine statistical significance among treatment groups.

Skin infection is not a concern with microneedle treatment and has not been a problem in the animal or human studies. Skin is swabbed with alcohol prior to microneedle treatment and formulations can contain microbicidal additives, like benzyl alcohol used in our human study (Wermeling et al., 2008). Microneedles are also very sturdy and do not break in the skin.

LC-MS/NIS conditions: Chromatography column used was Waters Atlantis Hilic Silica 5 μm, 2.1×150 with a mobile phase consisting of acetonitrile:buffer 80:20 (v/v). The aqueous buffer consisted of 1 mM ammonium acetate with 0.1% acetic acid and 5% MeOH. The injection volume was 20 μl. Liquid chromatography was carried out in the isocratic mode at flow rate 0.3 ml/min with a total run time of 14 min. The retention times for NDC, NTX, NTXol, DIC and NAL were as follows: 6.7 min, 9.6 min, 11.4 min, 7.4 min, and 1.6 min, respectively.

The LC-MS-MS system consisted of a HPLC Waters Alliance 2695 Separations Module, Waters Micromass® Quattro Micro™ API Tandem Mass Spectrometer. Positive electrospray ionization was used for detection of all compounds (ESI+), except DIC was analyzed through negative ionization (ESI−). Multiple reaction monitoring (MRM) was carried out with the following parent to daughter ion transitions for Compound 2A (NDC), NTX, NTXOL, diclofenac (DIC) and naloxone internal standard (NAL): m/z 619→342, m/z 342-324, m/z 344→626, m/z 293→250, m/z 328→310, respectively. Capillary voltage was 3.5 kV, RF lens 0.3 V, source temp 130° C., desolvation temperature 270° C. and cone voltage 29 V for NTX, NTXOL and NAL, 18 V for DIC and 38 V for NDC. The collision gas was 19 eV for NTX, 10 eV for DIC and 20 eV for NDC, NTXOL and NAL. Nitrogen gas was used as a nebulization and drying gas at flow rates of 50 and 450 L/h, respectively. Calibration plots were prepared by a linear regression analysis of the ratio of the drug-to-internal standard areas versus nominal drug concentration. Quadrupoles were set on unit mass resolution. Based on the peak-to-noise ratios of 3:1 for LOD the following limits of detection were estimated: NDC<1 ng/ml, NTX 3 ng/ml, NTXOL 1 ng/ml and DIC 1 ng/ml. Based on the peak-to-noise ratios of 10:1 for LOQ the following limits of quantification were estimated: NDC 3 ng/ml, NTX 10 ng/ml, NTXOL 3 ng/ml and DIC 3 ng/ml.

Vertebrate Animals

The hairless guinea pig pharmacokinetic/irritation and pig pharmacokinetic experiments will make use of 92 guinea pigs (male and female IAF hairless; from Charles River Laboratories); 400-450 g, 6-8 weeks old 12 Yucatan miniature pigs (male and female; from Sinclair BioResources); ~15 kg, 3 months old The proposed experiments will be conducted as described:

Male and female IAF hairless guinea pigs (400-450 g) will have surgical implantations of jugular catheters (pharmacokinetic studies). Hairless guinea pigs (n=5-6 per test compound) are used typically as a small animal model for topical/transdermal studies. After a 1-2 day recovery period, animals will be dosed with i.v. or topical drug doses and blood sampling will be done for up to 96 hours. Blood removal will not exceed 10% of the animal's total blood volume. Plasma samples are harvested and analyzed by LC/MS. Test compounds will be screened in the guinea pigs and the most successful candidates will be tested in the pig model. Animals are euthanized at the end of the experiments.

Male and female miniature pigs (~20 kg) will be purchased with two surgically implanted subcutaneous titanium ports (Access Technology) from Sinclair BioResources. Sinclair BioResources (USDA #: 43-R-0104 and assurance #: A4333-01) has staff veterinarians that perform the surgeries according to IACUC protocol (#10402). The surgically implanted pigs remain on-site for 10 days before shipping to the University of Kentucky. Pigs will be transported and acclimated for 7 days once at the university before initiation of any pharmacokinetic studies. Miniature pigs (n=5-6 per test compound) are used typically as a large animal model for topical/transdermal studies. This breed of pig is ideal for topical/transdermal studies due to minimal body hair compared to other breeds. The pig will be placed in a sling for dosing and sampling. Pigs will be dosed with topical drug doses after MN application and blood sampling (24 pre-determined time points) will be done for up to 168 hours. A jacket (Lomir Biomedical Inc) is placed on the pig to prevent the pig from removing the patches. Lidocaine (4%) cream is applied to the port area for 10 min prior to blood collection to minimize discomfort to the pig. Specialized Huber needles are used for flushing and sampling to maintain the integrity of the ports. Blood removal will not exceed 10% of the animal's total blood volume. Plasma samples are harvested and analyzed by LC/MS/MS. Weights are obtained prior to initiation of studies and monitored weekly. Animals are euthanized after completion of the experiments.

Skin irritation in hairless guinea pigs (n=5-6 per test compound): Erythema from topical drug treatments can be quantified with a Minolta ChromaMeter (Kobayashi, Hosaka et al. 1997; Sutinen 2000). A colorimetric measurement of the skin reflection is taken before and after the topical drug treatment, in order to assess skin irritation (Kobayashi, Hosaka et al. 1997). Trans-epidermal water loss (TEWL) measurements will also be taken before and after patch application, as a relative measure of skin damage. These two skin measurements are complimentary, and should provide a good prediction of potential treatment irritation (Kobayashi, Hosaka et al. 1997; Sutinen 2000). The irritation potential of the drugs will be evaluated by taking erythema and trans-epidermal water loss (TEWL) readings at the induction sites after patch removal. Erythema from topical drug treatments will be quantified with a Minolta Chromameter (Kobayashi, Hosaka et al. 1997). Both chromameter and TEWL reading will be taken before and after patch removal as a relative measure of redness and skin damage, respectively. Readings will be taken at 5 min and thereafter at 1, 2, 24 and 48 h, and daily throughout treatment. Reactions will be visually graded for erythema at 24 and 48 h after patch removal according to a 5-point grading scale (0, 0.5 (±), 1, 2, 3). The grades 1, 2 and 3 denote increasing severity of erythema with grades >1 considered positive. The "0.5 or (±)" grade will be used for equivocal reactions and will be considered negative. Responses will be evaluated by two indices, one for incidence and one for severity, for both test and control animals. The incidence index will be determined by the number of animals showing a response grade of 1 or greater at either 24 or 48 h out of the total animals in the group. The severity index will be determined for both 24 h and 48 h response readings by dividing the sum total of grades in a given group by the total number of animals exposed.

Pharmacokinetics—Pharmacokinetic parameters will be determined by fitting the plasma concentration vs. time data (AUC) during and after drug administration by nonlinear least squares regression analysis, using commercially available software (SCIENTIST, Micromath, Inc. or WINNONLIN) and a multi-exponential mathematical equation, as follows:

$$C = k_0 \sum_{l=i}^{n} C_l (e^{\lambda_l T} - 1) e^{-\lambda_l t} \qquad \text{Eq. 1}$$

where $k_0$ is the zero-order administration rate, T is the administration time and $C_1$'s and $\lambda_1$'s are fitted parameters describing the absorption, distribution and elimination rate constants. The multi-exponential model will be used to construct smooth curves through the data to compute AUC and AUMC to the last time point, and will take into consideration, when necessary, metabolite kinetics (Rowland and Tozer). If the multiexponential model does not provide an adequate fit for the data, more complex mathematical models will be considered. In some cases we expect that the codrugs will hydrolyze so rapidly to NTX that elimination of NTX will not be rate-limited by the bioconversion. The clearance of NTX should be much lower than the codrugs' clearance values.

The elimination rate constant (k) will be determined from the terminal log-linear portions of the curves. If the codrug and NTX exhibit similar terminal log-linear slopes after the i.v. dose of codrug, then the NTX elimination is rate-limited by its formation. The fraction (fNTX) of an i.v. dose of codrug converted to naltrexone will be calculated by:

$$f_{NTX} = \frac{AUC(NTX \to PROIV) \times CL_{NTX}}{AUC(PRO \to PROIV) \times CL_{PRO}}$$

AUC(NTX→PROIV) refers to the area under the curve of the naltrexone plasma profile following an i.v. bolus of codrug. AUC(PRO→PROIV) refers to the area under the curve of the codrug plasma profile following an i.v. bolus of codrug. The peak plasma concentrations (Cmax) after the i.v. bolus doses of the drug will be used to determine the initial volume of distribution by the following equation:

$$V = \frac{Dose}{C_{max}}$$

Noncompartmental pharmacokinetic determinants calculated will be total clearance (CL=[dose]/AUC), volume of distribution at steady-state (Vss=dose×[AUMC/AUC$^2$–T/(2×AUC)]), and MRT (MRT=AUMC$_{0-\infty}$/AUC$_{0-\infty}$–T/2). (AUC=Area under the concentration vs. time curve; AUMC=Area under the first-moment-time curve; MRT=Mean residence time)(Gibaldi and Perrier). The percutaneous absorption data from rapidly skin-converted codrugs should provide a plasma concentration time profile that exhibits zero-order delivery to an average steady-state level (Css) of parent drug.

The average transdermal codrug absorption rate R should also be equal to:

$$R = \frac{C_{ss}Vk}{f_{NTX}}$$

Where Css, V, and k are parent drug values. After removal of the topical codrug treatment, the elimination would be controlled by the compound with the longer elimination half-life, in some cases parent drug. Statistical analyses for group comparisons will be evaluated by ANOVA, followed by Tukey post-hoc testing for individual group differences. Differences will be considered significant when p<0.05.

Figure 10:
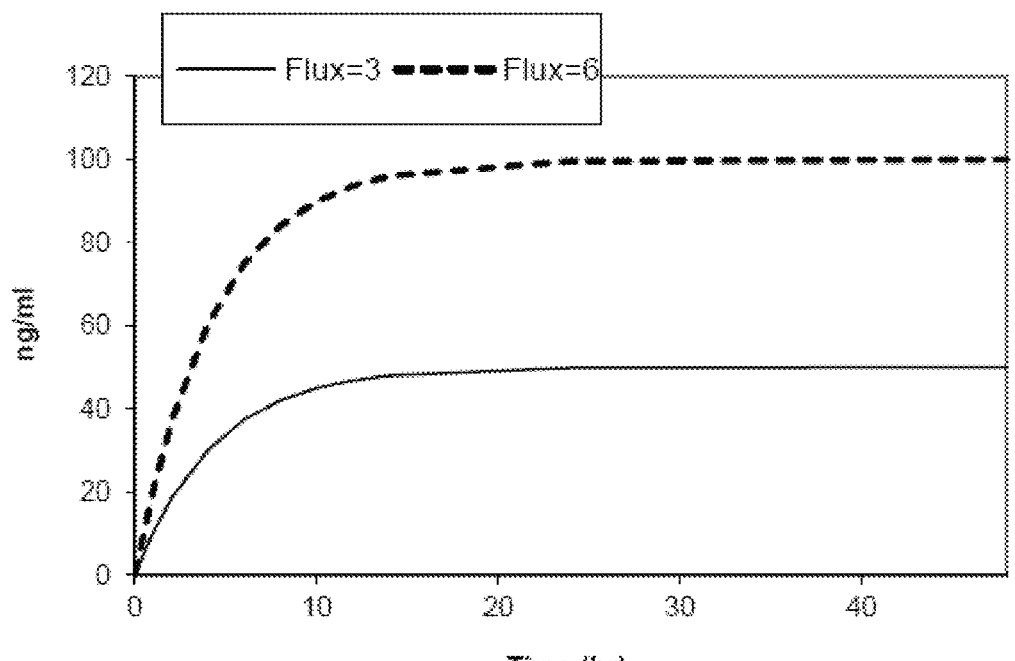
FIG. 10 is a graph showing how plasma concentration changes with a change in flux rate.

Changes in flux enhancement that we have seen in the in vitro studies should be mimicked in the in vivo studies. For example, if a codrug provides a two-fold increase in NTX flux in vitro, one would expect to see the steady-state plasma concentrations of NTX double (see FIG. 10).

Lag times will be calculated for each individual set of data. After the topical treatment is removed, the plasma levels will begin a first-order decline after the "drug reservoir" remaining in the skin is eliminated. The residual levels of drug left in the skin will be monitored, and an elimination rate constant will be calculated from the terminal log-linear portion of the profile. The peak plasma concentration (Cmax) and time to reach the Cmax (tmax) will be read directly from the plasma-concentration time profiles.

Preliminary in vitro miniature pig skin studies have been completed for this project. Animal experiments are also contemplated. A 1997 article describing a type of artificial skin was identified. These systems have the same type of disadvantages as any in vitro testing: the microcirculation and enzymatic activity of the in vivo skin model is not represented. It is not possible to study irritation and pharmacokinetics without an in vivo model. Guinea pigs have a history of use in topical irritation testing. Hairless guinea pigs are a typical small animal model used for transdermal experiments. More importantly, guinea pigs have been shown to have a metabolic profile more similar to humans than rats or rabbits. Miniature pigs are used typically as a large animal model for transdermal studies. From previous experience with animal studies, guinea pigs and pigs can be tested more than once following a washout period which helps to reduce the number of animals needed to complete the necessary studies. Animal studies are necessary to gather preliminary data in order to determine safety of the compounds and pharmacokinetics before clinical studies are conducted. Based on experience from previous research and other researchers, these protocols have been established for the number of animals required to provide sufficient statistical power to detect significant differences at p<0.05 using ANOVA and Tukey post-hoc comparisons. The number of animals used is in confoiinity with good pharmacological practices.

The University Department of Laboratory Animal Resources (DLAR) has several full-time veterinarians available that can evaluate the animals if any infection or adverse reaction occurs. The University operates to comply with the USDA Animal Welfare Act (Public Law 89-544) as amended by PL91-579 (1970) PL94-279 (1976) and 45CFR37618 (6-30-80); Health Research Extension Act of 1985 (Public Law 99-158); follows the Public health Service Policy on Humane Care and Use of Laboratory Animals (revised September 1986); and the Guide for the Care and Use of Laboratory Animals DHEW (NIH) 85-23 revised 1985. The facilities' staff involved with institutional animal care and use is adequately trained and competent and abides by all provisions set forth by the Animal Welfare Act as well as other federal, state, and local laws for Animal Welfare. If any animals have infections or injury, a facility veterinarian will be consulted and the appropriate treatment will be made or if necessary the animal will be euthanized. The facility's veterinarians will be consulted to determine if administering of analgesics are advised or terminating the study at that point. The studies are not considered a painful procedure unless the procedure causes more than slightly or momentary pain or distress in a human being to which the procedure was applied, this is pain in excess of that caused by injections or other minor procedures. If the test compounds used elicit a painful response or maximum scores, the animal will be humanely euthanized as per the University standard operating procedures or the animal will receive the appropriate sedatives, analgesics, or anesthetics as per the University standard operating procedures. All surgical and tissue collection procedures are conducted under general anesthesia.

All animals are acclimated 7 days prior to initiation of the studies. All animals are judged to be healthy prior to utilization in the study. Each guinea pig will be housed individually in a plastic cage with access to two water bottles and food. The animals will be fed a standard guinea pig diet daily ad libitum. Aseptic surgery will be performed on the guinea pigs. The animals will be fasted four hours prior to surgery. Guinea pigs will receive pre-operatively glycopyrolate (0.02 mg/kg, sc) and buprenorphine (0.05 mg/kg, sc). Guinea pigs will be anesthetized with ketamine (100 mg/kg, ip) and xylazine (8 mg/kg, im). Additional ketamine and xylazine is administered as needed. A sterile catheter will be inserted into the jugular vein. All catheters will be tunneled to the back, secured, and plugged. Intraoperative monitoring of the animal's condition will include respiration, heart rate, and response to stimulation. Post-op the guinea pigs will be given buprenorphine (0.4 mg/kg, sc) for analgesia and an antibiotic (fluoroquino lone; 5 mg/kg, sc) if infection occurs.

Each pig will have a ten square foot pen with free access to fresh water. The animals will be fed a standard pig diet twice daily. Pigs will be restrained in a sling during blood sample draws from the chronically implanted catheter. If the pigs are kept in the sling for several hours, they will have access to water. Pig acclimation to the sling for several hours at a time will be done during the first week after the animals' arrival. The pigs will be monitored for undue stress from the restraint. For the previously described procedures, Yucatan miniature pigs will be momentarily restrained for procedures and dosing and then will be returned to their respective cages for observations. Lidocaine (4%) cream is applied to the port area for 10 min prior to blood collection to minimize discomfort to the pig.

Irritation readings in hairless guinea pigs are monitored at 5 min and thereafter at 1, 2, 24 and 48 h after application. Reactions will be visually graded for erythema at 24 and 48 h after patch removal.

Observations are made at least once daily for the remainder of the studies. Hairless guinea pigs and miniature pigs are monitored at each time point blood samples are obtained for pharmacokinetic studies and at least once daily for the remainder of the studies. Daily weights and rectal temperatures are obtained from the guinea pigs. Biweekly weights and rectal temperatures are obtained from the miniature pigs. Guinea pigs and pigs will be housed individually. All animals will be fed a standard diet and offered ad libitum water.

For the previously described procedures, guinea pigs will be momentarily restrained for procedures and dosing and then will be returned to their respective cages for observations. If any animals have infections or injury, a facility veterinarian will be consulted and the appropriate treatment will be made or if necessary the animal will be euthanized. The facility's veterinarians will be consulted to determine if administering of analgesics are advised or terminating the study at that point. The studies are not considered a painful procedure unless the procedure causes more than slightly or momentary pain or distress in a human being to which the procedure was applied, this is pain in excess of that caused by injections or other minor procedures. If the test compounds used elicit a painful response or maximum scores, the animal will be humanely euthanized as per the University standard operating procedures or the animal will receive the appropriate sedatives, analgesics, or anesthetics as per the University standard operating procedures. All surgical and tissue collection procedures are conducted under general anesthesia. The facilities' staff involved with institutional animal care and use is adequately trained and competent and abides by all provisions set forth by the Animal Welfare Act as well as other federal, state, and local laws for Animal Welfare.

There will be no unnecessary duplication of studies and that all reasonable efforts will be made to minimize animal exposure to pain, stress, and discomfort whenever possible. All protocols are approved by the University Institutional Animal Care and Use committee. All personnel handling laboratory animals are required to successfully complete a basic training program (Education and Training in the Care and Use of Laboratory Animals: A Guide for Developing Institutional Programs, National Academy Press, 1991). Additional species and procedure specific training programs are provided through the DLAR training program and the AALAS Learning Library is available to all University personnel using vertebrate animals in research and teaching.

If the test compounds used elicit a painful response or if maximum scores, the animal will be humanely euthanized as per the University DLAR's standard operating procedures if the appropriate sedatives, analgesics, or anesthetics would not alleviate the pain or distress of the animal. If the animal has a weight loss of greater than 10%, the animal will be humanely euthanized. At the end of the experiments, guinea pigs (minimum dosage of 0.22 mL/kg of body weight) will receive Beuthanasia-D Special (pentobarbital sodium and phenytoin sodium) overdose. At the end of the experiments, pigs will be sedated with ketamine (20 mg/kg, im) and euthanized with an intravenous overdose of Beuthanasia-D Special as approved by the AVMA panel on Euthanasia. This type of euthanasia is simple and routinely used for guinea pigs and pigs at the animal research facilities.

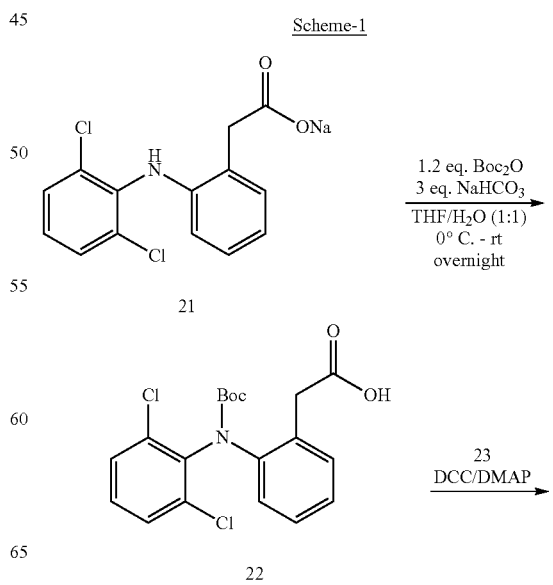

-continued

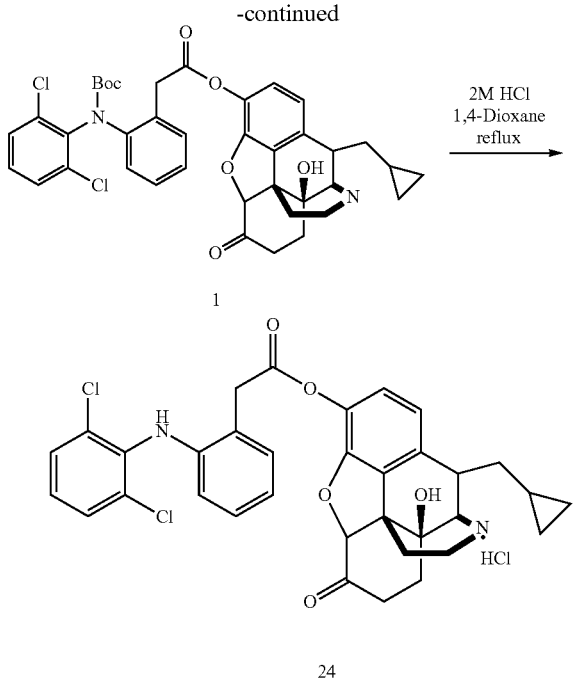

Commercially available sodium salt of diclofenac (21) will be protected with Boc group using Boc anhydride to prevent intramolecular cyclization reaction. After overnight reaction at room temperature, Boc-protected diclofenac (22) will be obtained by extraction using diethyl ether and cold 1N HCl. Compound 22 and naltrexone (23) will be coupled using conventional coupling approach to yield a Boc-protected codrug. Boc-protected diclofenac-naltrexone codrug (1) will be dissolved in 1, 4-dioxane and treated with equimolar 2M HCl in dioxane to give hydrochloride salt of diclofenac-naltrexone (24) after 1 h reflux. To determine whether acid groups can be readily attached to naltrexone or naltrexol, we performed a pilot experiment using Boc- or Fmoc-protected amino acids, successfully yielding amino acid-coupled naltrexone or naltrexol.

Codrug-1: Sodium salt of diclofenac was dissolved in 1:1 (Ethyl acetate:Water) mixture and acidified with concentrated hydrochloric acid. Organic layer was separated and aqueous layer treated with ethyl acetate two times. Combined organic layer was dried on anhydrous sodium sulfate and rotary evaporated to remove reaction solvents. Diclofenac free acid was activated with DCC (N, N'-Dicyclohexyl carbodiimide)) and DMAP (4-Dimethylaminopyridine) in dry tetrahydrofuran. After two hours, equivalent naltrexone was added in dry tetrahydrofuran. Combined reactants were allowed to stir over night under nitrogen atmosphere. After completion of the reaction, solvents were removed under reduced pressure and reaction crude mixture purified by flash silica gel column chromatography eluting with 80% ethyl acetate and 20% cyclohexane and codrug-1 was obtained in 56% (Scheme-1) yield. The codrug-1 was dissolved in 1, 4-dioxane and an equimolar amount of 2M hydrochloric acid in dioxane was added and refluxed for 1.5 hrs, and precipitated with hexanes to get hydrochloride salt codrug-24 (Scheme-1).

$^1$HNMR (CDCl$_3$, 300 MHz): δ 6.57 (d, 1H), 6.60 (d, 2H), 6.75 (d, 1H), 6.93 (m, 2H), 7.19 (t, 1H), 7.29 (m, 2H)

$^{13}$CNMR(CDCl$_3$, (300 MHz): δ 4.22, 4.41, 9.77, 23.31, 31.09, 31.59, 36.45, 38.50, 43.75, 51.01, 59.48, 62.15, 70.28, 90.93, 118.75, 119.52, 122.45, 123.05, 124.19, 124.31, 128.30, 128.97, 129.73, 130.38, 130.64, 131.31, 132.63, 138.09, 142.92, 147.77, 169.98, 207.67

HRMS: Calculated for C$_{34}$H$_{32}$O$_5$N$_2$Cl$_2$ 618.1688 and found 618.1697.

Scheme-2

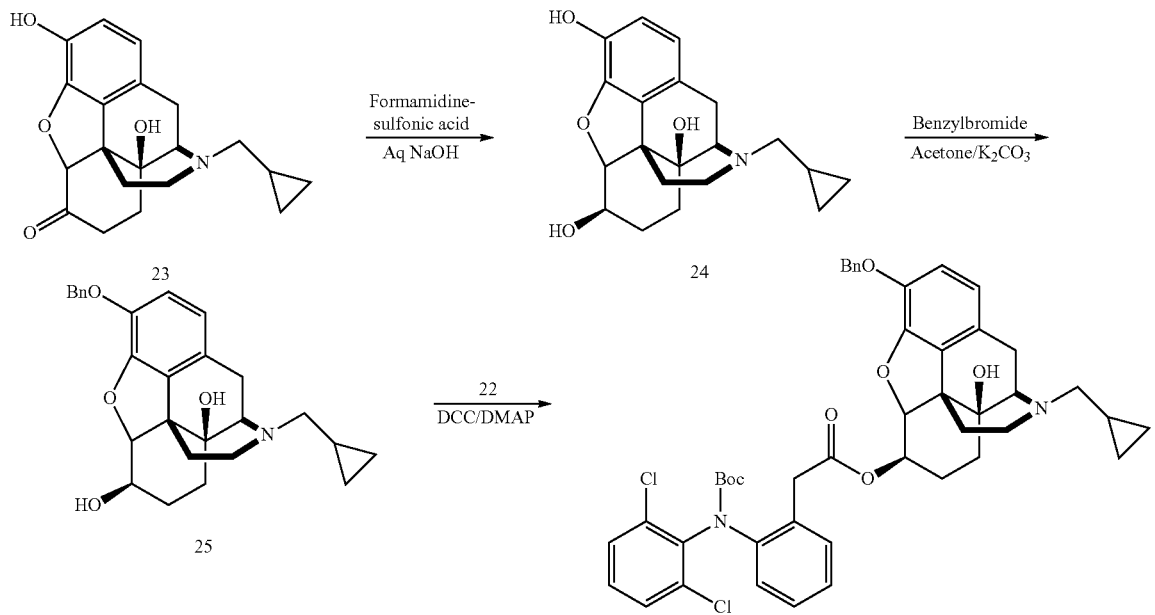

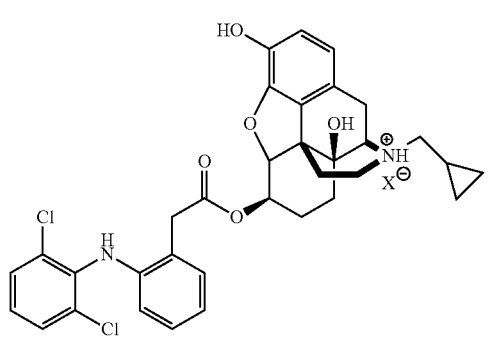

27

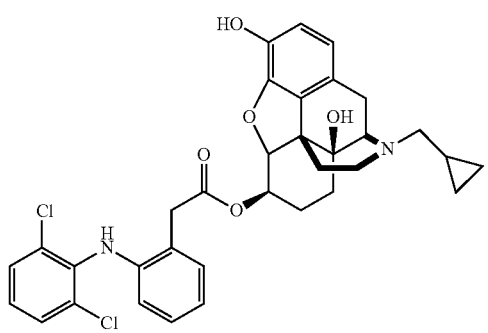

2

2 M HCl
1,4-Dioxane
Reflux

Naltrexol (24) was synthesized with a reported process (Decosta, Iadarola et al. 1992) and phenolic hydroxyl group was protected with benzyl bromide to get compound (25) (Pelotte, Smith et al. 2009). Benzyl protected naltrexol (25) will be coupled with Boc-protected diclofenac acid (22) to provide naltrexol-diclofenac codrug-(2). This codrug on treatment with hydrochloric acid produced the salt form of codrug-(27).

Codrug-2: Diclofenac acid was dissolved in dry THF and activated with DCC/DMAP for about two hours on an ice bath. Later on 3-OBn-6-β-naltrexol was added drop wise in dry THF, and reaction mixture allowed to stir over night under nitrogen atmosphere. Completion of the reaction was monitored with TLC and crude compound washed with ethyl acetate to get rid of dicyclohexy urea and purification on silica column gave titled compound-2 (Scheme-2) in 60% yield.

Chemical Formula: $C_{34}H_{34}Cl_2N_2O_5$, Exact Mass: 620.18, Molecular Weight: 621.55

$^1$H-NMR (CDCl$_3$, 500 MHz) δ 7.34-7.30 (m, 2H), 7.26-7.7.24 (m, 1H), 7.16-7.07 (m, 1H), 6.97 (s, 2H), 6.88-6.85 (m, 1H), 6.70-6.68 (m, 1H), 6.56 (m, 1H), 4.74-4.62 (m, 2H), 3.85 (s, 2H), 3.08 (s, 1H), 3.02-2.98 (m, 1H), 2.64-2.55 (m, 2H), 2.36-2.23 (m, 3H), 2.12-2.07 (m, 1H) 2.01-1.63 (m, 1H), 1.79-1.76 (m, 1H), 1.59-1.57 (m, 1H), 1.46-1.40 (m, 2H), 1.25 (m, 3H), 0.87-0.83 (m, 2H), 0.83-0.51 (m, 2H), 0.11 (s, 2H)

MS-spec: calcd. 621.2 (M+H)$^+$. found 621.2.

Scheme-3

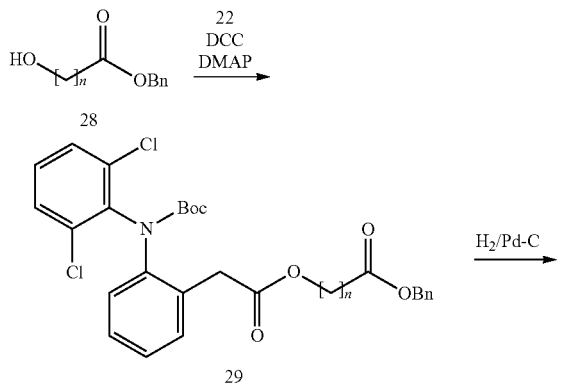

Commercially available benzyl protected hydroxy acids (28) will be used in this synthesis. If not required, starting material will be synthesized according to reported procedures (Sunazuka, Tsuzuki et al. 1992). Precursor (29) will be obtained on DCC coupling of benzyl protected hydroxy acid (28) and Boc-diclofenac acid (22). Hydrogenation of compound 29 followed by coupling with naltrexone (23) will give codrug-(3).

Scheme-4

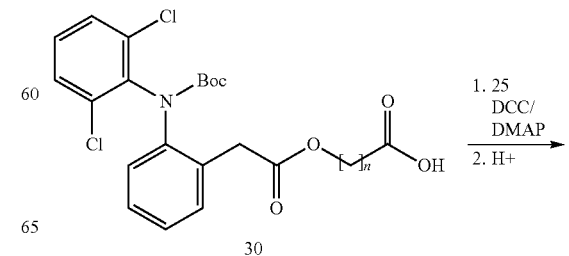

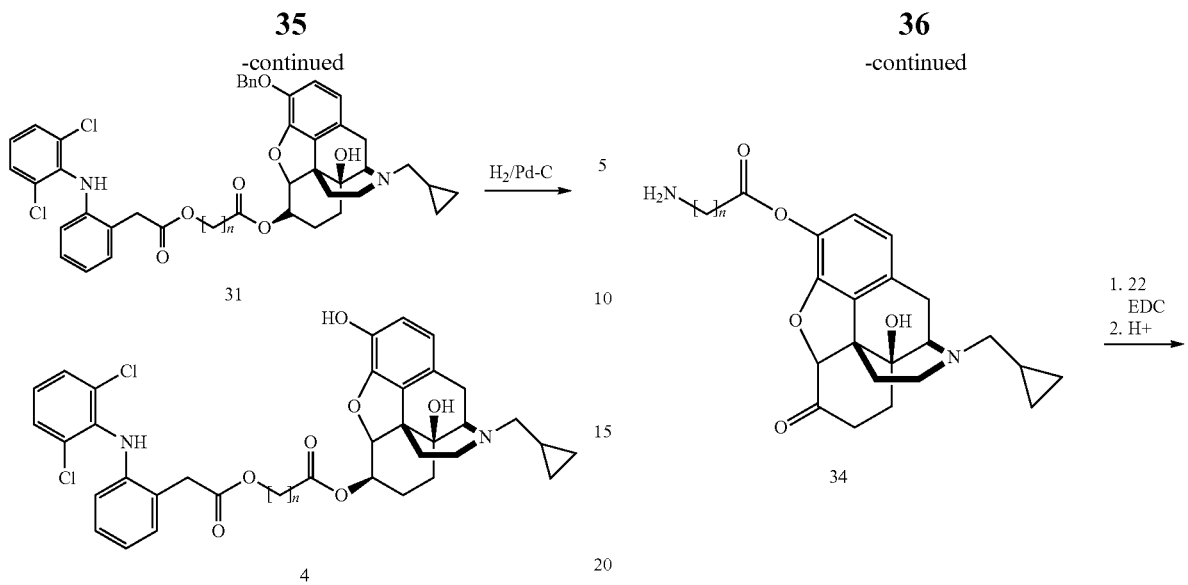

Parallel protocol will be used to make codrug-(4). Debenzylation via hydrogenolysis of intermediate (31) will give target codrug-(4).

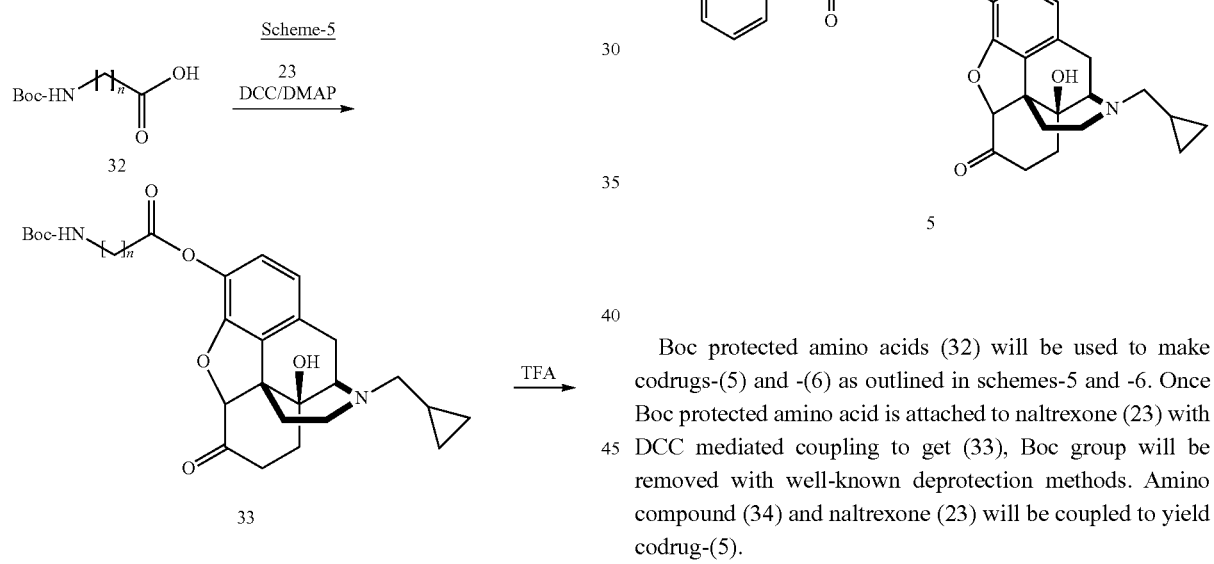

Boc protected amino acids (32) will be used to make codrugs-(5) and -(6) as outlined in schemes-5 and -6. Once Boc protected amino acid is attached to naltrexone (23) with DCC mediated coupling to get (33), Boc group will be removed with well-known deprotection methods. Amino compound (34) and naltrexone (23) will be coupled to yield codrug-(5).

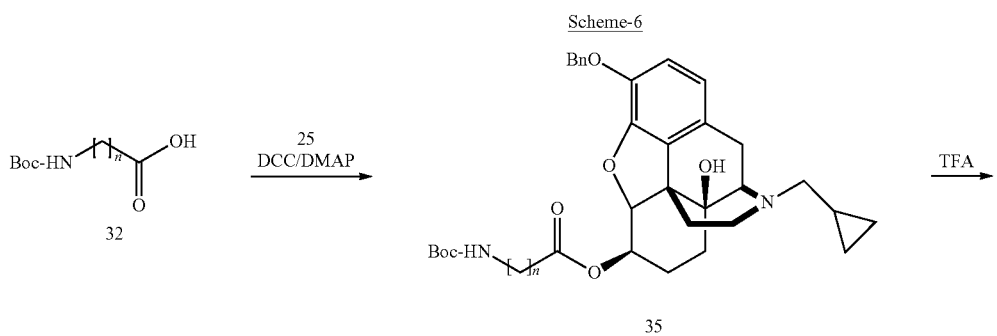

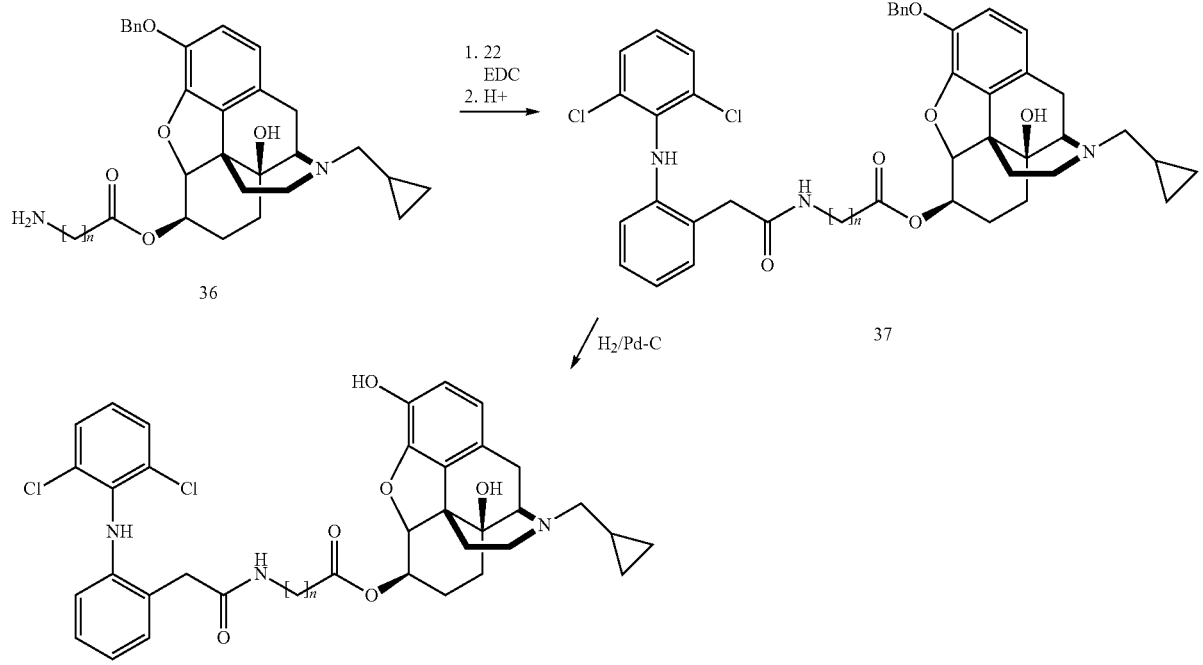
To make codrug-(6) with ester and amide link, benzyl protected naltrexol (25) will be used. Debenzylation of (37) will yield codrug-(6).
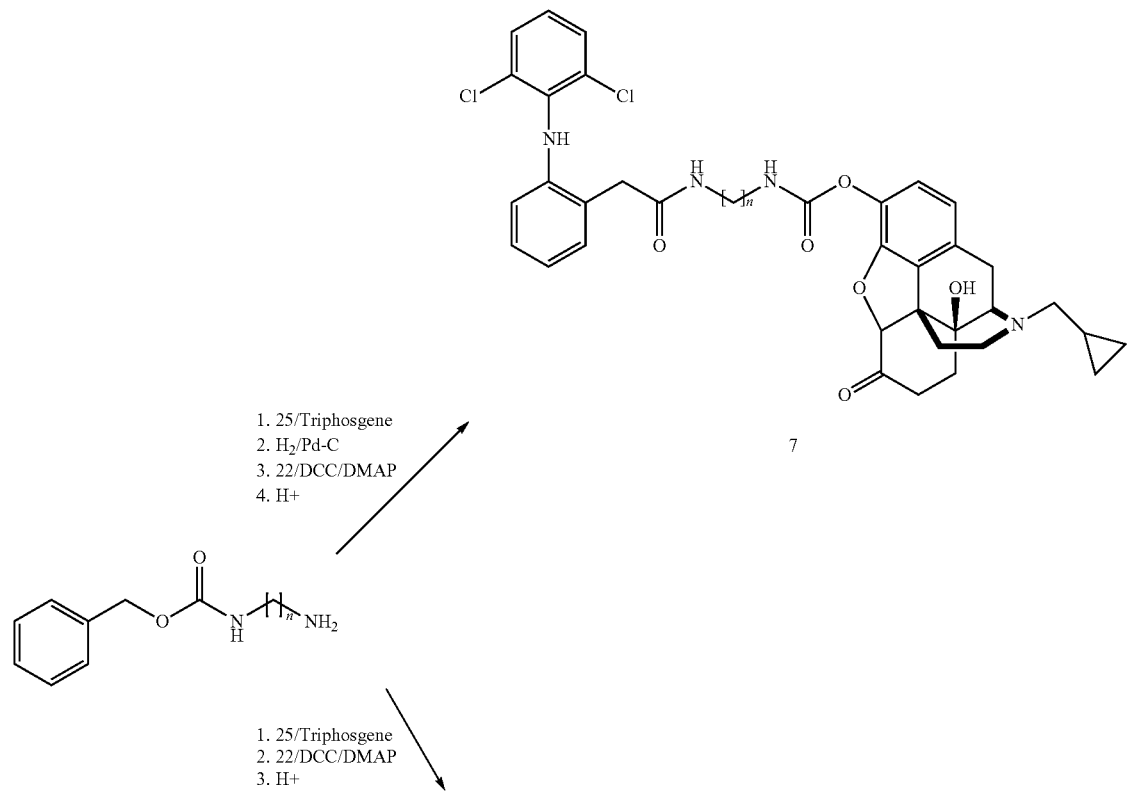

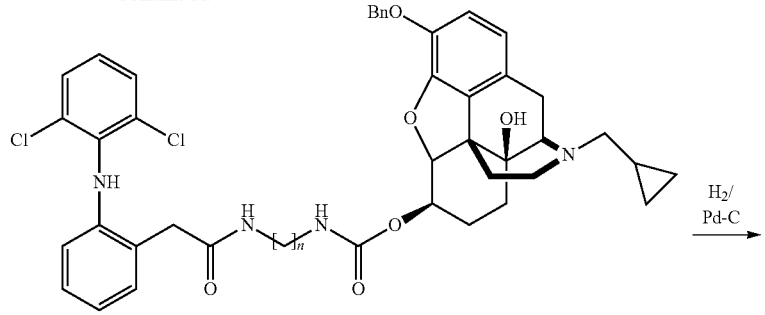

39

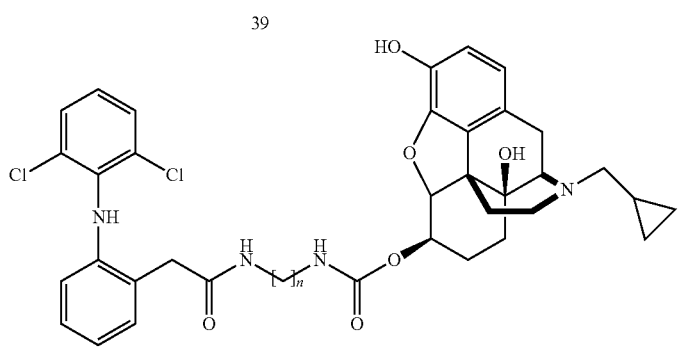

8

Mono benzyl amine protected starting materials will be used to produce amide-amide linked spacer codrug-(7). Unavailable starting amino compounds will be synthesized according to published methods (Krivickas, Tamanini et al. 2007). Triphosgene treated naltrexone (Hamad, Kiptoo et al. 2006) (23) on action with (38) will give compound 39 (Scheme 7). As outlined in scheme-7, codrug-(8) will be synthesized by hydrogenation of compound 39.

Scheme-8

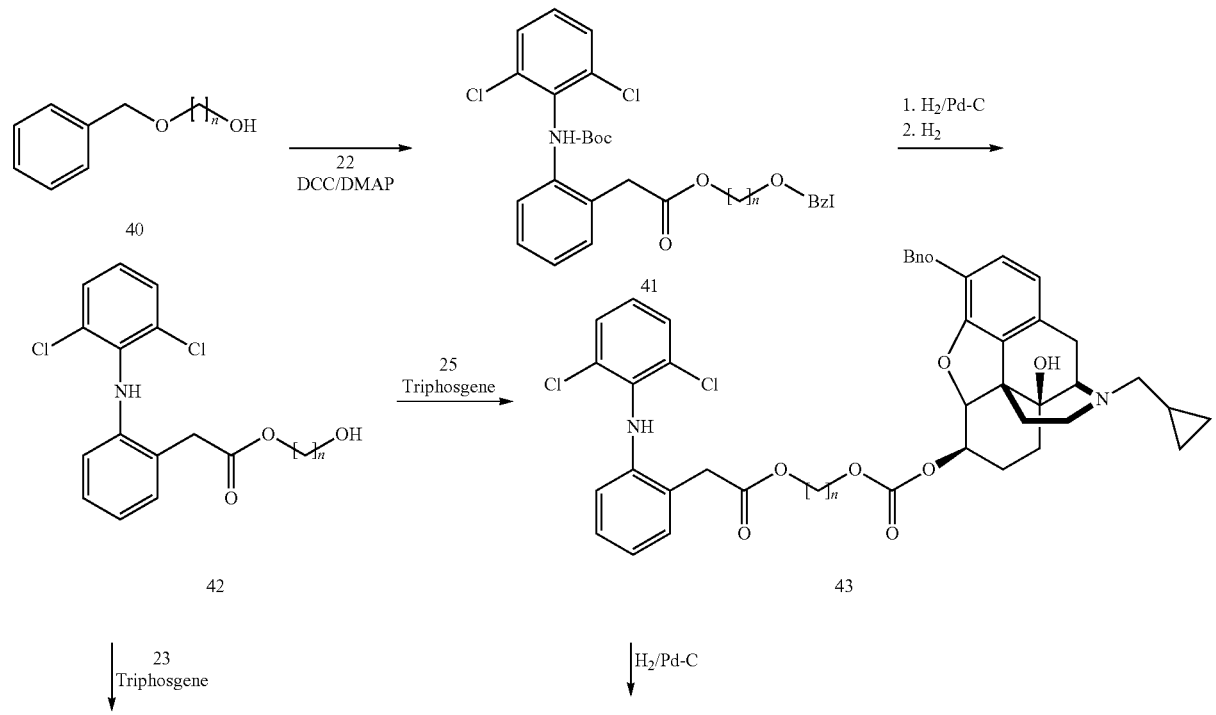

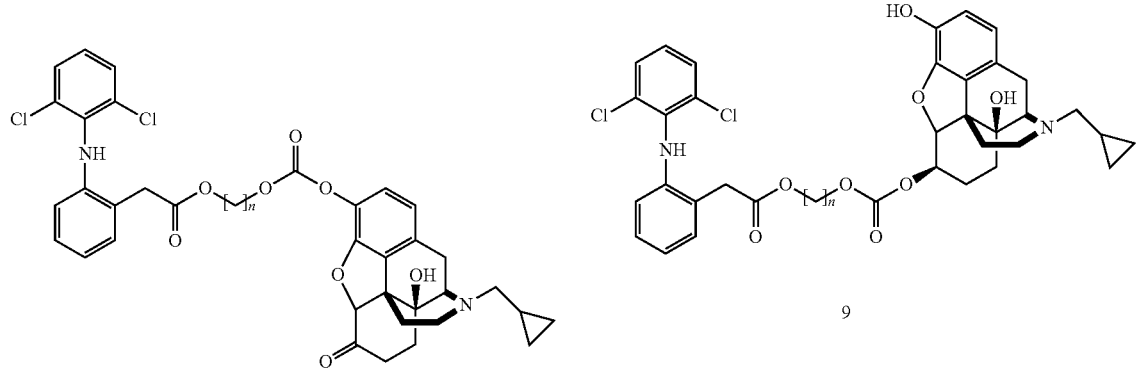

10

9

O-mono benzyl protected diols (40) will be used as starting materials for the projected synthesis or materials will be synthesized according to literature protocols (G. Venkateswar Reddy 2009), (Simas, Pais et al. 2003). DCC mediated union between diclofenac acid (22) and O-mono benzyl diol (40) will give derivative-(41). This derivative (41) on debenzylation gives composite (42) and on followed reaction with triphosgene treated benzyl protected naltrexol (Hamad, Kiptoo et al. 2006) (25) will give a new intermediate (43). Hydrogenolysis of (43) will give codrug-(9) (Scheme 8). Codrug-(10) will also be synthesized by using naltrexone (23) and triphosgene reagent.

Scheme-9

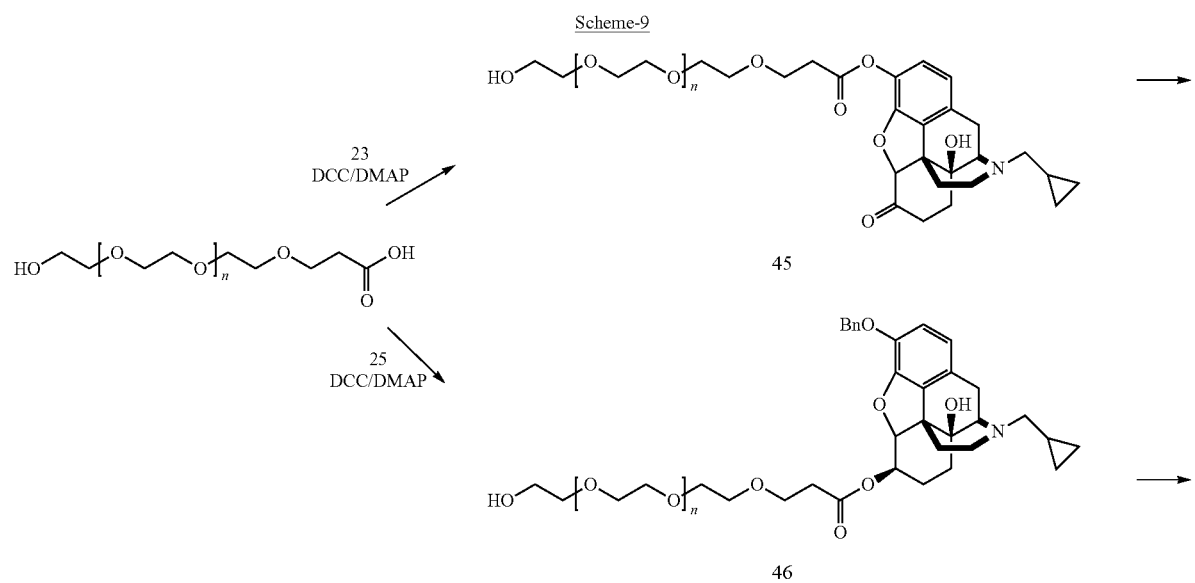

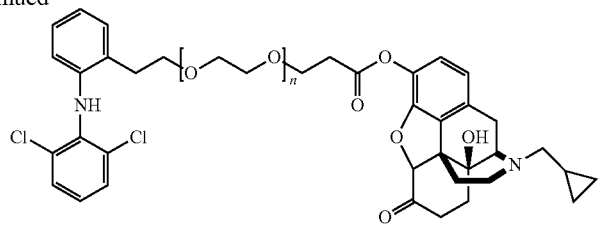

11

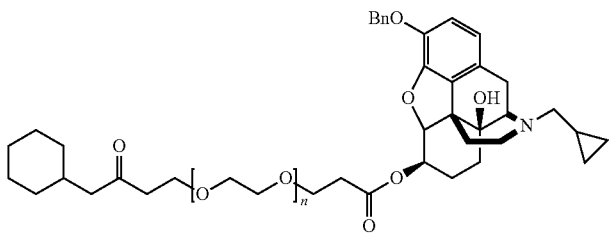

12

Pegylated codrugs-(11) and -(12) are designed based on reported studies (Bonina, Puglia et al. 2001) and will be synthesized as described in scheme-9. To avoid potential toxicity, the peg spacers will be used from n=4. Mono O-benzyl PEG spacer will be synthesized with small adaptation per the reported protocols (Bellouard, Chuburu et al. 1999), (Jiang and Yu 2008). PEG hydroxyl acid (44) on DCC coupling with naltrexone (23) will give peglylated naltrexone compound (45) and on further DCC coupling with diclofenac acid (22) will give PEG linked codrug-(11). By using benzyl protected naltrexol (25) PEG spacer linked diclofenac-naltrexol codrug-(12) will be synthesized.

Scheme-10

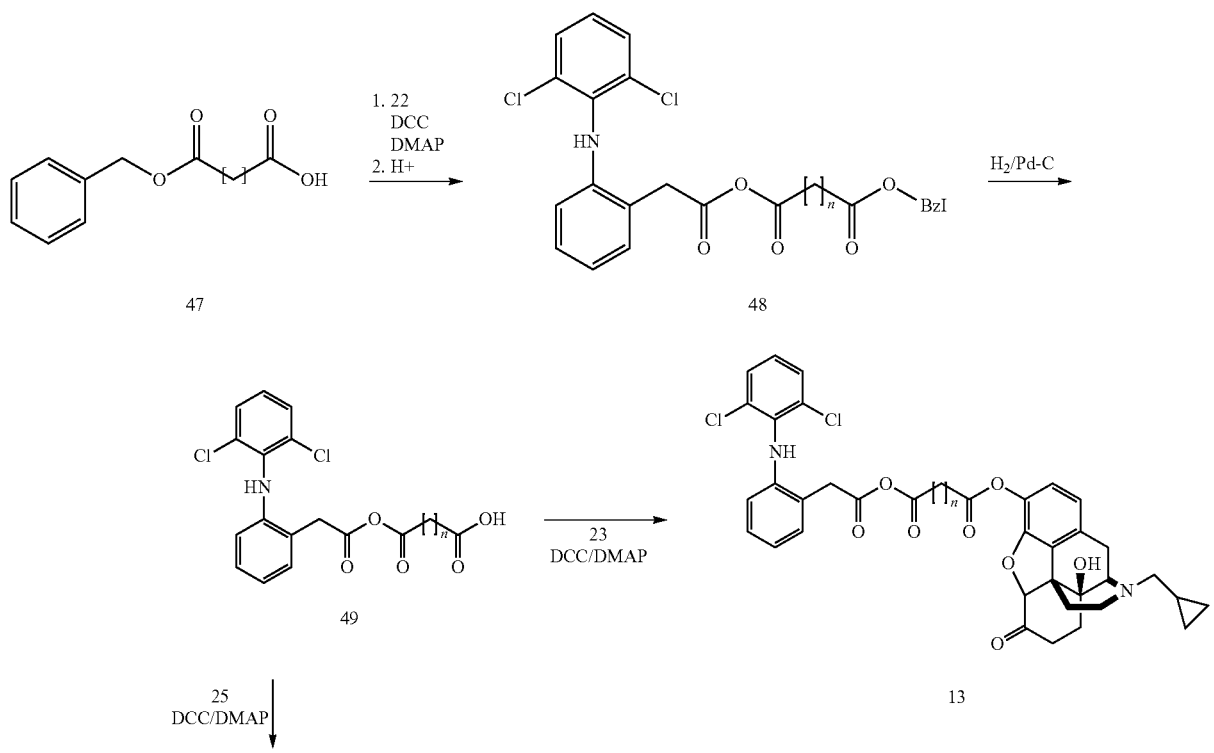

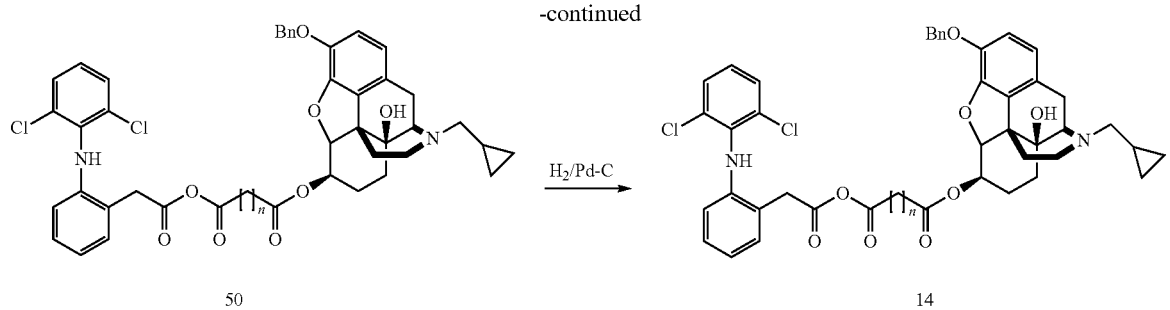

Anhydride codrugs are proposed based on research articles of diclofenac anhydride prodrugs (Mizrahi and Domb 2009). Mono benzyl protected dicarboxylic acids (47) will be used for synthesis of codrugs-(13) and -(14) as outlined in scheme-10. Debenzylation and DCC mediated coupling with naltrexone (23) will give codrug-(13). If starting materials are not commercially available they will be synthesized according to the following reference (Ballard, Richards et al. 2008). Diclofenac derivative (49) on DCC coupling with benzyl protected naltrexol (25) will give intermediate (50). This compound on hydrogenolysis will give codrug-(14).

Scheme-11

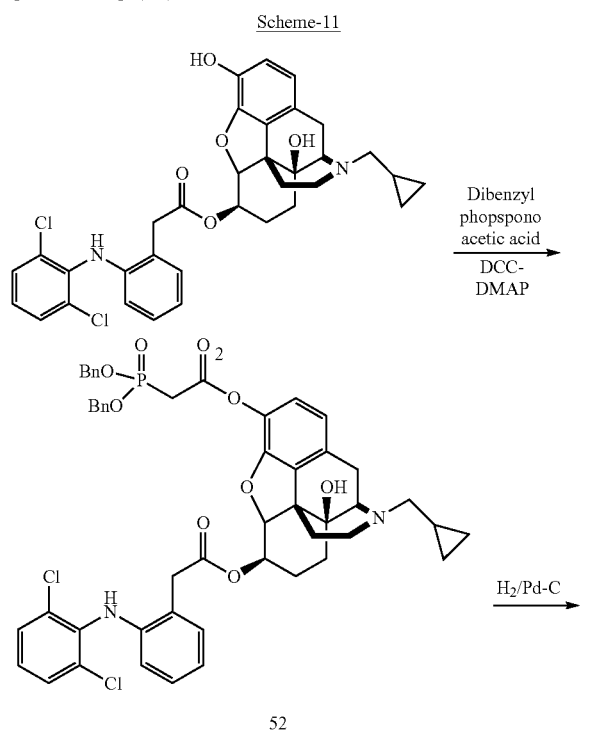

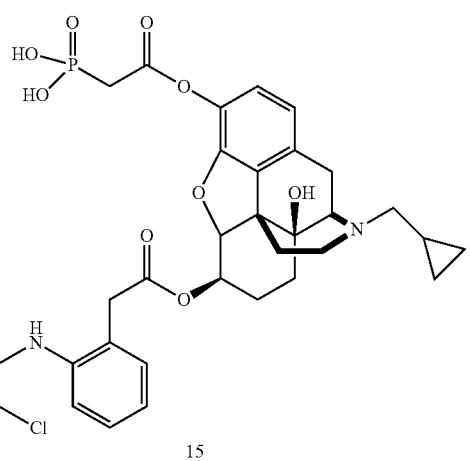

To increase the aqueous solubility, several codrugs are proposed in schemes-11-14. These codrugs are planned based on the following published research (Du, Hong et al. 2007), (Rouquayrol, Gaucher et al. 2001), (Baba and Yoshioka 2006). Water solubilizing phosphate, amino acid and L-malic acid moieties will be attached to phenolic hydroxy group of naltrexone (23) and aliphatic hydroxyl group of naltrexol (24). Naltrexol derivative in scheme-12 will be synthesized according to reported synthesis (Nelson, Davis et al. 1994).

Scheme-12

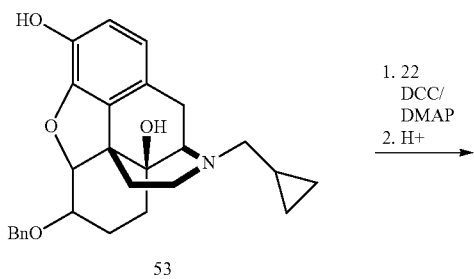

-continued
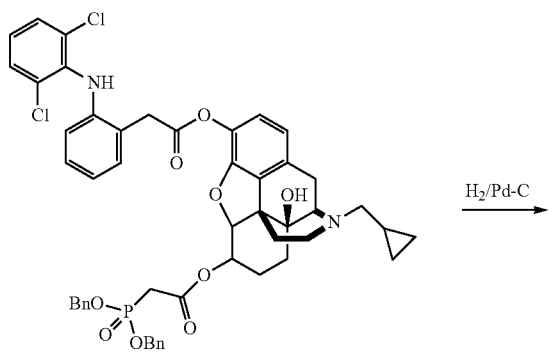
56
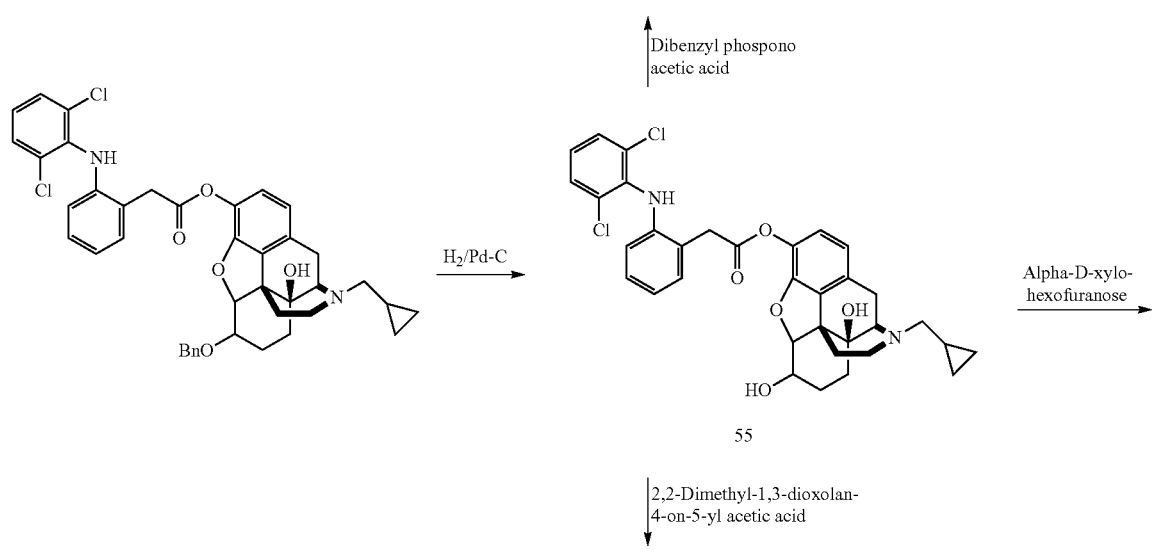
55
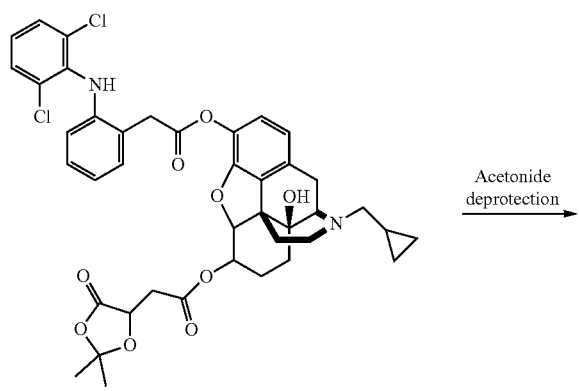
58

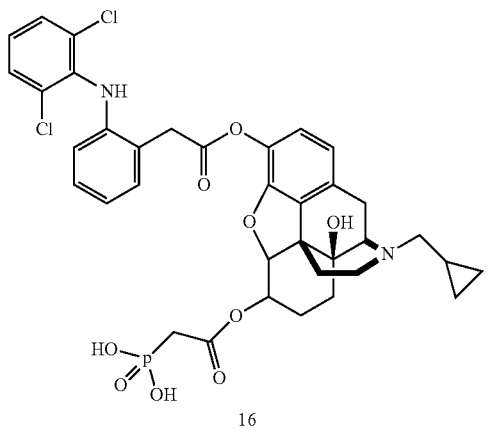
16
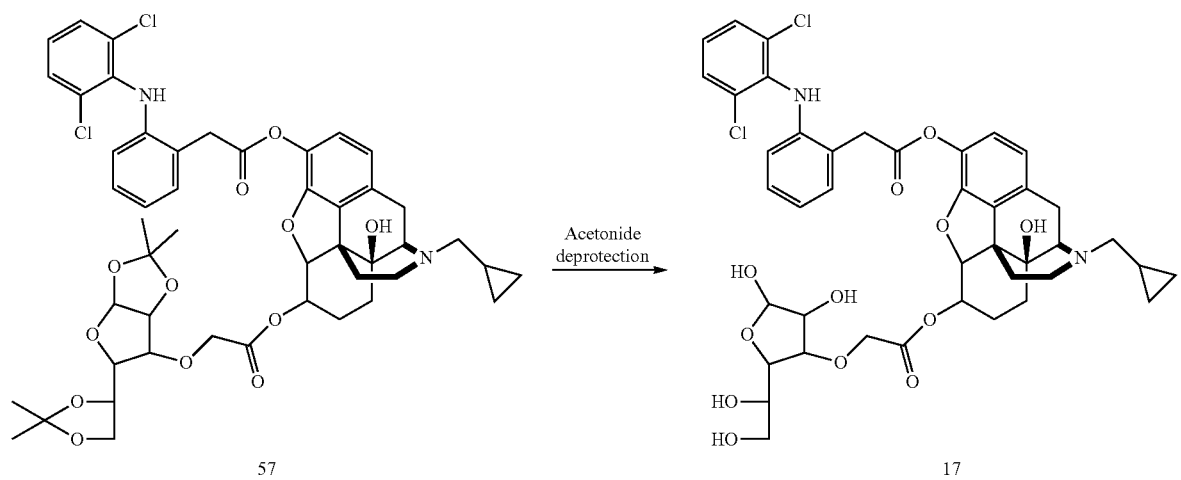
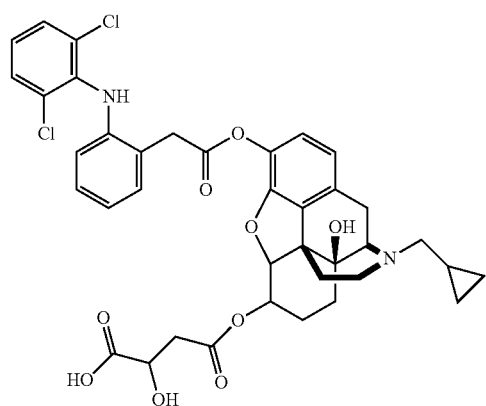
18

Scheme-13
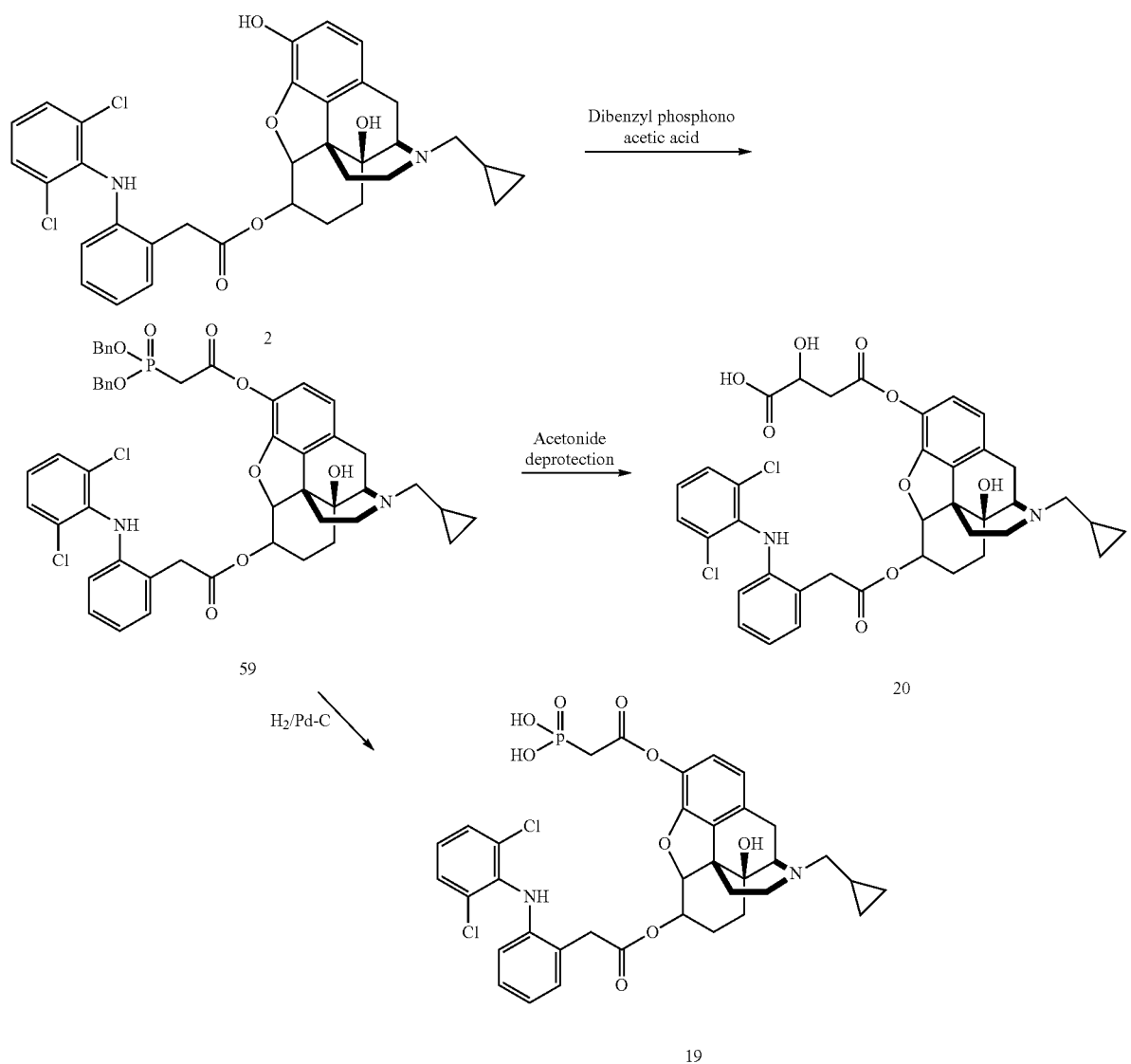
Final codrugs and all intermediate compounds will be completely characterized by $^1$HNMR, $^{13}$CNMR spectroscopy and mass spectrometry. All the codrugs will be converted to hydrochloride, glycolate and lactate salts according to mentioned reference (B. S. Somashekar 2005).
Scheme-14
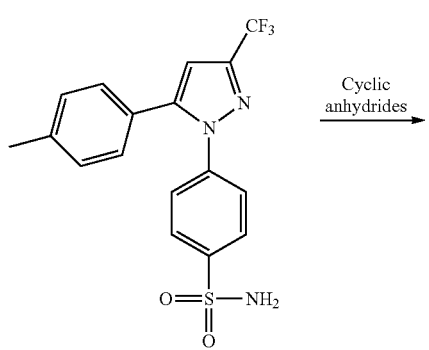

-continued

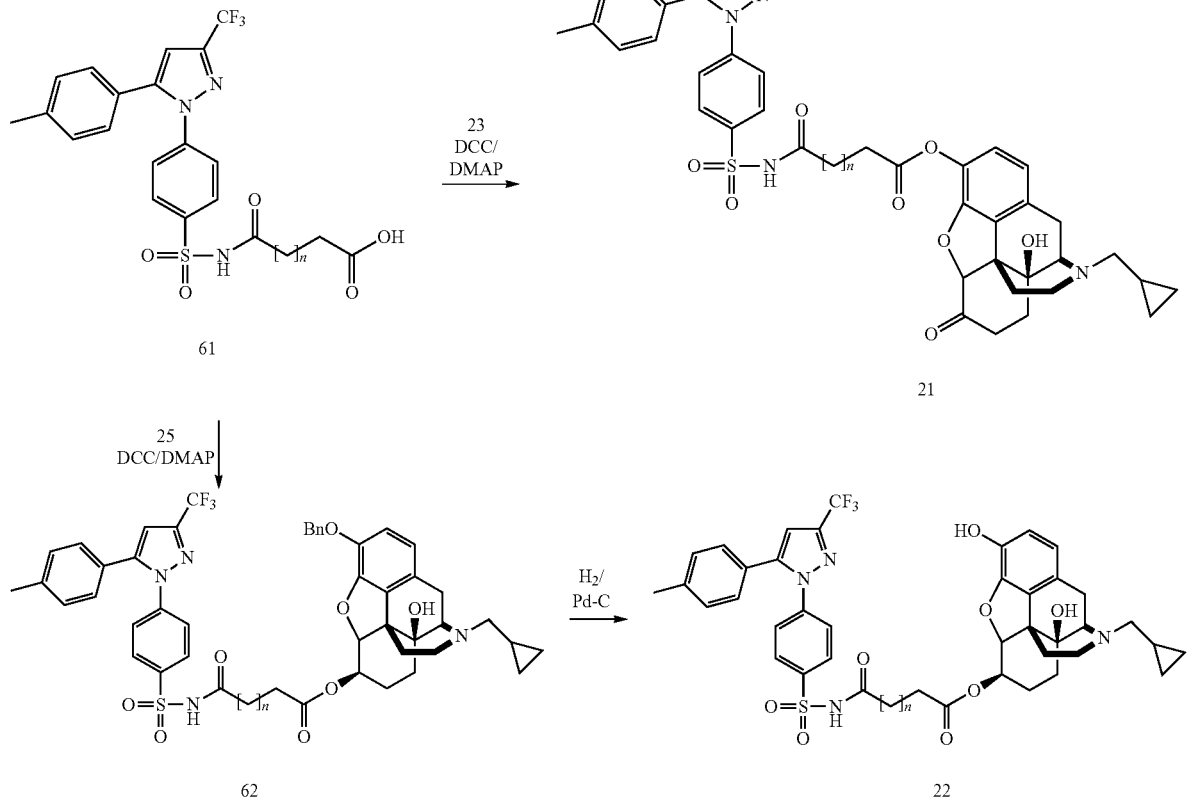

Celecoxib (60) will be reacted with different cyclic anhydrides to make intermediate (61), similar to some published protocols (Mantarosie, Coman et al. 2008), (Paun, Stere et al. 2008). Terminal carboxylic acid free compound (61) will attach to naltrexone (23) or benzyl protected naltrexol (25) to get target codrugs-21 and 22 (Scheme-14).

Example 2

The compound of FIG. 2U (Compound 2U) is studied.

Stability: The chemical stability of the compound in the pH 5.0 acetate buffer (0.3M) was 3.9±0.56 days and the enzymatic stability in the hairless guinea pig (HGP) plasma was 6.4±0.84 min (n=3) indicating that the compound would be degraded to regenerate the parent drugs as soon as it enters the body. In both the studies regeneration of the parents was observed with the degradation of the compound.

Figure 14A:
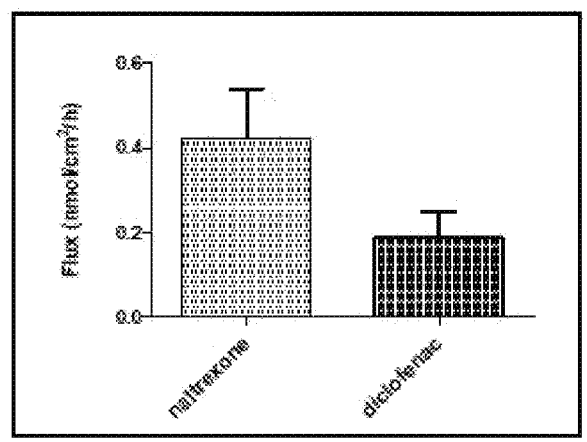
FIG. 14 In vitro diffusion study across full thickness Yucatan miniature pig skin of the base form of the compound of FIG. 2U (A) Steady state flux of naltrexone and diclofenac from the codrug at 48 hours post MN treatment. (n=3) (B) Skin concentration over time from the base form of the compound of FIG. 2U. Both naltrexone and diclofenac concentration could be observed in the skin indicating the regeneration of the parent molecules. n=3 for 12 h, 24 h and n=2 for 36 h and 48 h.
Figure 14B:
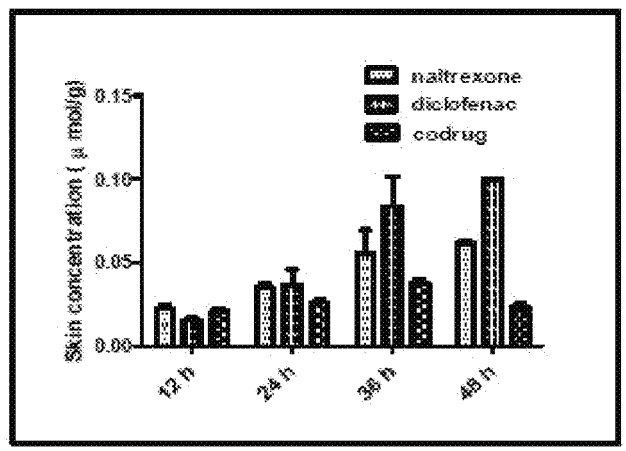

In vitro: The first in vitro experiments showed that the compound degraded in the skin to regenerate back the parent drugs even at 24 hours and amount of parent drugs from the compound increased with time. Steady state flux was obtained both from naltrexone and diclofenac of 0.42±0.12 nmol/(cm$^2$/hr) and 0.19±0.06 nmol/(cm$^2$/hr) respectively (FIG. 14A). The naltrexone flux was significantly higher compared to diclofenac (p<0.05). The skin concentration data is shown below in FIG. 14B. n=3 for flux calculation; n=2 for skin concentration studies at 36 and 48 hr timepoint and n=3 for 12 and 24 hr. (FIG. 14B).

Figure 15:
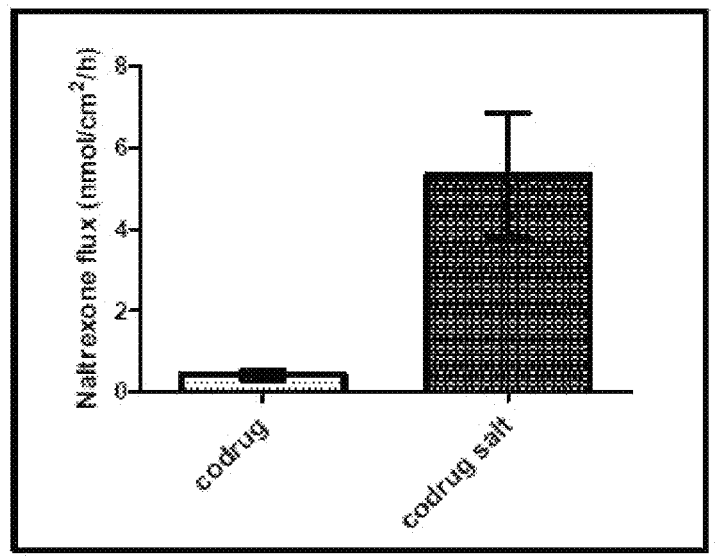
FIG. 15 In vitro diffusion study across full thickness Yucatan miniature pig skin comparing the base form on the codrug to the hydrochloride salt form. The steady state flux values of naltrexone are reported from codrug base (n=3) and codrug salt (n=4).

The flux of naltrexone from the hydrochloride salt form of the compound was 5.42±1.5 nmol/(cm$^2$/hr) compared to 0.42±0.12 nmol/(cm$^2$/hr) (p<0.005). The skin concentration for both naltrexone and the compound also increased. n=4 for the flux calculation. FIG. 15. So the flux increased by about 13 times using the salt form of the compound over the free base form.

Precipitation issues were observed with purely aqueous donor, so an in vitro formulation development experiment was carried out by varying the amount of PG in the donor. 10%, 25% and 50% PG was used with the salt form and it was observed that while there was no significant difference in flux between the aqueous formulation and 10% PG containing formulation (p<0.05), but flux decreased significantly for higher concentrations of PG. The data was compared using one way ANOVA and Tukey's posthoc analysis for pairwise multiple comparisons. The 10% PG containing formulation was hence chosen for in vivo studies. All experiments were carried out with a saturated donor solution.

In vivo experiments. The pores can be clearly visualized with gentian violet in FIG. 15 (A) immediately following MN treatment. In panel (B) the pores cannot be visualized at day 4 (96 h) pores treatment with MN followed by application of NTX HCl gel under occlusion. Pores can be visualized by India ink staining in panel C where the hydrochloride salt form of the compound was used following MN treatment indicating that the pores can stay open up to a 7 day time point.

The compound of FIG. 2V (Compound 2V) is studied.

Figure 18:
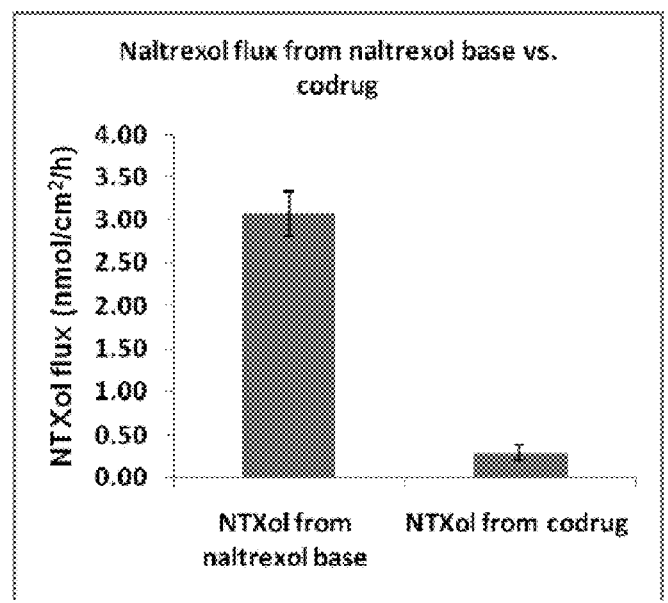
FIG. 18 is a graph showing flux of NTXol in a study involving the compound of FIG. 2V.
Figure 19:
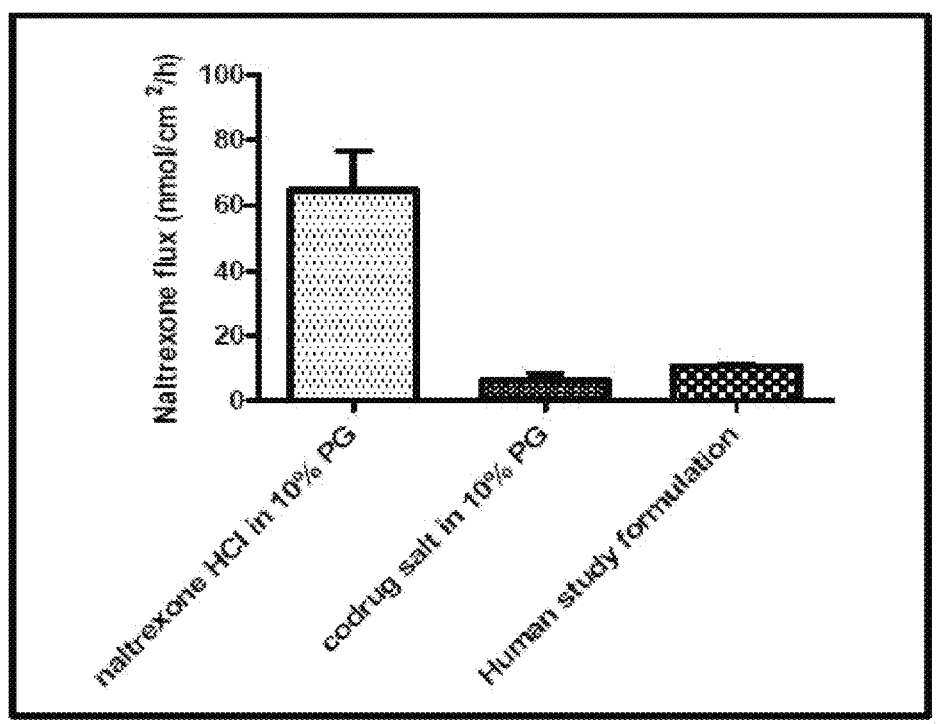
FIG. 19 In vitro diffusion study across full thickness Yucatan miniature pig skin comparing the flux of naltrexone at steady state from naltrexone HCl, salt form of the codrug and previously studied formulation for in vivo human pharmacokinetic studies (n>3).

Stability A chemical stability study was done for the compound 2 in 0.3M acetate buffer pH 5.0 at 32° C. The half life was approximately 56.3±9.5 days In vitro experiments The compound was tested in a 10% PG containing saturated donor formulation for in vitro flux and a naltrexol flux of approximately 0.29±0.09 nmol/cm$^2$/h was obtained from the compound compared to 3.07±0.27 nmol/cm$^2$/h naltrexol flux from 10% PG containing saturated naltrexol formulation. See FIG. 18.

The compound of FIG. 2W (Compound 2W) is studied.

A chemical stability study was done for the compound 2W in 0.3M acetate buffer

|  | Compound 2A | Compound 2B | Compound 2C |
|---|---|---|---|
| Chemical stability (days) | 3.9 ± 0.56 | 56.3 ± 9.5 | 37.08 ± 1.22 |
| Enzymatic stability (minutes) | 6.4 ± 0.84 min | — | — |

Methods:

For all in vitro experiments female Yucatan minipig skin (6 months old) were used. Skin sections were obtained by removing the subcutaneous fatty tissue by scalpel dissection, and were stored at −20° C. A PermeGear flow-through (In-Line, Riegelsville, Pa., USA) diffusion cell system was used for the skin permeation studies. Skin used for microneedle treatment was placed on a wafer of polydimethylsiloxane polymer, which mimicked the underlying mechanical support of tissue because of its comparable structural flexibility and elasticity.

The skin was pierced 20 times with an array containing 5 MN (i.e., to make a total of 100 individual and non-overlapping piercings) before mounting the skin in the diffusion cell for the treatment group. The insertion of MN into skin was carried out manually by applying gentle finger pressure followed by instantaneous removal. MN's were distributed evenly within the 0.95 cm$^2$ area of skin and could easily be visualized after each 5 MN insertion, as to prevent reapplication in the same area. Single MN array of 5 were used simply out of ease for the experimental procedure. If any damage to an MN section was observed the section was replaced. Cells containing MN treated skin showed no presence of receiver solution back flow into the donor compartment. Untreated skin samples were simply placed in the diffusion cells. Diffusion cells were kept at 32° C. using a circulating water bath. Data were collected using skin from a single pig 3-4 cells for the MN treated formulations.

The physiological receiver solution was water adjusted to pH 7.4 containing 20% ethanol, and the flow rate was adjusted to 1.5 ml/h. Each cell was charged with 0.25 ml of the donor in the donor compartment of the chamber. The diffusion cells were covered with a stopper to prevent evaporation. Samples were collected from the receiver compartment in six-hour increments over 48 h or for the length of the treatment. All samples were stored at 4° C. until analyzed by HPLC.

The skin samples at the end of the treatment period was removed, the treatment area was cut out with a scalpel and diced into small pieces. Extraction of drug was done by The transdermal occlusive protective covering patches were fabricated by sandwiching a rubber ringed barrier to create a reservoir between a drug-impermeable backing membrane (Scotchpak™ #1109 SPAK 1.34 MIL Heat Sealable Polyester Film) and an ARcare® 7396 adhesive around the edge of the rubber spacer. The impermeable backing laminate was adhered to the rubber retaining ringed barrier with 3M™ double sided tape. Finally, ARcare® 7396 was placed on the bottom of the rubber ringed barrier to maintain intimate contact with the skin and prevent evaporation of the 300 µL gel formulations.

Gel Formulations

4% w/w gels were prepared with the hydrochloride salt form of the compound for in vivo studies. Hydrochloride salt gels were formulated by dissolving 4% compound salt in propylene glycol: acetate buffer at pH 4.8-10:90 and 3.0% hydroxyethylcellulose polymer. As the polymer was dissolved over a 30 minute period, the solution was continuously stirred to ensure solvation as well as to initiate polymerization. The solution was stirred still a viscous gel resulted and then left at room temperature for 1½ to 2 hours to remove bubbles and ensure complete polymerization. The gel was saturated with excess solid and therefore was a cloudy gel.

Pharmacokinetic Animal Studies

Hairless IAF guinea pigs (Charles River) weighing 350-650 g were used for these studies. All animal studies were in accordance with the institutional guidelines and approved by the University of Kentucky IACUC. Surgical procedure was performed to canulate the jugular vein. Blood samples (0.3 mL) were drawn from the jugular vein at regular time intervals for the time studied. MN treated animals were first cleaned topically with isopropyl alcohol, and two 50 MN arrays were then manually applied to each dose site. For MN treated GPs, four 0.3 mL gel doses were applied to the dorsal region of the hairless guinea pigs at 4 sites to obtain steady state plasma levels. After application of the gel the skin was occluded with the patch and occlusive tape was applied to prevent evaporation of the formulation Blood samples were obtained for 7 days while the patch was changed with new formulation at 3.5 days. The blood samples were immediately centrifuged at 10,000×g for 3 min; plasma was separated and stored at −70° C. until analysis.

Staining

The patches were removed at predetermined time points and the site was cleaned with sterile gauze. Gentian violet/India ink was applied as the dyeing agent at the MN treated sites and allowed to dry before excess dye was removed with ethanol and gauze. Both the dyes stain the viable epidermis but not the intact SC. Hence, a grid is observed only in the presence of micropores in the skin, no staining is observed in its absence immersing the skin pieces in ACN overnight in a water bath shaker at 32° C. The donor was removed from the top of the skin at the end of the study and analyzed by direct injection onto HPLC after suitable dilution using ACN.

HPLC analysis. Quantitative analysis of naltrexone, diclofenac and the compound concentrations in all samples were carried out using a HPLC assay. The receiver samples were concentrated 10 fold with acetonitrile by evaporating 1 ml of the solution under nitrogen and reconstituting in 100 µl of ACN and injected into the HPLC. The skin samples were directly injected onto the HPLC. The HPLC system consisted of a Waters 717 plus autosampler, a Waters 600 quaternary pump, and a Waters 2487 dual wavelength absorbance detector with Waters Empower™ software. A Brownlee (Wellesley, Mass., USA) C-18 reversed phase Spheri-5 µm column (220×4.6 mm) with a C-18 reversed phase guard column of the same type (15×3.2 mm) by Perkin Elmer® was used with the UV detector set at a wavelength of 215 nm or 280 nm. The mobile phase consisted of 70:30 (v/v) ACN:(0.1% TFA with 0.065% 1-octane sulfonic acid sodium salt, adjusted to pH 3.0 with TEA aqueous phase). Samples were run at a flow rate of 1.5 ml/min with a run time of 8.5 min. The injection volume used was 25 µl for receiver samples and 100 µl for the skin samples. The retention time of naltrexone was 2.3 minutes, diclofenac was 3.5 minutes and compound was 6.5 minutes. Samples were analyzed within a linear range of standard curve for all the three compounds from 100-10000 ng/ml. The standard solutions exhibited excellent linearity over the entire concentration range employed in the assays. For the plasma samples the mobile phase consisted of 50:50 (v/v) ACN:(0.1% TFA with 0.065% 1-octane sulfonic acid sodium salt, adjusted to pH 3.0 with TEA aqueous phase). Samples were run at a flow rate of 1.0 ml/min with a run time of 37 minutes and injection volume of 10 µl. The retention time for naltrexone was 3.3 minutes, diclofenac was 16 minutes and compound was 33 minutes. Compound 2B and Compound 2C were detected using the same assay. The retention times were 5.8 and 4.3 minutes respectively.

In vivo experiments. Fabrication of transdermal patches
Transdermal Patches.

The transdermal occlusive protective covering patches were fabricated by sandwiching a rubber ringed barrier to create a reservoir between a drug-impermeable backing membrane (Scotchpak™ #1109 SPAK 1.34 MIL Heat Sealable Polyester Film) and an ARcare® 7396 adhesive around the edge of the rubber spacer. The impermeable backing laminate was adhered to the rubber retaining ringed barrier with 3M™ double sided tape. Finally, ARcare® 7396 was placed on the bottom of the rubber ringed barrier to maintain intimate contact with the skin and prevent evaporation of the 300 µL gel formulations.

Gel Formulations

4% w/w gels were prepared with the hydrochloride salt form of the compound for in vivo studies. Hydrochloride salt gels were formulated by dissolving 4% compound salt in propylene glycol: acetate buffer at pH 4.8-10:90 and 3.0% hydroxyethylcellulose polymer. As the polymer was dissolved over a 30 minute period, the solution was continuously stirred to ensure solvation as well as to initiate polymerization. The solution was stirred still a viscous gel resulted and then left at room temperature for 1½ to 2 hours to remove bubbles and ensure complete polymerization. The gel was saturated with excess solid and therefore was a cloudy gel.

Pharmacokinetic Animal Studies

Hairless IAF guinea pigs (Charles River) weighing 350-650 g were used for these studies. All animal studies were in accordance with the institutional guidelines and approved by the University of Kentucky IACUC. Surgical procedure was performed to canulate the jugular vein. Blood samples (0.3 mL) were drawn from the jugular vein at regular time intervals for the time studied. MN treated animals were first cleaned topically with isopropyl alcohol, and two 50 MN arrays were then manually applied to each dose site. For MN treated GPs, four 0.3 mL gel doses were applied to the dorsal region of the hairless guinea pigs at 4 sites to obtain steady state plasma levels. After application of the gel the skin was occluded with the patch and occlusive tape was applied to prevent evaporation of the formulation Blood samples were obtained for 7 days while the patch was changed with new formulation at 3.5 days. The blood samples were immediately centrifuged at 10,000×g for 3 min; plasma was separated and stored at 70 g C until analysis.

Staining

The patches were removed at predetermined time points and the site was cleaned with sterile gauze. Gentian violet/India ink was applied as the dyeing agent at the MN treated sites and allowed to dry before excess dye was removed with ethanol and gauze. Both the dyes stain the viable epidermis but not the intact SC. Hence, a grid is observed only in the presence of micropores in the skin, no staining is observed in its absence.

Example 3

Microneedle enhanced transdermal drug delivery enables the transport of a host of molecules that cannot be delivered across the skin by passive diffusion alone. However, the skin being a self-regenerating organ heals itself and thus prevents delivery of molecules across micropores for a seven day time period, the ideal transdermal delivery goal. Hence, it is necessary to employ a second drug molecule, a cyclooxygenase inhibitor to enhance pore lifetime by decreasing inflammatory response following microneedle treatment. A codrug approach using a 3-O-ester codrug of naltrexone, the model drug with diclofenac, a cyclooxygenase inhibitor was tested in vitro as well as in vivo to look at stability, bioconversion as well as permeation. The results indicate that the approach could be useful for transdermal drug delivery of naltrexone from a single patch for a week, but stability and solubility enhancement will be required before it can deliver therapeutically relevant levels of the drug. The skin concentration of diclofenac was high enough to keep the pores open in vivo in a hairless guinea pig model as evidenced by pore visualization studies.

INTRODUCTION

Transdermal drug delivery is a potential alternative route for a host of drug molecules that are difficult to deliver via the oral or parenteral route. It avoids first pass effects, hepatotoxicity, gastric irritation issues as well as needlephobia. However, only small, lipophilic molecules can be delivered by passive diffusion alone across the stratum corneum (SC), the main barrier to transdermal drug delivery (Prausnitz, et al. (2004), Prausnitz and Langer (2008)). Hence, physical and chemical enhancement techniques are being used to enhance the number the molecules that can be delivered via this route. Physical enhancement techniques include iontophoresis, electroporation, low frequency ultrasound and microneedle (MN) enhanced delivery. Chemical enhancement techniques include chemical enhancers and the prodrugs/codrugs approach. In this study MN enhanced delivery was combined with a codrug approach to develop a seven day sustained release patch system. MN is a minimally invasive physical enhancement technique. The method adopted is the "poke and patch" approach[3] where solid stainless steel MN arrays are used to create micropores (also referred to as micro channels) across the SC. The MN is then removed and a matrix/reservoir type patch is applied to deliver drugs through the micropores. Pain associated with the application of these MNs is also negligible when compared to a hypodermic needle (Kaushik, et al., (2001), Gill, et al. (2008)) which could potentially lead to better compliance, one of the major drawbacks of addiction therapy (O'Malley, et al. (1992)).

Naltrexone (NTX), the model compound (M.W of 341.41, log P of 1.8) is one of the leading FDA approved pharmacotherapy for alcohol addiction. It is a µ-opioid receptor antagonist and is known to decrease alcohol craving in recovering addicts. The drug exerts its mechanism of action by attenuating the ethanol induced stimulation of the mesolimbic-dopaminergic pathway (Lee, et al. (2005), Swift (2010)). Currently, NTX is marketed as a 50 mg once daily oral formulation, Revia® (Naltrexone Hydrochloride). This has compliance issues in addicts Hulse and Bosso (2000), Volpicelli (1997). It also has an oral bioavaibility ranging from 5-40% and is associated with side effects like hepatotoxicity, nausea and vomiting (1996, PDR. 2d Ed, New Jersey, Medical Economics). The intramuscular injectable 28 day controlled release formulation of NTX; Vivitrol™ was approved by the FDA in 2006. Injection site reactions and difficulty of removal in case of emergency opiate treatment in addition to the above are some of the major drawbacks of this dosage form (Alkermes, Vivitrol Alert). 6-β naltrexol is the major metabolite of NTX and has a higher half-life of 13 hours in plasma compared to that of 4 hours for NTX. It has been shown to be an effective therapy for alcohol abuse as well (McCaul, et al., (2000)).

NTX cannot be delivered in relevant therapeutic concentrations transdermally by passive delivery alone. Some of the earlier efforts in the laboratory have looked at delivery of NTX via the prodrugs and codrugs approach. The results indicated that although flux enhancement was achieved in vitro in some cases, the flux enhancement was not enough to deliver the molecule in therapeutically relevant concentrations in vivo (Hammell, et al. (2004), Haranath, et al. (2005), Kiptoo, et al. (2008)). Using MN it has been shown both in vitro as well as in vivo that NTX can be delivered in the lower therapeutic range of 2 ng/ml Banks, et al. (2008), Wermeling, et al. (2008), Verebey, et al. (1976)). However, one of the issues with this approach is that the micropores begin to close between 48-72 hour (Wermeling, et al. (2008), Banks, et al. (2010), Kalluri and Banga (2011). Therefore, in order to develop a 7 day patch system, pore lifetime enhancement techniques need to be employed along with MN for successful therapy.

Different techniques can be used to delay barrier recovery after MN treatment. The skin is a self-regulatory organ and employs different methods for recovery after assault. Cutaneous wound healing itself consists of multiple phases, inflammatory response being the first step. Increased synthesis and secretion of lamellar body contents and transformation into bilayer is also a part of the recovery process (Feingold (2002), Feingold, et al. (2000), Menon, et al. (1992). Occlusion alone can also delay the recovery process by decreasing the water flux across the barrier, one of the major signals for recovery of structure and function (Grubauer et al. (1989)).

Figure 11:
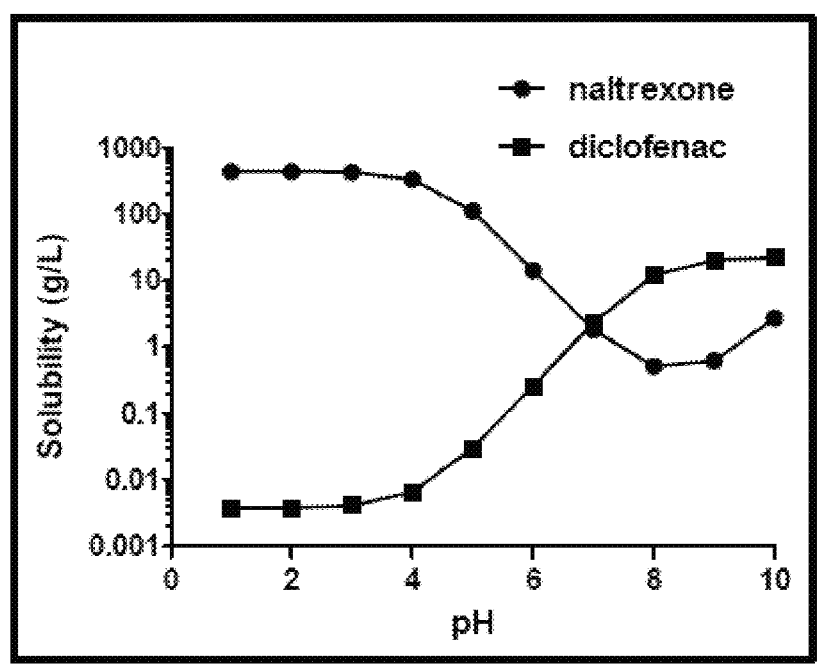
FIG. 11 Solubility profile of naltrexone and diclofenac generated using predicted chemical property values from Scifinder®.

There are several literature reports indicating the increase in expression of both COX-1 and COX-2 following damage to the skin and the role of, both the enzymes in cutaneous repair (Fecker, et al. (2007), Davidson and Breyer (2003), Muller-Decker, et al. (2002), Futagami, et al. (2000)). Diclofenac (DIC) is a NSAID that nonselectively inhibits both COX-1 and COX-2 thereby preventing formation of downstream products like prostaglandins and thromboxane, thus decreasing inflammation. It is currently available on the market as an oral as well as topical formulation and is the first choice of NSAID for this project. Previous experiments showed that by daily application of Solaraze Gel® (3% diclofenac sodium, 2.5% hyaluronic acid) after one time application of MN was able to deliver NTX over the seven day time period in hairless guinea pig (HGP) (Banks, et al. (2011). Daily application is irrational for a patch system and co formulating the drugs in high concentration at a pH optimum of 5 (pH of the outer layer of the skin is 4.5-5.5)[32] is difficult because the drugs have different physicochemical properties (FIG. 11). This leads to the codrug approach. The 3-O-ester-codrug contains a biolabile ester linkage that can be cleaved by hydrolytic enzymes like esterase as soon as it reaches the epidermal region of the skin to release the parent compounds (Vaddi, et al. (2009), Prusakiewicz, et al. (2006), Oesch, et al. (2007). Once in the skin the DIC will act locally to keep the pores open while NTX is delivered systemically. The overall objective of this paper is to use a codrug approach to reduce the inflammatory response in combination with occlusion for delayed barrier recovery following MN treatment to reach the ultimate goal of a seven day patch system.

Materials and Methods
Chemicals

Naltrexone HCl was purchased from Mallinckrodt (St. Louis, Mo.), diclofenac acid from AK Scientific, Inc. (Mountain view, CA) and diclofenac sodium salt from TCI America (Portland, Oreg.). Water was purified using NANOpure Diamond™, Barnstead water filtration system. Hanks' balanced salts modified powder, propylene glycol and ethanol, 200 proof were purchased from Sigma (St. Louis, Mo.). 4-(2-Hydroxyethyl)-1-piperazineethanesulfonic acid (HEPES), sodium bicarbonate, sodium acetate, acetic acid and gentamicin sulfate and were obtained from Fisher Scientific (Fairlawn, N.J.). 1-Octanesulfonate, sodium salt was obtained from Regis Technologies, Inc (Morton Grove, Ill.). Trifluoroacetic acid (TFA), triethylamine (TEA) and acetonitrile (ACN) were obtained from EMD chemicals (Gibbstown, N.J.). Natrosol® (hydroxyethylcellulose) was obtained from Hercules. Chemicals for codrug synthesis were purchased from Alfa Aessar.

Synthetic Procedure for Codrug

Diclofenac sodium salt was dissolved in 1:1 (Ethyl acetate:Water) mixture and acidified with concentrated hydrochloric acid. Organic layer was separated and aqueous layer treated with ethyl acetate two times. Combined organic layer was dried on anhydrous sodium sulfate and rotary evaporated to remove reaction solvents. Diclofenac free acid was activated with DCC (N, N'-Dicyclohexyl carbodiimide)) and DMAP (4-Dimethylaminopyridine) in anhydrous tetrahydrofuran. After two hours, equivalent naltrexone was added in dry tetrahydrofuran. Combined reactants were allowed to stir over night under nitrogen atmosphere. After completion of the reaction, solvents were removed under reduced pressure and reaction crude mixture purified by flash silica gel column chromatography eluting with 80% ethyl acetate and 20% cyclohexane and codrug-1 was obtained in 56% (Scheme-1) yield. The codrug-1 was dissolved in 1, 4-dioxane and an equimolar amount of 2M hydrochloric acid in dioxane was added and refluxed for 1.5 hrs, and precipitated with hexanes to get hydrochloride salt of codrug-24 (Scheme-1)

$^1$HNMR (CDCl$_3$, 300 MHz): δ 7.29 (m, 2H), 7.19 (t, 1H), 6.93 (m, 2H), 6.75 (d, 1H), 6.60 (d, 2H), 6.57 (d, 1H), 4.78 (s, 1H), 3.67 (s, 2H), 3.12 (m, 2H), 2.79 (m, 1H), 2.32 (t, 2H), 2.27 (m, 2H), 2.05 (m, 2H), 1.69 (m, 2H), 1.62, (m, 2H), 0.46 (m, 1H), 0.31 (m, 2H), 0.30 (m, 2H)

$^{13}$CNMR(CDCl$_3$, (300 MHz): δ 4.22, 4.41, 9.77, 23.31, 31.09, 31.59, 36.45, 38.50, 43.75, 51.01, 59.48, 62.15, 70.28, 90.93, 118.75, 119.52, 122.45, 123.05, 124.19, 124.31, 128.30, 128.97, 129.73, 130.38, 130.64, 131.31, 132.63, 138.09, 142.92, 147.77, 169.98, 207.67

HRMS: Calculated for $C_{34}H_{32}O_5N_2Cl_2$ 618.1688 and found 618.1697.

Hydrochloride Salt of Codrug-24

$^1$HNMR (CDCl$_3$, 300 MHz): δ9.98 (bs, NH$^+$) 7.33 (m, 2H), 7.13 (t, 1H), 6.99 (m, 3H), 6.61 (d, 1H), 6.57 (d, 1H), 4.97 (s, 1H), 4.73 (s, 1H), 4.10 (s, 2H), 3.60 (m, 2H), 3.14 (m, 4H), 2.92 (m, 1H), 2.65 (m, 2H), 2.41 (d, 1H), 1.82 (m, 3H), 1.25 (m 2H), 0.84 (m, 4H), 0.62 (m, 1H)

Quantitative Analysis

NTX, DIC and the codrug concentrations in all samples were quantified using a HPLC assay which is a modified version of the previously reported NTX assay (Milewski and Stinchcomb (2011)). The HPLC system consisted of a Waters 717 plus auto sampler, a Waters 600 quaternary pump, and a Waters 2487 dual wavelength absorbance detector with Waters Empower™ software. A Perkin Elmer Spheri5 VL C18 column (5μ, 220×4.6 mm), a C18 guard column (15×3.2 mm) was used with the UV detector set at a wavelength of 280 nm. The mobile phase consisted of 70:30 (v/v) ACN:(0.1% TFA with 0.065% 1-octane sulfonic acid sodium salt, adjusted to pH 3.0 with TEA aqueous phase). Samples were run at a flow rate of 1.5 ml/min with a run time of 8.5 min. The injection volume used was 25 μl for receiver samples and 100 μl for the skin samples. For the plasma samples the mobile phase consisted of 50:50 (v/v) ACN:(0.1% TFA with 0.065% 1-octane sulfonic acid sodium salt, adjusted to pH 3.0 with TEA aqueous phase). Samples were run at a flow rate of 1.0 ml/min with a run time of 37 minutes and injection volume of 25 μl.

Chemical and Enzymatic Stability

Chemical and enzymatic stability was determined for the codrugs. For chemical stability studies, the codrug was put in prewarmed 0.3M acetate buffer pH 5.0 after solubilization in <5% ACN, if required, at 32° C. in an incubator. Samples were withdrawn at regular intervals and injected into the HPLC after appropriate dilutions. Enzymatic stability studies are important for estimation of conversion of codrugs in the plasma. For plasma stability studies prewarmed HGP plasma at 37° C. was spiked with codrug solution and samples were withdrawn at regular intervals. 100 μl of plasma sample was extracted with 1 ml of 1:1 ACN:ethyl acetate, vortexed, centrifuged at 10,000 rpm for 20 minutes on a bench top Eppendorf Mini Spin®. The supernatant was decanted into a glass tube and evaporated under nitrogen. Samples were reconstituted in 100 μl ACN and injected onto the HPLC. All stability data was analyzed using pseudo first order kinetics. All stability studies were carried out at least, in triplicate.

In Vitro Diffusion Studies

The in vitro permeation experiments were carried out to determine the transdermal flux of the parent drugs and the codrug, permeation coefficients as well as the concentration of the drug molecules in the skin at the end of the study. For all in vitro experiments Yucatan miniature pig (YP) skin was used. Full thickness skin was obtained by removing the subcutaneous fatty tissue by scalpel dissection, and stored at −20° C. A PermeGear flow-through (In-Line, Riegelsville, Pa., USA) diffusion cell system was used for the skin permeation studies. Skin for MN treatment was placed on a wafer of polydimethylsiloxane polymer, which mimics the underlying mechanical support of tissue because of its comparable structural flexibility and elasticity. The skin was pierced 20 times with a 5 MN array (making 100 individual and non-over lapping piercings) before mounting the skin in the diffusion cell. MN pores were distributed evenly within the 0.95 cm$^2$ area of skin. Untreated skin samples were mounted directly onto the diffusion cells. The setup was maintained at 32° C. using a circulating water bath. Data collected using a minimum of 3-4 cells per treatment group. The receiver solution was water alkalified to pH 7.4 containing 20% ethanol at 37° C. Gentamycin sulfate (50 mg/L) was added to the receiver for 7 day studies as an antibacterial agent. The receiver flow rate was adjusted to 1.5 ml/h to maintain skin conditions. Each cell was charged with 0.25 ml of the donor and the diffusion cells were covered with a stopper to prevent evaporation of formulation. Samples were collected at regular increments over 48 hours or for the length of the treatment. Drug was concentrated 10 fold by evaporating 1 ml of the collected sample under nitrogen and reconstituting in 100 μl of ACN for quantification. All samples were stored at 4° C. until analyzed by HPLC. The skin was removed at the end of the study and the treatment area was diced into small pieces using a scalpel after removing all excess drugs from top of the skin. Drug was extracted out by immersing the skin pieces in ACN overnight in a shaker water bath at 32° C. Samples were injected into the HPLC after appropriate dilution for quantitative analysis. The donor was also removed and quantified at the end of the study by direct injection onto HPLC after suitable dilution using ACN. All data was analyzed using Fick's first law of diffusion. $J_{ss}=P*\Delta C$ where $J_{ss}$ is the steady state flux, P is the permeability coefficient and $\Delta C$ is the concentration difference between the donor and the receiver. Since the receiver is maintained at sink conditions $\Delta C$ is essentially the concentration of the donor. Steady state flux is obtained from a plot of cumulative amounts permeated per time. Permeability coefficients can be calculated using the known donor concentration.

In Vivo Studies

Fabrication of Transdermal Patches

The transdermal patches were fabricated by sandwiching a blend of nitrile rubber and polyvinyl chloride plastic ring barrier to create a reservoir between the skin and the impermeable backing membrane (Scotchpak™ #1109 SPAK 1.34 MIL Heat Sealable Polyester Film) and an ARcare® 7396 adhesive around the edge of the rubber spacer. 3M™ double sided tape was used on either side of the rubber to attach the backing on one side and to maintain contact with the skin on the other side and prevent evaporation of the formulation.

Dose Preparation and Application

All animal experiments were approved by the University of Kentucky IACUC. A proof of concept in vivo experiment was carried out. 4% w/w gels were prepared with the hydrochloride salt form of the codrug. Gels were formulated by dissolving 4% codrug salt in PG: buffer at pH 5.0=10:90 and 3.0% hydroxyethylcellulose (HEC) polymer (required to have a gel formulation). Polymer was dissolved over a 30 minute period to obtain a homogenous gel. The solution was stirred until a viscous gel resulted and then left at room temperature for 1½ to 2 hours to remove bubbles and ensure complete polymerization. The gel was saturated with excess solid and therefore was cloudy. MN treated animals were first cleaned topically with isopropyl alcohol, and 50 MN array was applied twice mutually perpendicular to each other to give a total of 100 pores at each site. 0.3 mL gel doses were applied to the dorsal region of the HGP. After application of the gel the skin was occluded with the occlusive patch and biocclusive tape was applied to prevent evaporation of the formulation. The patch was changed with new formulation at 3.5 days such that more than 50% intact codrug was always present in formulation. A control experiment was also carried out to look at the effect of NTX HCl alone in the same vehicle on pore closure kinetics. A 9% solution of NTX HCl was used to prepare a 3% HEC gel and all other methods of application were constant with the codrug gel. The patches were removed to obtain data at successive 24 h time intervals.

Staining

The patches were removed at predetermined time points and the site was cleaned with sterile gauze. Gentian violet/India ink was applied as the dyeing agent at the MN treated sites and allowed to dry before excess dye was removed with ethanol and gauze. Both the dyes stain the viable epidermis but not the intact SC. Hence, a grid is observed only in the presence of micropores in the skin, no staining is observed in its absence.

Statistical Analysis

Data for all experiments are reported as mean±standard deviation. Statistical analysis of data will be carried out with Students' t-test and one way ANOVA with post hoc Tukey's pairwise tests, if required, using SIGMA-STAT (SPSS, Inc., Chicago, Ill., USA) software. P<0.05 will be considered to be statistically significant.

Results and Discussion

Synthesis. The codrug and it's hydrochloride salt were synthesized successfully. The structures were verified.

HPLC method development. HPLC assay development for the parent drugs and the codrug was the first step towards quantification of the data. The retention time of NTX was 2.3 minutes, DIC was 3.5 minutes and codrug was 6.5 minutes. The retention time for the same compounds in plasma samples were 3.3 minutes, 16 minutes and 33 minutes. All retention times reported are value±0.1 minutes. Samples were analyzed within a linear range of standard curve for all the three compounds from 100-10000 ng/ml. The standard solutions exhibited excellent linearity over the entire concentration range employed in the assays.

Stability studies. The chemical and enzymatic stability data indicated that the chemical half-life of the codrug in the pH 5.0 buffer was 3.9±0.56 days and the enzymatic half-life in the HGP plasma was 6.4±0.84 minutes. In both the studies regeneration of the parents were observed with the degradation of the codrug. The chemical stability indicates that the codrug is not stable enough in an aqueous formulation for the development of a 7-day transdermal drug delivery system. But still it could be utilized as a learning tool for understanding the bioconversion of the codrug in the epidermal region of the skin as well as for proof of concept that the codrug methodology could work to enhance the drug delivery window following one time application of the MN. The plasma stability study indicates that even if intact codrug permeates the skin and reaches the systemic circulation it would cleave back to the parent drugs almost immediately thus contributing to the naltrexone flux. The systemic concentration of diclofenac should not be of concern since it would be orders of magnitude lower compared to therapeutically relevant systemic doses.

In vitro experiments. The goal of the first set of in vitro experiments was to estimate flux and skin concentration of the base form of the codrug. A saturated donor solution was used consisting of propylene glycol (PG):ethanol: water=43:43:14 and had a concentration of 4.5 mg/ml. 4 treatment groups each having 3 diffusion cells (MN treatment) were dosed and then cells were removed every 12 hours to obtain the skin concentration of the parent drugs as well as the codrug at different timepoints. An intact skin control was also present for the entire length of the study (48 hours). Steady state flux was obtained both from NTX and DIC of 0.42±0.12 nmol/(cm$^2$/h) and 0.1910.06 nmol/(cm$^2$/h) respectively (FIG. 14A). The flux of NTX was significantly higher compared to the flux of DIC (p<0.05). The skin concentration data shows that the codrug degraded in the skin to regenerate back the parent drugs even at 24 hours and amount of parent drugs from the codrug increased with time. It also showed that the DIC increased in the skin with time and was higher compared to the NTX at 48 hours.

The codrug cleaved, and NTX flux was obtained from the base form of the codrug, although it was not high enough to produce therapeutic efficacy. As also noted from the flux and skin concentration data, significantly higher amounts of naltrexone was found in the receiver while diclofenac was retained in the skin in higher concentration at 48 h. This difference in flux and skin concentration could be attributed to the difference in physicochemical properties of the drug molecules. While naltrexone is positively charged at the skin surface pH of 5 (ref), at least 90% of the diclofenac will be negatively charged. Since skin is known to possess a negative charge due to presence of negatively charged carboxylic acid groups this might lead to slower migration and higher retention of diclofenac molecules in the skin. Since the hypothesis behind the project is based on the fact that diclofenac would work locally to reduce subclinical inflammatory response thus enhancing the drug delivery window, this characteristic of the molecules would be beneficial in the long term.

From literature it is known that a charged species has higher flux through MN treated skin compared to a non-treated control. This property is attributed to the enhanced solubility of a charged species in an aqueous donor rather than the molecular species itself (Banks, et al. (2008). Viscosity of the donor formulation also has a predominant effect on the flux across MN treated skin where it has been shown that 17 fold flux enhancement was obtained using a low viscosity, aqueous donor compared to a high viscosity propylene glycol (PG) rich donor (concentration was maintained at 110 mg/ml). No significant difference in flux was observed across untreated intact skin using the above donors. Hence the hydrochloride salt form of the codrug was tested for higher solubility and flux in aqueous donor for subsequent experiments.

Figure 12:
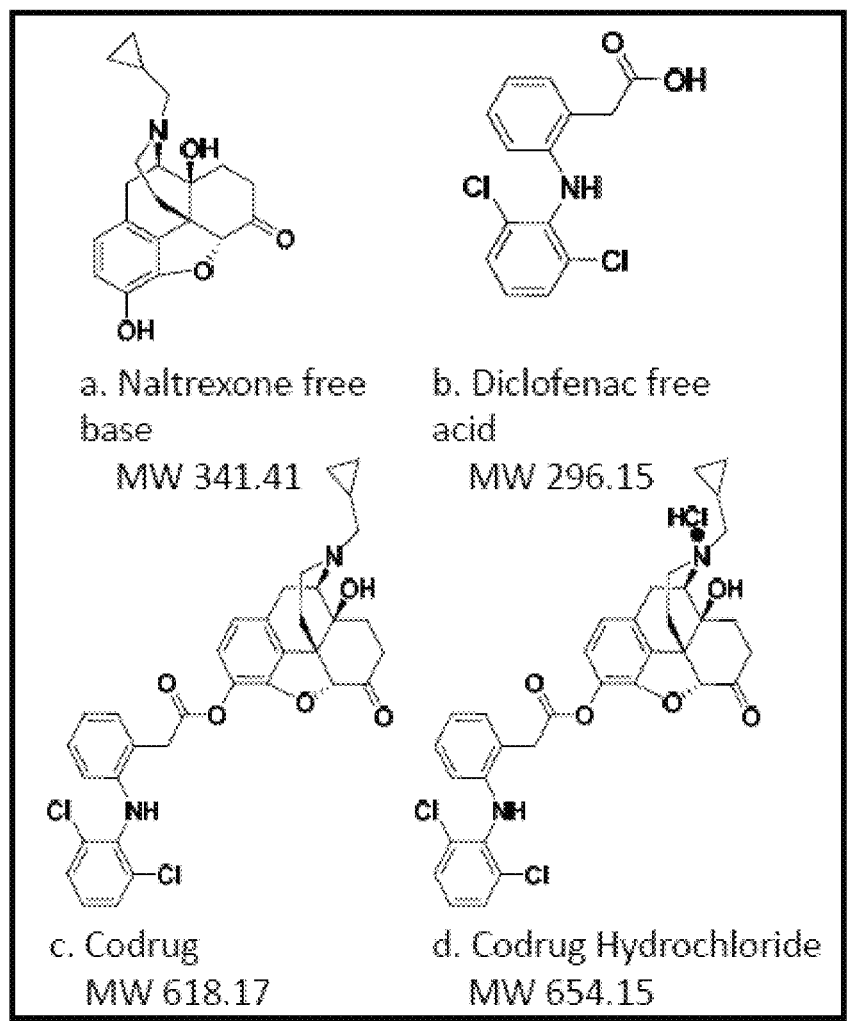
FIG. 12 Structure of parent drugs, (a) naltrexone, (b) diclofenac (c) 3-O-ester codrug and (d) hydrochloride salt form of 3-O-ester codrug.
Figure 13:
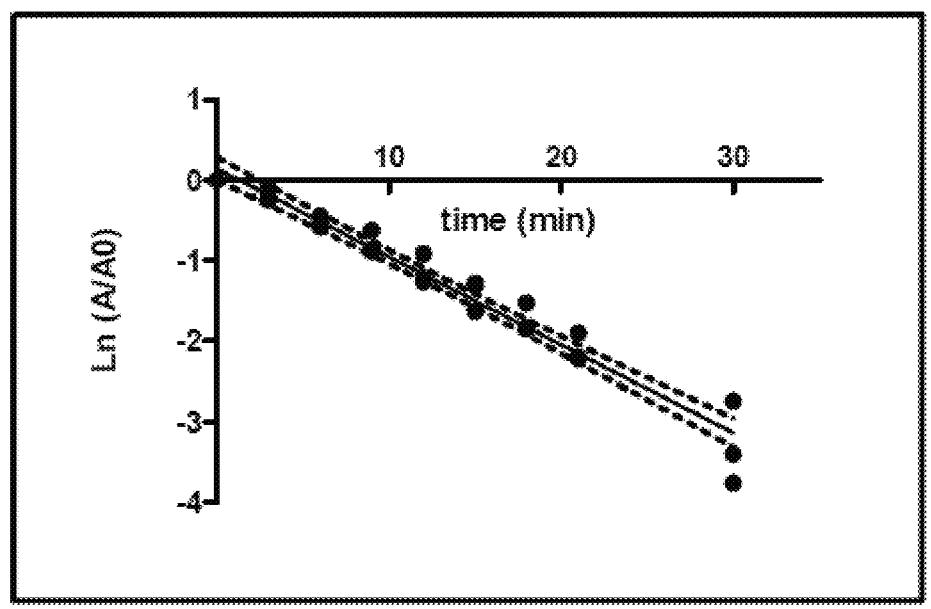
FIG. 13 Stability study profile for codrug in hairless guinea pig plasma indicating pseudo first order kinetics. (n=3).
Figure 16:
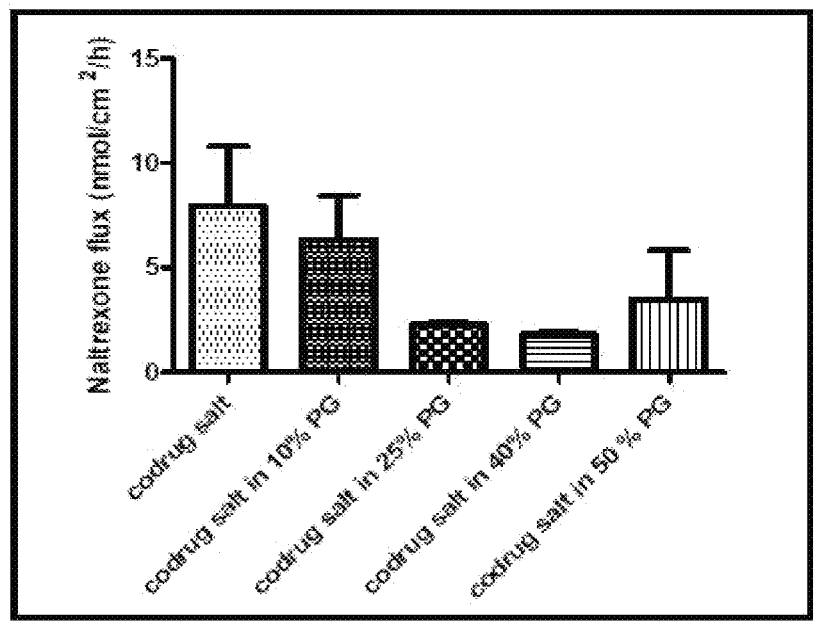
FIG. 16 includes a graph showing flux of naltrexone from different formulations of the compound of FIG. 2U. In vitro diffusion study across full thickness Yucatan miniature pig skin comparing the flux of naltrexone at steady state from different donor formulations. Propylene glycol (PG) was used in different concentrations to optimize formulation for in vivo studies (n≥3)

In the next set of experiment hydrochloride salt of codrug (FIG. 12) was used as the donor solution with a concentration of 39.3 mg/ml in 0.3M acetate buffer at pH 5.0. The flux of NTX from the codrug salt was 5.42±1.5 nmol/(cm$^2$/h) (FIG. 16) and the skin concentration for both NTX and the codrug increased (data not shown). Therefore a 13 fold flux enhancement was obtained by using the salt form over the free base form (p<0.005) which can be attributed to the solubility enhancement of the salt form in an aqueous donor.

Precipitation issues were observed with purely aqueous donor, so in vitro formulation development experiment was carried out by varying the amount of PG in the donor. 10%, 25% and 50% PG was used with the salt form and it was observed that while there was no significant difference in flux between the aqueous formulation and 10% PG containing formulation (p<0.05), but flux decreased significantly for higher concentrations of PG. All experiments were carried out with saturated donor solution. The data was compared using one way ANOVA and Tukey's posthoc analysis for pair wise multiple comparisons. The 10% PG containing formulation was hence chosen for in vivo studies.

Figure 17:
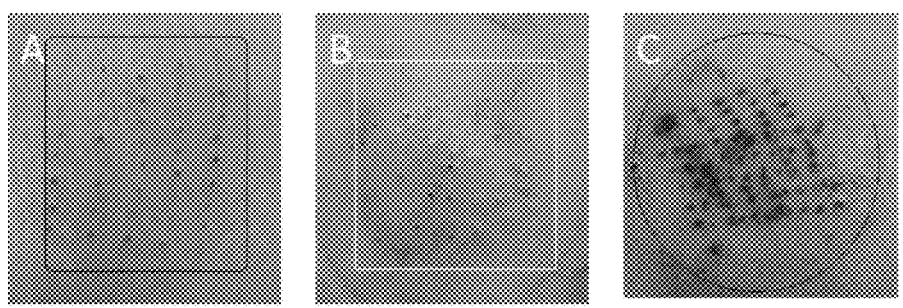
FIG. 17 is a series of pictures of visualized hairless guinea pig micropores (A) immediately following MN treatment, (B) at day 4 following treatment with MN followed by application of NTX HCl gel under occlusion, and (C) visualized by India ink staining wherein the HCl salt form of the compound was used following MN treatment indicating that the pores can stay open up to a 7 day time point.

In vivo studies. The pores can be clearly visualized with gentian violet in FIG. 17 (A) immediately following MN treatment. In panel (B) the pores cannot be visualized at day 4 (96 h) pores treatment with MN followed by application of NTX HCl gel under occlusion. This is in agreement with previously reported data in pharmacokinetic studies where it has been shown that the micropores close anywhere between a 48-72 h timeline following MN treatment under occlusion (Stan PNAS ref). Pores can be visualized by India ink staining in panel C where the hydrochloride salt form of the codrug was used following MN treatment indicating that the pores can stay open up to a 7 day time point. Therefore, it can be concluded from the studies that the codrug is effective in keeping the pores open analogous to our hypothesis.

From the studies so far it can be concluded that the codrug cleaved back to parent drugs both in stability studies as well as in vitro studies. The salt form of the codrug improved solubility and flux significantly in in vitro studies. Subsequent in vivo studies with the salt form in an optimized 10% PG containing formulation kept the pores open for a 7 day target drug delivery window but the flux of NTX from the codrug was not high enough to quantify in an hairless guinea pig model. This could be predicted from clearance estimation from previous pharmacokinetic studies with NTX in the same animal model based on size of treated area since $$J_{ss}*A=C_{ss}*Cl$$

In this case with 4 patches A is 400 MN treatments, flux is 5.5 nmol/cm$^2$/h and Cl is 5.6 L/h which leads to a Css of around 1 ng/ml, the LLOQ on the LCMS assay. Hence reliable pharmacokinetic data could not be obtained from this codrug. Hence, physicochemical optimization is required to obtain a molecule that would have higher stability and permeability in a range that can be clinically applicable, thus making the codrug approach applicable for pore lifetime enhancement and NTX delivery.

Codrugs will possess a variety of different linking groups of diverse susceptibility to hydrolysis including carboxylate ester, carbamate ester and carbonate ester. A nontoxic linker moiety will be used in between, if required (e.g. polyethylene glycol, alkyl chain). It has been shown that the ionized form of the drug has a much higher flux compared to the unionized form via the MN pathway. This phenomenon is mainly due to enhanced solubility of the ionized species in formulation (Banks, et al. (2008).

The main rate limiting step of the codrug approach is the synthesis of the complex codrugs as well as the stability in formulation. Solubility issues in an aqueous medium might also be rate limiting since most of the codrugs have a very high predicted log P value.

The theoretical flux values required for NTX in vitro to achieve therapeutically relevant concentrations in vivo is around 12-90 nmol/cm$^2$/h from a 25 cm$^2$ patch, based on the oral dosing regimen. On the other hand the flux of DIC required to have any systemic effect is almost an order of magnitude higher. Thus, DIC related systemic toxicity should not be an issue with this design.

In an aqueous environment codrugs should have a lower chemical stability, since it undergoes hydrolysis in formulation, but higher solubility leading to higher flux via a microchannel pathway (Banks, et al. (2008). Hence a hydrochloride salt form was used to enhance solubility and permeation. The viscosity of the donor solution has also been shown to have an effect on MN enhanced delivery (Milewski and Stinchcomb (2011)). So optimization based on formulation viscosity was carried out by adding different concentrations of propylene glycol (PG) to the codrug salt in an aqueous vehicle.

Throughout this document, various references are mentioned. All such references are incorporated herein by reference to the same extent as if each individual reference was specifically and individually indicated to be incorporated by reference, including the references set forth in the following list:

REFERENCES

1. Banks S L, Hamad M, Pinninti R, Gill H S, Crooks P A, Prausnitz M R and Stinchcomb A L (2010) Transdermal delivery of naltrexol and skin permeability lifetime after microneedle treatment in hairless guinea pigs *Journal of Pharmaceutical Sciences* 99(7):3072-3080.
2. Banks S L, Paudel K S, Brogden N K, Loftin C D and Stinchcomb A L (2011) Diclofenac Enables Prolonged Delivery of Naltrexone Through Microneedle-Treated Skin. *Pharm Res* 28(5):1211-1219.
3. Banks S L, Pinninti R R, Gill H S, Crooks P A, Prausnitz M R and Stinchcomb A L (2008) Flux across [corrected] microneedle-treated skin is increased by increasing charge of naltrexone and naltrexol in vitro. *Pharm Res* 25(7):1677-1685.
4. Barr C S, Chen S A, Schwandt M L, Lindell S G, Sun H, Suomi S J and Heilig M (2010) Suppression of alcohol preference by naltrexone in the rhesus macaque: a critical role of genetic variation at the micro-opioid receptor gene locus. *Biol Psychiatry* 67(1):78-80.
5. Breese G R, Chu K, Dayas C V, Funk D, Knapp D J, Koob G F, Le D A, O'Dell L E, Overstreet D H, Roberts A J, Sinha R, Valdez G R and Weiss F (2005) Stress enhancement of craving during sobriety: a risk for relapse. *Alcohol Clin Exp Res* 29(2):185-195.
6. Casswell S and Thamarangsi T (2009) Reducing harm from alcohol: call to action. *Lancet* 373:2247-2257.
7. Cone E J, Gorodetzky C W and Yeh S Y (1974) The urinary excretion profile of naltrexone and metabolites in man. *Drug Metab Dispos* 2(6):506-512.
8. Cynkowski T, Cynkowska G and Walters K A (2008) Codrugs: potential therapies for dermatological diseases. *Dermatologic, Cosmeceutic, and Cosmetic Development:* 255-266.
9. Epperson C N, Toll B, Wu R, Amin Z, Czarkowski K A, Jatlow P, Mazure C M and O'Malley S S (2010) Exploring the impact of gender and reproductive status on outcomes in a randomized clinical trial of naltrexone augmentation of nicotine patch. *Drug Alcohol Depend* 112(1-2): 1-8.
10. Ferrari A, Bertolotti M, Dell'Utri A, Avico U and Sternieri E (1998) Serum time course of naltrexone and 6 beta-naltrexol levels during long-term treatment in drug addicts. *Drug Alcohol Depend* 52(3):211-220.
11. Fortin J P, Ci L, Schroeder J, Goldstein C, Montefusco M C, Peter I, Reis S E, Huggins G S, Beinbom M and Kopin A S (2010) The mu-opioid receptor variant N190K is unresponsive to peptide agonists yet can be rescued by small-molecule drugs. *Mol Pharmacol* 78(5):837-845.
12. Garbutt J C (2010) Efficacy and tolerability of naltrexone in the management of alcohol dependence. *Curr Pharm Des* 16(19):2091-2097.
13. Garbutt J C, Kranzler H R, O'Malley S S, Gastfriend D R, Pettinati H M, Silverman B L, Loewy J W and Ehrich E W (2005) Efficacy and tolerability of long-acting injectable naltrexone for alcohol dependence: a randomized controlled trial. *Jama* 293(13):1617-1625.
14. Grant J E, Odlaug B L and Kim S W (2010) A double-blind, placebo-controlled study of N-acetyl cysteine plus naltrexone for methamphetamine dependence. *Eur Neuropsychopharmacol* 20(11):823-828.
15. Greenway F L, Dunayevich E, Tollefson G, Erickson J, Guttadauria M, Fujioka K and Cowley M A (2009) Comparison of combined bupropion and naltrexone therapy for obesity with monotherapy and placebo. *J Clin Endocrinol Metab* 94(12):4898-4906.
16. Greenway F L, Fujioka K, Plodkowski R A, Mudaliar S, Guttadauria M, Erickson J, Kim D D and Dunayevich E (2010) Effect of naltrexone plus bupropion on weight loss in overweight and obese adults (COR-I): a multicentre, randomised, double-blind, placebo-controlled, phase 3 trial. *Lancet* 376(9741):595-605.
17. Gueorguieva R, Wu R, Donovan D, Rounsaville B J, Couper D, Krystal J H and O'Malley S S (2010) Naltrexone and combined behavioral intervention effects on trajectories of drinking in the COMBINE study. *Drug Alcohol Depend* 107(2-3):221-229.
18. Haggkvist J, Lindholm S and Franck J (2009a) The effect of naltrexone on amphetamine-induced conditioned place preference and locomotor behaviour in the rat. *Addict Biol* 14(3):260-269.
19. Haggkvist J, Lindholm S and Franck J (2009b) The opioid receptor antagonist naltrexone attenuates reinstatement of amphetamine drug-seeking in the rat. *Behav Brain Res* 197(1):219-224.
20. Ioannides-Demos L L, Piccenna L and McNeil J J (2011) Pharmacotherapies for obesity: past, current, and future therapies. *J Obes* 2011:179674.
21. Kalluri H and Banga A (2009) Microneedles and transdermal drug delivery. *Journal of Drug Delivery Science and Technology* 19(5):303-310.
22. Karila L, Weinstein A, Aubin H J, Benyamina A, Reynaud M and Batki S L (2010) Pharmacological approaches to methamphetamine dependence: a focused review. *Br J Clin Pharmacol* 69(6):578-592.
23. Kaushik S, Hord A H, Denson D D, McAllister D V, Smitra S, Allen M G and Prausnitz M R (2001) Lack of pain associated with microfabricated microneedles. *Anesth Analg* 92(2):502-504.
24. Kiptoo P K, Hamad M O, Crooks P A and Stinchcomb A L (2006) Enhancement of transdermal delivery of 6-beta-naltrexol via a codrug linked to hydroxybupropion. *J Control Release* 113(2):137-145.
25. Kiptoo P K, Paudel K S, Hammell D C, Hamad M O, Crooks P A and Stinchcomb A L (2008) In vivo evaluation of a transdermal codrug of 6-beta-naltrexol linked to hydroxybupropion in hairless guinea pigs. *Eur J Pharm Sci* 33(4-5):371-379.
26. Koob G F and Le Moal M (2005) Plasticity of reward neurocircuitry and the 'dark side' of drug addiction. *Nat Neurosci* 8(11):1442-1444.
27. Kranzler H R and Edenberg H J (2010) Pharmacogenetics of alcohol and alcohol dependence treatment. *Curr Pharm Des* 16(19):2141-2148.
28. Kranzler H R, Modesto-Lowe V and Van Kirk J (2000) Naltrexone vs. nefazodone for treatment of alcohol dependence. A placebo-controlled trial. *Neuropsychopharmacology* 22(5):493-503.
29. Mark T L, Kassed, C. A., Vandivort-Warren, R. Levit, K. R., & Kranzler, H. R. (2009) Alcohol and opioid dependence medications: Prescription trends, overall and by physician specialty. *Drug and Alcohol Dependence* 99:345-349.
30. Martinotti G, Di Nicola M, Tedeschi D, Andreoli S, Reina D, Pomponi M, Mazza M, Romanelli R, Moroni N, De Filippis R, Di Giannantonio M, Pozzi G, Bria P and Janiri L (2010) Pregabalin versus naltrexone in alcohol dependence: a randomised, double-blind, comparison trial. *J Psychopharmacol* 24(9):1367-1374.
31. McAllister D V, Wang P M, Davis S P, Park J H, Canatella P J, Allen M G and Prausnitz M R (2003) Microfabricated needles for transdermal delivery of macromolecules and nanoparticles: fabrication methods and transport studies. *Proc Natl Acad Sci USA* 100(24):13755-13760.
32. McCaul M E, Wand G S, Eissenberg T, Rohde C A and Cheskin L J (2000a) Naltrexone alters subjective and psychomotor responses to alcohol in heavy drinking subjects. *Neuropsychopharmacology* 22(5):480-492.
33. McCaul M E, Wand G S, Rohde C and Lee S M (2000b) Serum 6-beta-naltrexol levels are related to alcohol responses in heavy drinkers. *Alcohol Clin Exp Res* 24(9):1385-1391.
34. Meyer M C, Straughn A B, Lo M W, Schary W L and Whitney C C (1984) Bioequivalence, doseproportionality, and pharmacokinetics of naltrexone after oral administration. *J Clin Psychiatry* 45(9 Pt 2):15-19.
35. Milewski M, Brogden N K and Stinchcomb A L (2010a) Current aspects of formulation efforts and pore lifetime related to microneedle treatment of skin. *Expert Opin Drug Deliv* 7(5):617-629.
36. Milewski M and Stinchcomb A L (2010) Vehicle composition influence on the microneedle-enhanced transdermal flux of naltrexone hydrochloride. *Pharm Res* Epub ahead of print
37. Milewski M and Stinchcomb A L (2011) Vehicle composition influence on the microneedle-enhanced transdermal flux of naltrexone hydrochloride. *Pharm Res* 28(1):124-134.
38. Milewski M, Yerramreddy T R, Ghosh P, Crooks P A and Stinchcomb A L (2010b) In vitro permeation of a pegylated naltrexone prodrug across microneedle-treated skin. *Journal of Controlled Release* 146(1):37-44.
39. Mokdad A H, Marks J S, Stroup D F and Gerberding J L (2004) Actual causes of death in the United States, 2000. *JAMA* 291(10):1238-1245.
40. Morley K C, Teesson M, Sannibale C, Baillie A and Haber P S (2010) Clinical predictors of outcome from an Australian pharmacological relapse prevention trial. *Alcohol Alcohol* 45(6):520-526.
41. O'Malley S S (1996) Opioid antagonists in the treatment of alcohol dependence: clinical efficacy and prevention of relapse. *Alcohol Alcohol* 31 Suppl 1:77-81.
42. O'Malley S S, Jaffe A J, Chang G, Schottenfeld R S, Meyer R E and Rounsaville B (1992) Naltrexone and coping skills therapy for alcohol dependence. A controlled study. *Arch Gen Psychiatry* 49(11):881-887.
43. Paudel K S, Nalluri B N, Hammell D C, Valiveti S, Kiptoo P, Hamad M O, Crooks P A and Stinchcomb A L (2005) Transdermal delivery of naltrexone and its active metabolite 6-beta-naltrexol in human skin in vitro and guinea pigs in vivo. *J Pharm Sci* 94(9):1965-1975.
44. Pettinati H M, Oslin D W, Kampman K M, Dundon W D, Xie H, Gallis T L, Dackis C A and O'Brien C P (2010) A Double-Blind, Placebo-Controlled Trial Combining Sertraline and Naltrexone for Treating Co-Occurring Depression and Alcohol Dependence. *Am J Psychiatry*.
45. Pillai O, Hamad M O, Crooks P A and Stinchcomb A L (2004) Physicochemical evaluation, in vitro human skin diffusion, and concurrent biotransformation of 3-O-alkyl carbonate prodrugs of naltrexone. *Pharm Res* 21(7):1146-1152.
46. Potts R O, Bommannan D, Wong O, Tamada J A, Riviere J E and Monteiro-Riviere N A (1997) Transdermal peptide delivery using electroporation. *Pharm Biotechnol* 10:213-238.
47. Potts R O and Guy R H (1992) Predicting skin permeability. *Pharm Res* 9(5):663-669.
48. Prausnitz M R and Langer R (2008) Transdermal drug delivery. *Nat Biotechnol* 26(11):1261-1268.
49. Ray L A, Chin P F and Miotto K (2010a) Naltrexone for the treatment of alcoholism: clinical findings, mechanisms of action, and pharmacogenetics. *CNS Neurol Disord Drug Targets* 9(1):13-22.

50. Ray L A, Hutchison K E, Ashenhurst J R and Morrow A L (2010b) Naltrexone selectively elevates GABAergic neuroactive steroid levels in heavy drinkers with the ASP40 allele of the OPRM1 gene: a pilot investigation. *Alcohol Clin Exp Res* 34(8):1479-1487.
51. Reece A S (2011) Hypothalamic opioid-melanocortin appetitive balance and addictive craving. *Med Hypotheses* 76(1): 132-137.
52. Rehm J, Mathers C, Popova S, Thavorncharoensap M, Teerawattananon Y and Patra J (2009) Global burden of disease and injury and economic cost attributable to alcohol use and alcoholuse disorders. *Lancet* 373(9682): 2223-2233.
53. Roberts W J and Sloan K B (1999) Correlation of aqueous and lipid solubilities with flux for prodrugs of 5-fluorouracil, theophylline, and 6-mercaptopurine: A Potts-Guy approach. *J Pharm Sci* 88(5):515-522.
54. Roche D J, Childs E, Epstein A M and King A C (2010) Acute HPA axis response to naltrexone differs in female vs. male smokers. *Psychoneuroendocrinology* 35(4):596-606.
55. Rukstalis M R, Stromberg M F, O'Brien C P and Volpicelli J R (2000) 6-beta-naltrexol reduces alcohol consumption in rats. *Alcohol Clin Exp Res* 24(10):1593-1596.
56. Schuckit M (2009) Alcohol-use disorders. *Lancet* 373: 492-501.
57. Shaw D and al'Absi M (2010) Blunted opiate modulation of prolactin response in smoking men and women. *Pharmacol Biochem Behav* 95(1):1-5.
58. Sinha R (2007) The role of stress in addiction relapse. *Curr Psychiatry Rep* 9(5):388-395.
59. Soyka M and Rosner S (2010) Emerging drugs to treat alcoholism. *Expert Opin Emerg Drugs* 15(4):695-711.
60. Stinchcomb A L, Dua R, Paliwal A, Woodard R W and Flynn G L (1995) A solubility and related physicochemical property comparison of buprenorphine and its 3-alkyl esters. *Pharm Res* 12(10):1526-1529.
61. Stinchcomb A L, Swaan P W, Ekabo O, Harris K K, Browe J, Hammell D C, Cooperman T A and Pearsall M (2002) Straight-chain naltrexone ester prodrugs: diffusion and concurrent esterase biotransformation in human skin. *J Pharm Sci* 91(12):2571-25781
62. Strasinger C L, Scheff N N and Stinchcomb A L (2008) Prodrugs and codrugs as strategies for improving percutaneuos absorption. *Expert Review of Dermatology* 3(2): 221-233.
63. Vaddi H K, Banks S L, Chen J, Hammell D C, Crooks P A and Stinchcomb A L (2009) Human skin permeation of 3-O-alkyl carbamate prodrugs of naltrexone. *J Pharm Sci* 98(8):2611-2625.
64. Vaddi H K, Hamad M O, Chen J, Banks S L, Crooks P A and Stinchcomb A L (2005) Human skin permeation of branched-chain 3-O-alkyl ester and carbonate prodrugs of naltrexone. *Pharm Res* 22(5):758-765.
65. Valiveti S, Hammell D C, Paudel K S, Hamad M O, Crooks P A and Stinchcomb A L (2005a) In vivo evaluation of 3-O-alkyl ester transdermal prodrugs of naltrexone in hairless guinea pigs. *J Control Release* 102(2): 509-520.
66. Valiveti S, Paudel K S, Hammell D C, Hamad M O, Chen J, Crooks P A and Stinchcomb A L (2005b) In vitro/in vivo correlation of transdermal naltrexone prodrugs in hairless guinea pigs. *Pharm Res* 22(6):981-989.
67. Verebey K, Volavka J, Mule S J and Resnick R B (1976) Naltrexone: disposition, metabolism, and effects after acute and chronic dosing. *Clin Pharmacol Ther* 20(3): 315-328.
68. Volpicelli J R, Alterman A I, Hayashida M and O'Brien C P (1992) Naltrexone in the treatment of alcohol dependence. *Arch Gen Psychiatry* 49(11):876-880.
69. Volpicelli J R, Rhines K C, Rhines J S, Volpicelli L A, Alterman A I and O'Brien C P (1997) Naltrexone and alcohol dependence. Role of subject compliance. *Arch Gen Psychiatry* 54(8):737-742.
70. Wall M E, Brine D R and Perez-Reyes M (1981) Metabolism and disposition of naltrexone in man after oral and intravenous administration. *Drug Metab Dispos* 9(4):369-375.
71. Wermeling D P, Banks S L, Hudson D A, Gill H S, Gupta J, Prausnitz M R and Stinchcomb A L (2008) Microneedles permit transdermal delivery of a skin-impermeant medication to humans. *Proc Natl Acad Sci USA* 105(6):2058-2063.
72. WHO (2004) Global status report on alcohol 2004., in *World Health Organization*, Geneva.
73. Yu C D, Fox J L, Ho N F H and Higuchi W I (1979) Physical Model Evaluation of Topical Prodrug Delivery—Simultaneous Transport and Bioconversion of Vidarabine-5'-Valerate 0.1. Physical Model Development. *Journal of Pharmaceutical Sciences* 68(11):1341-1346.
74. Zarkin G A, Bray J W, Aldridge A, Mills M, Cisler R A, Couper D, McKay J R and O'Malley S (2010) The effect of alcohol treatment on social costs of alcohol dependence: results from the COMBINE study. *Med Care* 48(5):396-401.
75. B. S. Somashekar, G. A. N. G., A. R. Ramesha and C. L. Khetrapal (2005). "Protonation of trimipramine salts of maleate, mesylate and hydrochloride observed by $^1$H, $^{13}$C and $^{15}$N NMR spectroscopy." *MAGNETIC RESONANCE CHEMISTRY* 43: 166-170.
76. Baba, A. and T. Yoshioka (2006). "Synthesis of 1-beta-O-acyl glucuronides of diclofenac, mefenamic acid and (S)-naproxen by the chemo-selective enzymatic removal of protecting groups from the corresponding methyl acetyl derivatives." *Organic & Biomolecular Chemistry* 4(17): 3303-3310.
77. Ballard, T. E., J. J. Richards, et al. (2008). "Synthesis and Antibiofilm Activity of a Second-Generation Reverse-Amide Oroidin Library: A Structure-Activity Relationship Study." *Chemistry-a European Journal* 14(34): 10745-10761.
78. Bellouard, F., F. Chuburu, et al. (1999). "A convenient synthetic route to polyether-tagged cyclam ligands and their nickel derivatives." *European Journal of Organic Chemistry*(12): 3257-3261.
79. Bonina, F. P., C. Puglia, et al. (2001). "In vitro and in vivo evaluation of polyoxyethylene esters as dermal prodrugs of ketoprofen, naproxen and diclofenac." *European Journal of Pharmaceutical Sciences* 14(2): 123-134.
80. Decosta, B. R., M. J. Iadarola, et al. (1992). "Probes for narcotic receptor mediated phenomena 0.18. epimeric 6-alpha-iodo-3,14-dihydroxy-17-(cyclopropylmethyl)-4, 5-alpha-epoxymorphi nans and 6-beta-iodo-3,14-dihydroxy-17-(cyclopropylmethyl)-4,5-alpha-epoxymorphin ans as potential ligands for opioid receptor single photon-emission computed-tomography-synthesis, evaluation, and radiochemistry of i-125 6-beta-iodo-3,14-dihydroxy-17-(cyclopropylmethyl)-4,5-alpha-epoxymorphin an." *Journal of Medicinal Chemistry* 35(15): 2826-2835.

81. Du, W. T., L. Hong, et al. (2007). "Synthesis and evaluation of water-soluble docetaxel prodrugs-docetaxel esters of malic acid." *Bioorganic & Medicinal Chemistry* 15(18): 6323-6330.

82. G. Venkateswar Reddy, R. S. C. K., K. Suresh Babu, J. Madhusudana Rao (2009). "Stereoselective syntheses of 11-a-methoxycurvularin 83. and 11-b-methoxycurvularin." *Tetrahedron Letters* 50: 4117-4120.

84. Hamad, M. O., P. K. Kiptoo, et al. (2006). "Synthesis and hydrolytic behavior of two novel tripartate codrugs of naltrexone and 6 beta-naltrexol with hydroxybupropion as potential alcohol abuse and smoking cessation agents." *Bioorganic & Medicinal Chemistry* 14(20): 7051-7061.

85. Jiang, Z. X. and Y. B. Yu (2008). "The design and synthesis of highly branched and spherically symmetric fluorinated macrocyclic chelators." *Synthesis-Stuttgart* (2): 215-220.

86. Krivickas, S. J., E. Tamanini, et al. (2007). "Effective Methods for the Biotinylation of Azamacrocycles." *The Journal of Organic Chemistry* 72(22): 8280-8289.

87. Mantarosie, L., S. Coman, et al. (2008). "Comparative behavior of various lipases in benign water and ionic liquids solvents." *Journal of Molecular Catalysis a-Chemical* 279(2): 223-229.

88. Mizrahi, B. and A. J. Domb (2009). "Anhydride Prodrug of Ibuprofen and Acrylic Polymers." *Aaps Pharmscitech* 10(2): 453-458.

89. Nelson, T. D., R. D. Davis, et al. (1994). "Synthesis and opioid receptor affinity of a series of aralkyl ethers of 6-alpha-naltrexol and 6-beta-naltrexol." *Journal of Medicinal Chemistry* 37(25): 4270-4277.

90. Paun, C., C. Stere, et al. (2008). "Acylation of sulfonamines using silica grafted 1-butyl-3-(3-triethoxysilyl-propyl)-4,5-dihydroimidazolium ionic liquids as catalysts." *Catalysis Today* 131(1-4): 98-103.

91. Pelotte, A. L., R. M. Smith, et al. (2009). "Design, synthesis, and characterization of 6[beta]-naltrexol analogs, and their selectivity for in vitro opioid receptor subtypes." *Bioorganic & Medicinal Chemistry Letters* 19(10): 2811-2814.

92. Rouquayrol, M., B. Gaucher, et al. (2001). "Synthesis and anti-HIV activity of glucose-containing prodrugs derived from saquinavir, indinavir and nelfinavir." *Carbohydrate Research* 336(3): 161-180.

93. Simas, A. B. C., K. C. Pais, et al. (2003). "A More Convenient and General Procedure for O-Monobenzy-lation of Diols via Stannylenes: A Critical Reevaluation of the Bu2SnO Method." *The Journal of Organic Chemistry* 68(13): 5426-5428.

94. Sunazuka, T., K. Tsuzuki, et al. (1992). "Synthesis of 1233a analogs and their inhibitory activity against hydroxymethylglutaryl coenzyme a synthase." *Journal of Antibiotics* 45(7): 1139-1147.

95. Prausnitz M R, Mitragotri S, Langer R 2004. Current status and future potential of transdermal drug delivery. *Nat Rev Drug Discov* 3(2):115-124.

96. Prausnitz M R, Langer R 2008. Transdermal drug delivery. *Nat Biotech* 26(11):1261-1268.

97. Prausnitz M R 2004. Microneedles for transdermal drug delivery. *Advanced Drug Delivery Reviews* 56(5):581-587.

98. Kaushik S, Hord A H, Denson D D, McAllister D V, Smitra S, Allen M G, Prausnitz M R 2001. Lack of pain associated with microfabricated microneedles. *Anesth Analg* 92(2):502-504.

99. Gill H S, Denson D D, Burris B A, Prausnitz M R 2008. Effect of Microneedle Design on Pain in Human Volunteers. *The Clinical Journal of Pain* 24(7):585-594 510.1097/AJP.1090b1013e31816778f31816779.

100. O'Malley S S, Jaffe A J, Chang G, Schottenfeld R S, Meyer R E, Rounsaville B 1992. Naltrexone and Coping Skills Therapy for Alcohol Dependence: A Controlled Study. *Arch Gen Psychiatry* 49(11):881-887.

101. Lee Y-k, Park S-w, Kim Y-k, Kim D-j, Jeong J, Myrick H, Kim Y-h 2005. Effects of naltrexone on the ethanol-induced changes in the rat central dopaminergic system *Alcohol and Alcoholism* 40(4):297-301.

102. Swift R 2010. Medications Acting on the Dopaminergic System in the Treatment of Alcoholic Patients. *Current Pharmaceutical Design* 16(19):2136-2140.

103. Hulse G K, Basso M R 2000. The association between naltrexone compliance and daily supervision. *Drug and Alcohol Review* 19(1):41-48.

104. Volpicelli J R, Rhines K C, Rhines J S, Volpicelli L A, Alterman A I, O'Brien C P 1997. Naltrexone and Alcohol Dependence: Role of Subject Compliance. *Arch Gen Psychiatry* 54(8):737-742.

105. McCaul M E, Wand G S, Rohde C, Lee S M 2000. Serum 6-Beta-Naltrexol Levels Are Related to Alcohol Responses in Heavy Drinkers. *Alcoholism: Clinical and Experimental Research* 24(9):1385-1391.

106. Hammell D C, Hamad M, Vaddi H K, Crooks P A, Stinchcomb A L 2004. A duplex "Gemini" prodrug of naltrexone for transdermal delivery. *Journal of Controlled Release* 97(2):283-290.

107. Haranath K V, Mohamed O H, Jianhong C, Stan L B, Peter A C, Audra L S 2005. Human skin permeation of branched-chain 3-O-alkyl ester and carbonate prodrugs of naltrexone. *Pharm Res* 22(5):758-765.

108. Kiptoo P K, Paudel K S, Hammell D C, Hamad M O, Crooks P A, Stinchcomb A L 2008. In vivo evaluation of a transdermal codrug of 6-beta-naltrexol linked to hydroxybupropion in hairless guinea pigs. *European journal of pharmaceutical sciences: official journal of the European Federation for Pharmaceutical Sciences* 33(4-5):371-379.

109. Banks S, Pinninti R, Gill H, Crooks P, Prausnitz M, Stinchcomb A 2008. Flux Across Microneedle-treated Skin is Increased by Increasing Charge of Naltrexone and Naltrexol In Vitro. *Pharmaceutical Research* 25(8):1964-1964.

110. Wermeling D P, Banks S L, Hudson D A, Gill H S, Gupta J, Prausnitz M R, Stinchcomb A L 2008. Microneedles permit transdermal delivery of a skin-impermeant medication to humans. *Proceedings of the National Academy of Sciences* 105(6):2058-2063.

111. Verebey K, Volavka J, Mule S J, Resnick R B 1976. Naltrexone: disposition, metabolism, and effects after acute and chronic dosing. *Clin Pharmacol Ther* 20(3): 315-328.

112. Banks S L, Pinninti R R, Gill H S, Paudel K S, Crooks P A, Brogden N K, Prausnitz M R, Stinchcomb A L 2010. Transdermal delivery of naltrexol and skin permeability lifetime after microneedle treatment in hairless guinea pigs. *Journal of Pharmaceutical Sciences* 99(7):3072-3080.

113. Kalluri H, Banga A 2011. Formation and Closure of Microchannels in Skin Following Microporation. *Pharmaceutical Research* 28(1):82-94.

114. Feingold K 2002. In This Issue: Regulation of Permeability Barrier Homeostasis. 119(5):986-986.

115. Feingold K R, Schmuth M, Elias P M 0000. The Regulation of Permeability Barrier Homeostasis. J Invest Dermatol 127(7):1574-1576.
116. Menon G K, Feingold K R, Elias P M 1992. Lamellar Body Secretory Response to Barrier Disruption. J Investig Dermatol 98(3):279-289.
117. Grubauer G, Elias P M, Feingold K R 1989. Transepidermal water loss: the signal for recovery of barrier structure and function. Journal of Lipid Research 30(3): 323-333.
118. Fecker L F, Stockfleth E, Nindl I, Ulrich C, Forschner T, Eberle J 2007. The role of apoptosis in therapy and prophylaxis of epithelial tumours by nonsteroidal antiinflammatory drugs (NSAIDs). British Journal of Dermatology 156:25-33.
119. Davidson J M, Breyer M D 2003. Inflammatory Modulation and Wound Repair. J Investig Dermatol 120(5):xi-xii.
120. Muller-Decker K, Hirschner W, Marks F, Furstenberger G 2002. The Effects of Cyclooxygenase Isozyme Inhibition onIncisional Wound Healing in Mouse Skin. 119(5): 1189-1195.
121. Futagami A, Ishizaki M, Fukuda Y, Kawana S, Yamanaka N 0000. Wound Healing Involves Induction of Cyclooxygenase-2 Expression in Rat Skin. Lab Invest 82(11):1503-1513.
122. Banks S, Paudel K, Brogden N, Loftin C, Stinchcomb A 2011. Diclofenac Enables Prolonged Delivery of Naltrexone Through Microneedle-Treated Skin. Pharmaceutical Research:1-9.
123. Schmid-Wendtner M H, Korting H C 2006. The pH of the Skin Surface and Its Impact on the Barrier Function. Skin Pharmacology and Physiology 19(6):296-302.
124. Vaddi H K, Banks S L, Chen J, Hammell D C, Crooks P A, Stinchcomb A L 2009. Human skin permeation of 3-O-alkyl carbamate prodrugs of naltrexone. Journal of Pharmaceutical Sciences 98(8):2611-2625.
125. Prusakiewicz J, Ackermann C, Voorman R 2006. Comparison of Skin Esterase Activities from Different Species. Pharmaceutical Research 23(7):1517-1524.
126. Oesch F, Fabian E, Oesch-Bartlomowicz B, Werner C, Landsiedel R 2007. Drug-Metabolizing Enzymes in the Skin of Man, Rat, and Pig. Drug Metabolism Reviews 39(4):659-698.
127. Milewski M, Stinchcomb A 2011. Vehicle Composition Influence on the Microneedle-Enhanced Transdermal Flux of Naltrexone Hydrochloride. *Pharmaceutical Research* 28(1):124-134.
128. U.S. Patent Application Publication No. 2012/0034293.
129. U.S. Patent Application Publication No. 2011/0245783.
130. U.S. Patent Application Publication No. 2011/0245288.
131. U.S. Patent Application Publication No. 2011/0052694.
132. U.S. Patent Application Publication No. 2010/0273895.
133. U.S. Patent Application Publication No. 2009/0291128.
134. U.S. Patent Application Publication No. 2009/0247619.
135. U.S. Patent Application Publication No. 2009/0246265.
136. U.S. Patent Application Publication No. 2009/0156814.
137. U.S. Patent Application Publication No. 2009/0143762.
138. U.S. Patent Application Publication No. 2009/0036523.
139. U.S. Patent Application Publication No. 2009/0017102.
140. U.S. Patent Application Publication No. 2008/0076789.
141. U.S. Patent Application Publication No. 2008/0008745.
142. U.S. Patent Application Publication No. 2005/0266061.
143. U.S. Patent Application Publication No. 2005/0154002.
144. U.S. Patent Application Publication No. 2003/0032892.
145. U.S. Patent Application Publication No. 2002/0111551.
146. U.S. Patent Application Publication No. 2002/0111377.
147. U.S. Patent Application Publication No. 2002/0098472.
148. U.S. Patent Application Publication No. 2002/0094515.
149. U.S. Pat. No. 7,759,358.
150. U.S. Pat. No. 7,511,054.
151. U.S. Pat. No. 7,232,460.
152. U.S. Pat. No. 7,229,556.
153. U.S. Pat. No. 6,569,449.

What is claimed is:

1. A compound having a first moiety derived from an opioid; and
a second moiety derived from a cyclooxygenase (COX) enzyme inhibitor;
wherein said first moiety is linked to said second moiety to form a single chemical entity;
wherein the compound has a structure selected from the group consisting of:

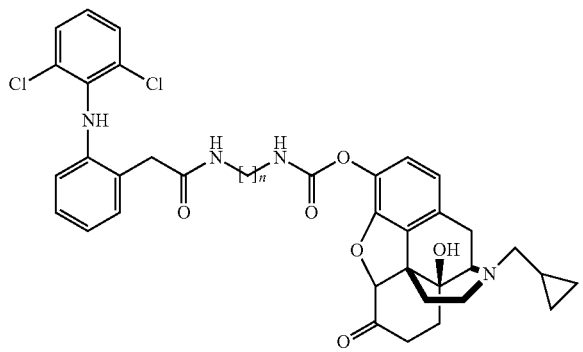

wherein n is 1, 2, 3, or 4, and

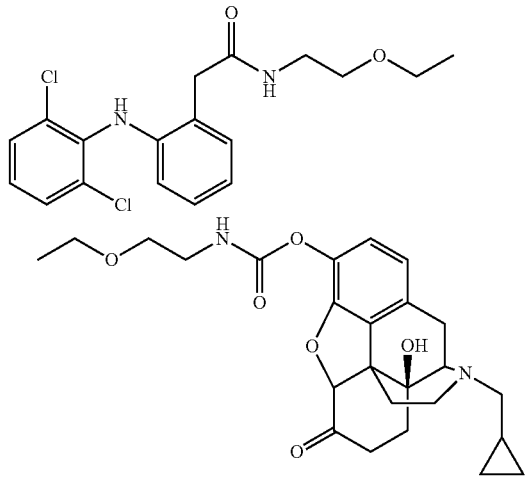

2. The compound of claim 1, wherein the opioid and the COX enzyme inhibitor are linked by a linker moiety.

3. The compound of claim 2, wherein the linker moiety is cleavable.

4. The compound of claim 3, wherein the linker moiety is cleavable by hydrolysis and/or enzymatic digestion.

5. The compound of claim 2, wherein the linker moiety confers increased aqueous solubility to the compound.

6. A method for treating a subject, comprising
identifying a subject in need of treatment for a condition selected from the group consisting of narcotic dependence, alcohol dependence, amphetamine dependence, and smoking dependence; and delivering to the subject a therapeutically effective amount of the compound of claim 1.

7. The method of claim 6, wherein following delivery to the subject, the compound is transformed into at least two active drug molecules.

8. The method of claim 7, wherein the transformation is by hydrolysis and/or enzymatic digestion.

9. The method of claim 6, wherein the compound is delivered transdermally.

10. The method of claim 9, wherein compound achieves improved duration of microporation-assisted delivery of the opioid as compared to the parent.

* * * * *